US011213514B2

(12) United States Patent
Simpson, Jr. et al.

(10) Patent No.: US 11,213,514 B2
(45) Date of Patent: Jan. 4, 2022

(54) ALPHA-1-ADRENERGIC RECEPTOR AGONIST THERAPY

(71) Applicants: The Regents of the University of California, Oakland, CA (US); The University of North Carolina at Chapel Hill, Chapel Hill, NC (US)

(72) Inventors: Paul C. Simpson, Jr., San Francisco, CA (US); Brian C. Jensen, Chapel Hill, NC (US)

(73) Assignees: The Regents of the University of California, Oakland, CA (US); The University of North Carolina at Chapel Hill, Chapel Hill, NC (US)

( * ) Notice: Subject to any disclaimer, the term of this patent is extended or adjusted under 35 U.S.C. 154(b) by 0 days.

(21) Appl. No.: 16/079,548

(22) PCT Filed: Feb. 24, 2017

(86) PCT No.: PCT/US2017/019522
§ 371 (c)(1),
(2) Date: Aug. 23, 2018

(87) PCT Pub. No.: WO2017/147532
PCT Pub. Date: Aug. 31, 2017

(65) Prior Publication Data
US 2019/0117623 A1 Apr. 25, 2019

Related U.S. Application Data

(60) Provisional application No. 62/450,996, filed on Jan. 26, 2017, provisional application No. 62/300,549, filed on Feb. 26, 2016.

(51) Int. Cl.
*A61K 31/4164* (2006.01)
*A61K 31/704* (2006.01)
*A61P 9/10* (2006.01)
*A61K 45/06* (2006.01)

(52) U.S. Cl.
CPC ........ *A61K 31/4164* (2013.01); *A61K 31/704* (2013.01); *A61K 45/06* (2013.01); *A61P 9/10* (2018.01)

(58) Field of Classification Search
CPC .................................................. A61K 31/4164
See application file for complete search history.

(56) References Cited

U.S. PATENT DOCUMENTS

| 2013/0040904 | A1 | 2/2013 | Simpson | |
| 2013/0288971 | A1 | 10/2013 | Most et al. | |
| 2014/0121257 | A1* | 5/2014 | Simpson, Jr. | A61K 31/4164 |
| | | | | 514/401 |

OTHER PUBLICATIONS

Musselman, D.M. et al., BJU International, "A randomized crossover study to evaluate Ro 115-1240, a selective alpha-1 A/1L-adrenoceptor partial agonist in women with stress urinary incontinence", 2003, vol. 93, pp. 78-83 (Year: 2003).*
Pubchem, "Dabuzalgron hydrochloride"; also available at https://pubchem.ncbi.nlm.nih.gov/compound/Dabuzalgron-hydrochloride#section=MeSH-Entry-Terms&fullscreen=true; viewed online Jan. 16, 2020 (Year: 2020).*
Beak, J. Y. et al., J. Am. Coll. Cardiol. Basic Trans Science "An Oral Selective Alpha-1A Adrenergic Receptor Agonist Prevents Doxorubicin Cardiotoxicity", 2017, vol. 2, No. 1, pp. 39-53 (Year: 2017).*
"Prevent", WordNet Search 3.1, obtained from wordnetweb.princeton.edu/perl; last obtained 2021 (Year: 2021).*
ALLHATT. (Apr. 19, 2000). Major cardiovascular events in hypertensive patients randomized to doxazosin vs chlorthalidone: The antihypertensive and lipid-lowering treatment to prevent heart attack trial (ALLHATT). JAMA. 283(15):1967-1975.
Amin, J.K. et al. (2001). "Reactive oxygen species mediate α-adrenergic receptor-stimulated hypertrophy in adult rat ventricular myocytes," *J Mol Cell Cardiol.* 33:131-139.
Bielecka-Dabrowa, A. et al. (2008). "New methods in laboratory diagnostics of dilated cardiomyopathy, "*Cardiology J.* 15(4):388-395.
Bishop M.J. (2007). "Recent advances in the discovery of $\alpha_1$-adrenoceptor agonists," *Curr Top Med Chem.* 7:135-145.
Bloom, M.W. et al. (Jan. 2016). "Cancer therapy-related cardiac dysfunction and heart failure: Part 1: Definitions, pathophysiology, risk factors, and imaging," *Circ Heart Fail.* 9(1):e002661.
Blue, D.R. et al. (Jan. 2004). "Pharmacological characteristics of Ro 115-1240, a selective α1A/1L-adrenoceptor partial agonist: a potential therapy for stress urinary incontinence," BJU Int. 93(1):162-170.
Bristow, M.R. et al. (1988). "Alpha-1 adrenergic receptors in the nonfailing and failing human heart," *J Pharmacol Exp Ther.* 247(3):1039-1045.
Bullard, J.H. et al. (2010). "Evaluation of statistical methods for normalization and differential expression in mrna-seq experiments," BMC bioinformatics 11:94.
Cardinale, D. et al. (Jun. 2, 2015). "Early detection of anthracycline cardiotoxicity and improvement with heart failure therapy," Circulation. 131:1981-1988.
Chan T. et al. (2008). Abstract 5355 "An alpha-1a-adrenergic receptor subtype agonist prevents cardiomyopathy without increasing blood pressure," Circulation 118:No. Suppl 18.
Chaulet H. et al. (Apr. 2006, e-published Mar. 6, 2006). "Sustained augmentation of cardiac $\alpha_{1A}$-adrenergic drive results in pathological remodeling with contractile dysfunction, progressive fibrosis and reactivation of matricellular protein genes," *J Mol Cell Cardiol.* 40(4):540-552.
Collette, K.M et al. (2014). "Long-term alphalb-adrenergic receptor activation shortens lifespan, while $\alpha_{1A}$-adrenergic receptor stimulation prolongs lifespan in association with decreased cancer incidence," Age 36:9675.
Dash, R. et al. (Oct. 2011, e-published Feb. 28, 2011). "A molecular MRI probe to detect treatment of cardiac apoptosis in vivo," Magn. Reson. Med. 66(4): 1152-1162.

(Continued)

Primary Examiner — Bahar Craigo
(74) Attorney, Agent, or Firm — Mintz, Levin, Cohn, Ferris, Glovsky and Popeo, P.C.

(57) ABSTRACT

Presented herein, inter alia, are novel methods of treating heart diseases.

15 Claims, 11 Drawing Sheets
Specification includes a Sequence Listing.

(56) References Cited

OTHER PUBLICATIONS

Doze, V.A. et al. (2011). "Long-term $\alpha_{1A}$-adrenergic receptor stimulation improves synaptic plasticity, cognitive function, mood, and longevity," Mol Pharmacol. 80(4):747-758.

Du ,X.J. et al. (2004). "Genetic enhancement of ventricular contractility protects against pressure-overload-induced cardiac dysfunction," J Mot Cell Cardiol. 37:979-987.

Du, X.J. et al. (2006). "Transgenic $\alpha_{1A}$-adrenergic activation limits post-infarct ventricular remodeling and dysfunction and improves survival," Cardiovasc Res. 71:735-743.

Esbenshade, T.A. et al. (May 1995). "Cloning of the human α 1d-adrenergic receptor and inducible expression of three human subtypes in SK-N-MC cells," Mol. Pharmacal. 47(5):977-985.

Extended European Search Report dated Sep. 5, 2019, for EP Patent Application No. 17757383.9, 6 pages.

Gottlieb, E. et al. (2003). "Mitochondrial membrane potential regulates matrix configuration and cytochrome c release during apoptosis," Cell Death Differ. 10:709-717.

Graham, R.M. et al. (May 1996). "α1-adrenergic receptor subtypes. Molecular structure, function, and signaling," Circ Res 78(5):737-749.

Guo. J. et al. (2009). "P66shc links $\alpha_{1A}$-adrenergic receptors to a reactive oxygen species-dependent akt-foxo3a phosphorylation pathway in cardiomyocytes," Circ Res. 104:660-669.

Huang Y. et al. (Feb. 13, 2007). "α1A-adrenergic-extracellular signal-regulated kinase survival signaling pathway in cardiac myocytes," Circulation 115:763-772.

International Search Report dated May 11, 2017, for PCT Application No. PCT/US2017/019522, filed Feb. 24, 2017, 3 pages.

Jensen, B.C. et al. (2009). The α-1D is the predominant alpha-1-adrenergic receptor in human epicardial coronary arteries. JACC. 54:1137-1145.

Jensen, B.C. et al. (2009). "α1-adrenergic receptor subtypes in nonfailing and failing human myocardium," Circ Heart Fail. 2:654-663.

Jensen, B.C. et al. (2011). "α-1-adrenergic receptors: Targets for agonist drugs to treat heart failure," JMol Cell Cardiol. 51:518-528.

Jensen B.C. et al. (2014). "α-1-adrenergic receptors in heart failure: The adaptive arm of the cardiac response to chronic catecholamine stimulation," J Cardiovasc Pharmacol. 63:291-301.

KREGE,,J.H. et al. (1995). "A noninvasive computerized tail-cuff system for measuring blood pressure in mice," Hypertension. 25:1111-1115.

Li, B. et al. (2011). "RSEM: Accurate transcript quantification from ma-seq data with or without a reference genome," BMC bioinformatics. 2011:12:323.

Lin, F. et al. (Aug. 17, 2001). "Targeted $\alpha_{1A}$-adrenergic receptor overexpression induces enhanced cardiac contractility but not hypertrophy," Circ Res. 89:343-350.

Minneman, K.P. et al. (Nov. 1994). "Selectivity of agonists for cloned α 1-adrenergic receptor subtypes," Mol Pharmacol 46(5):929-936.

Minneman, K.P. et al. (1994). "α 1-adrenergic receptor subtypes," Annu Rev Pharmacol Toxicol 34:117-133.

Moslehi, J. et al. (Feb. 27, 2017). "Cardio-Oncology: Time to Get More Mechanistic," JACC Basic Transl Sci 2(1):54-55.

Musselman, D.M. et al. (2004). "A randomized crossover study to evaluate Ro 115-1240, a selective $\alpha_{1A/1L}$-adrenoceptor partial agonist in women with stress urinary incontinence," BJU International. 93:78-83.

Nellessen, U. et al. (May 2006). Serial analysis of troponin I levels in patients with ischemic and nonischemic dilated cardiomyopathy, Clin. Cardial. 29(5):219-224.

O'Connell, T.D. et al. (Jan. 2014). Cardiac $\alpha_1$-adrenergic receptors: Novel aspects of expression, signaling mechanisms, physiologic function, and clinical importance. Pharmacological reviews. 66:308-333.

Patel,M.B. et al. (Nov. 1991). "Altered function and structure of the heart in dogs with chronic elevation in plasma norepinephrine," Circulation. 84:2091-2100.

(Pubchem) CID 216249 Dabuzalgron. PubChem Open Chemistry database [online]. Aug. 9, 2005 [retrieved on Apr. 19, 2017]. Retrieved from the Internet: <URL: https://pubchem.ncbi.nlm.nih.gov/compound/Dabuzalgron>; 15 pages.

(Pubchem) A 61603 Hydrochloride. PubChem Open Chemistry database [online]. Oct. 25, 2006 [retrieved on Apr. 19, 2017]. Retrieved from the Internet: <URL: https://pubchem.ncbi.nlm.nih.gov/compound/Dabuzalgron>; 14 pages.

Rokosh, D.G et al. (Jul. 9, 2002). "Knockout of the α1 A/C-adrenergic receptor subtype: The αA/C is expressed in resistance arteries and is required to maintain arterial blood pressure," Proc Natl Acad Sci USA. 99(14):9474-9479.

Rorabaugh ,B.R. et al. (2005). "$\alpha_{1A}$—but not $\alpha_{1B}$-adrenergic receptors precondition the ischemic heart by a staurosporine-sensitive, chelerythrine-insensitive mechanism," Cardiovasc Res.65:436-445.

Rosca, M.G. et al. (Feb. 2013). "Mitochondria in cardiac hypertrophy and heart failure," JMol Cell Cardiol. 55:31-41.

Shibata, K. et al. (Aug. 1995). "KMD-3213, a novel, potent, α1a-adrenoceptor-selective antagonist: characterization using recombinant human α1-adrenoceptors and native tissues," Mol. Pharmacal 48(2):250-258.

Shibata, K. et al. (Jan. 3, 2003, e-published Oct. 29, 2002). "α1-Adrenergic receptor subtypes differentially control the cell cycle of transfected CHO cells through a cAMP-dependent mechanism involving p27Kip1," J Biol Chem 278(1):672-678.

Simpson, P. et al. (1982). "Differentiation of rat myocytes in single cell cultures with and without proliferating nonmyocardial cells. Cross-striations, ultrastructure, and chronotropic response to isoproterenol," Circ Res. 50:101-116.

Subramanian, A. et al. (Oct. 25, 2005). "Gene set enrichment analysis: A knowledgebased approach for interpreting genome-wide expression profiles," Proc Natl Acad Sci USA. 102:15545-15550.

Suliman, H.B. et al. (Dec. 2007). The co/ho system reverses inhibition of mitochondrial biogenesis and prevents murine doxorubicin cardiomyopathy. J Clin Invest. 117:3730-3741.

Tokarska-Schlattner, M. et al. (2006). "New insights into doxorubicin-induced cardiotoxicity: The critical role of cellular energetics," Mol Cell Cardiol. 41:389-405.

Turnbull, L. et al. (2003). "Alpha$_1$-Adrenergic receptor responses in $\alpha_{1ab}$-AR knockout mouse hearts suggest the presence of $\alpha_{1D}$-AR," Am J Physiol Heart Circ Physiol. 284:H1104-1109.

Van Der Pal, H.J. et al. (2010). "Cardiac function in 5-year survivors of childhood cancer: A long-term follow-up study. Archives of internal medicine," 170(14):1247-1255.

Varga, Z.V. et al. (2015). "Drug-induced mitochondrial dysfunction and cardiotoxicity," Am J Physiol Heart Circ Physiol. 309:H1453-1467.

Wang, K. et al. (Aug. 28, 2010). "Mapsplice: Accurate mapping of RNA-seq reads for splice junction discovery," Nucleic acids research 38(18):e178.

Weinberg, D.H. et al. (Jun. 30, 1994). "Cloning, expression and characterization of human a adrenergic receptors α1A, α1B and α1C," Biochem Biophys Res Common 201(3):1296-1304.

Written Opinion dated May 11, 2017, for PCT Application No. PCT/US2017/019522, filed Feb. 24, 2017, 6 pages.

Zakir R.M. et al. (May-Jun. 2009). "The use of midodrine in patients with advanced heart failure," Congest Heart Fail. 15:108-111.

* cited by examiner

SEQUENCE LISTING

<160> NUMBER OF SEQ ID NOS: 28

<210> SEQ ID NO 1
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 1
ggcggtttgg ctaggttt                                                 18

<210> SEQ ID NO 2
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 2
gggttatctt cacacaccat ga                                            22

<210> SEQ ID NO 3
<211> LENGTH: 20

```
<212> TYPE: DNA
<213> ORGANISM: Artificial Sequence
<220> FEATURE:
<223> OTHER INFORMATION: Synthetic polynucleotide

<400> SEQUENCE: 3
ggggagctgt gatgtgaagt                                           20

<210> SEQ ID NO 4
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 4
ccaggaaata attctggctc ata                                       23

<210> SEQ ID NO 5
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 5
aatccgcatc atgaacagtg                                           20

<210> SEQ ID NO 6
<211> LENGTH: 22
<212> TYPE: DNA
<213> ORGANISM: Artificial Sequence
<220> FEATURE:
<223> OTHER INFORMATION: Synthetic polynucleotide

<400> SEQUENCE: 6
tcatcatcca ttttatccac ca                                        22

<210> SEQ ID NO 7
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 7
ttcggctcag tggagagg                                             18

<210> SEQ ID NO 8
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 8
gctcccacca tttctccag                                            19

<210> SEQ ID NO 9
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 9
```

```
attgtggtgg gatgcttcgt cct                                              23

<210> SEQ ID NO 10
<211> LENGTH: 24
<212> TYPE: DNA
<213> ORGANISM: Artificial Sequence
<220> FEATURE:
<223> OTHER INFORMATION: Synthetic polynucleotide

<400> SEQUENCE: 10
tgtttccggt ggcttgaaat tcgg                                             24

<210> SEQ ID NO 11
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 11
ggttgcttcg tcctctgct                                                   19

<210> SEQ ID NO 12
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 12
gaaatccggg aagaaagacc                                                  20

<210> SEQ ID NO 13
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 13
cacagatctg atggatttca aga                                              23

<210> SEQ ID NO 14
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 14
cctcatcttc taccggcatc                                                  20

<210> SEQ ID NO 15
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 15
cacagatctg atggatttca aga                                              23

<210> SEQ ID NO 16
<211> LENGTH: 20
<212> TYPE: DNA
<213> ORGANISM: Artificial Sequence
```

```
<220> FEATURE:
<223> OTHER INFORMATION: Synthetic polynucleotide

<400> SEQUENCE: 16
cctcatcttc taccggcatc                                               20

<210> SEQ ID NO 17
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 17
cctgccatgt atgtggctat c                                             21

<210> SEQ ID NO 18
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 18
ccagaatcca acacgatgc                                                19

<210> SEQ ID NO 19
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 19
tgaagcctca cttcctaccc                                               20

<210> SEQ ID NO 20
<211> LENGTH: 23
<212> TYPE: DNA
<213> ORGANISM: Artificial Sequence
<220> FEATURE:
<223> OTHER INFORMATION: Synthetic polynucleotide

<400> SEQUENCE: 20
cgtcacacat ggtgtctagt ttc                                           23

<210> SEQ ID NO 21
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 21
ctgcaggacc tggtggac                                                 18

<210> SEQ ID NO 22
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 22
ggaacttgga caggttggtg                                               20
```

```
<210> SEQ ID NO 23
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 23
ctccacgcac cctcactt                                             18

<210> SEQ ID NO 24
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 24
catgaccagg gggttgtc                                             18

<210> SEQ ID NO 25
<211> LENGTH: 21
<212> TYPE: DNA
<213> ORGANISM: Artificial Sequence
<220> FEATURE:
<223> OTHER INFORMATION: Synthetic polynucleotide

<400> SEQUENCE: 25
agcctgcgaa catatttgag a                                         21

<210> SEQ ID NO 26
<211> LENGTH: 19
<212> TYPE: DNA
<213> ORGANISM: Artificial Sequence
<220> FEATURE:
<223> OTHER INFORMATION: Synthetic polynucleotide

<400> SEQUENCE: 26
atgagggcaa tccgtcttc                                            19

<210> SEQ ID NO 27
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 27
gcagtcgcaa catgctca                                             18

<210> SEQ ID NO 28
<211> LENGTH: 20
<212> TYPE: DNA
<213> ORGANISM: Artificial Sequence
<220> FEATURE:
<223> OTHER INFORMATION: Synthetic polynucleotide

<400> SEQUENCE: 28
gggtcatttg gtgactctgg                                           20
```

ALPHA-1-ADRENERGIC RECEPTOR AGONIST THERAPY

CROSS-REFERENCES TO RELATED APPLICATIONS

This application claims the benefit of U.S. Provisional Application No. 62/300,549, filed Feb. 26, 2016 and U.S. Provisional Application No. 62/450,996, filed Jan. 26, 2017, which is incorporated herein by reference in its entirety and for all purposes.

STATEMENT AS TO RIGHTS TO INVENTIONS MADE UNDER FEDERALLY SPONSORED RESEARCH AND DEVELOPMENT

This invention was made with government support under grant nos. R01 HL031113, K08 HL085293, HL080074, TR000111 and HL096836, awarded by the National Institutes of Health. The government has certain rights in the invention.

REFERENCE TO A SEQUENCE LISTING, A TABLE OR A COMPUTER PROGRAM LISTING APPENDIX SUBMITTED AS AN ASCII TEXT FILE

The Sequence Listing written in file 48536-556001WO_ST25.TXT, created on Feb. 24, 2017, 5,878 bytes, machine format IBM-PC, MS Windows operating system, is hereby incorporated by reference.

BACKGROUND OF THE INVENTION

Most drugs for treating heart muscle disease are antagonists or inhibitors, such as beta-adrenergic blockers, or angiotensin converting enzyme inhibitors, or aldosterone or angiotensin receptor blockers. The basic rationale for using these antagonists is to block cellular pathways that are toxic or harmful to the cell. These drugs may be effective in conditions such as heart failure, but their efficacy is limited. At the present time, no drugs are commonly used, which take the approach of activating cellular pathways that are beneficial or helpful to the cell. Alpha-1-adrenergic receptors control numerous adaptive processes in the heart. Alpha-1-adrenergic receptor agonists in current clinical use are designed to stimulate smooth muscle contraction, for example to treat hypotension or urinary incontinence, and are used in amounts that result in smooth muscle contraction. Such smooth muscle contraction may not be beneficial for patients with many heart or brain related diseases. The present invention provides solutions to these and other problems in the art.

BRIEF SUMMARY OF THE INVENTION

In a first aspect is provided a method of treating or preventing cardiomyopathy in a subject in need of such treatment, the method including administering a therapeutically or prophylactically effective amount of the alpha-1A ($\alpha$1A) adrenergic receptor agonist, dabuzalgron, or an analog, pharmaceutically acceptable salt, or prodrug thereof.

In another aspect is provided a method of treating or preventing heart failure in a subject in need of such treatment, the method including administering a therapeutically or prophylactically effective amount of dabuzalgron, or an analog, pharmaceutically acceptable salt, or prodrug thereof. In embodiments, the method includes improving (e.g. increasing) heart contraction.

In another aspect is provided a method of improving heart contraction in a subject in need of such treatment, the method including administering a therapeutically effective amount of dabuzalgron, or an analog, pharmaceutically acceptable salt, or prodrug thereof.

In another aspect is provided a method of treating or preventing cardiotoxicity in a subject in need of such treatment, the method including administering a therapeutically or prophylactically effective amount of dabuzalgron, or an analog, pharmaceutically acceptable salt, or prodrug thereof.

In another aspect is provided a method of modulating the activity of an $\alpha$1A adrenergic receptor. The method including contacting the $\alpha$1A adrenergic receptor with an effective amount of a compound described herein (e.g., dabuzalgron or an analog, pharmaceutically acceptable salt, or prodrug thereof).

BRIEF DESCRIPTION OF THE DRAWINGS

FIG. 1A. Blood pressure (BP) and heart rate (HR) were measured non-invasively in male mice for 10 consecutive days using a CODA Volume Pressure Recording tail cuff system (Kent Scientific). All daily values represent the average of at least 20 cuff inflations. Mice were acclimatized to the apparatus for the first 5 days, during which no drug was administered. On Days 6-10, mice received Dabuzalgron (100 ng/kg-100 µg/kg) or water by gavage twice daily. HR and systolic BP are unaffected by 5 days of treatment with Dabuzalgron. FIG. 1B. Male mice were treated with Dabuzalgron 10 µg/kg by gavage twice daily for 7 days. Heart weight (HW, in mg) was indexed to tibia length (TL, in mm). FIG. 1C. Quantitative RT-PCR was performed using heart tissue snap frozen at the time of sacrifice. Target transcripts (ANP=atrial natriuretic peptide; MHC$\beta$=myosin heavy chain beta; $\alpha$-skAct=alpha skeletal actin) were quantified relative to two standard transcripts (Polr2a=DNA-directed RNA polymerase II, subunit A; TBP=TATA-binding protein).

FIG. 2A. Fractional shortening, a measure of contractile function, with representative M-mode echocardiogram images. Results were compared across treatment conditions by ANOVA. FIG. 2B. Heart sections from some of these mice (i.e. wild type mice) stained with Masson Trichrome. Fibrosis (weighted average collagen content) was quantified using Aperio ImageScope software. Results were compared across treatment conditions by ANOVA.

FIG. 3A. RNAseq was performed on an Illumina HiSeq2000 system using RNA isolated from the hearts of 3 mice per treatment group (PBS+water; PBS+Dabuzalgron; Doxorubicin+water; Doxorubicin+ Dabuzalgron). Gene set analysis was performed on the DESeq2-derived statistics from an omnibus test across these four categories. The results were highly enriched in gene sets involved in mitochondrial processes, a selection of which are shown here. FIG. 3B. RNA abundance for all sequenced cytochrome C oxidase subunits (25 genes), mitochondrial complex I subunits (42 genes), and ATP synthase subunits (17 genes) was aggregated by group and compared to vehicle treatment. FIG. 3C. Quantitative RT-PCR for peroxisome proliferator-activated receptor gamma coactivator 1-alpha (PGC1α) was performed on mouse heart tissue (n in individual bars) FIG. 3D. ATP content was measured in freshly harvested mouse heart tissue (total n in individual bars), then quantified relative to protein content. Results are presented relative to vehicle treatment for 4 independent experiments. FIG. 3E. Thiobarbituric acid reactive substances (TBARS) were assayed in mouse myocardium.

FIG. 4A. Representative Western blot. FIG. 4B. The EC50 was calculated from 4 concentrations of Dabuzalgron across 5 separate experiments. FIG. 4C. Summary of pERK/ERK for experiments using 5 different NRVM isolations. The average pERK/ERK ratio for each experiment was derived from at least 2 individual wells and normalized to the pERK/ERK ratio for vehicle treated NRVMs. FIG. 4D and FIG. 4E. Mice were treated with DOX, DOX and dabuzalgron, trametinib (Tram), or DOX, dabuzalgron and Trm for 7 days. Heart lysates were blotted for pERK and ERK. Results were compared using one way ANOVA with Tukey post-test. FIG. 4F. Mice underwent conscious echocardiography after 7 days of treatment with Tram, DOX and Tram, or DOX, Tram and dabuzalgron.

FIG. 5A. Representative epifluorescence microscopy for each treatment condition. FIG. 5B. Fluorescence intensity was analyzed using Image J software for 3 independent experiments, using at least 2 wells per condition for each experiment.

FIG. 6A. Mitochondrial membrane potential was assessed using JC-1 and fluorescent intensity was quantified using a plate reader. Red indicates intact mitochondrial membrane potential; green indicates compromised mitochondrial membrane potential (relative). Representative images and summary findings are presented in FIGS. 6B-6C. Lysates were blotted for selected regulators of apoptosis and mitochondrial cell death effectors. Representative Western blots and summary findings from 3 independent experiments with at least 2 wells per condition in each experiment are shown.

DETAILED DESCRIPTION OF THE INVENTION

I. Definitions

Figure 1A:
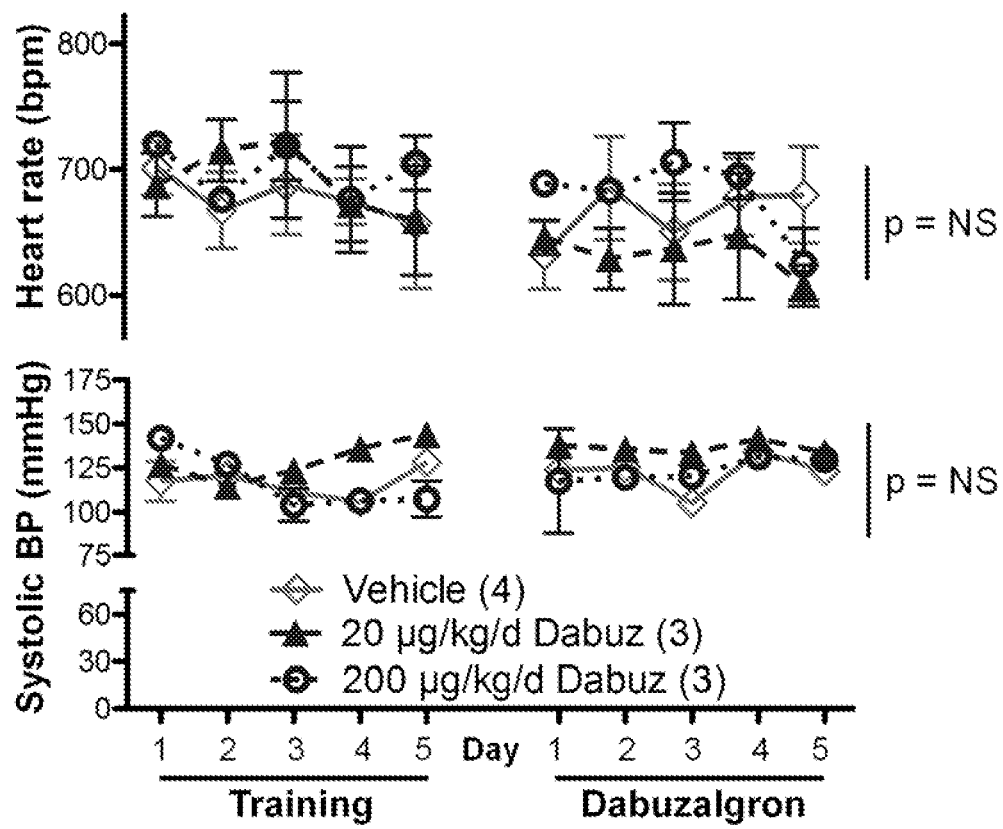
FIGS. 1A-1C. Dabuzalgron does not affect blood pressure or cause myocardial hypertrophy in uninjured wild type mice.

The abbreviations used herein have their conventional meaning within the chemical and biological arts. The chemical structures and formulae set forth herein are constructed according to the standard rules of chemical valency known in the chemical arts.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds, agents, or drugs of the invention. One of skill in the art will recognize that other pharmaceutical excipients are useful in the present invention.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, oxalic, methanesulfonic, and the like. Also included are salts of amino acids such as arginate and the like, and salts of organic acids like glucuronic or galactunoric acids and the like (see, for example, Berge et al., "Pharmaceutical Salts", *Journal of Pharmaceutical Science,* 1977, 66, 1-19). Certain specific compounds of the present invention contain both basic and acidic functionalities that allow the compounds to be converted into either base or acid addition salts.

As used herein, the term "salt" refers to acid or base salts of the compounds used in the methods of the present invention. Illustrative examples of acceptable salts are mineral acid (e.g., hydrochloric acid, hydrobromic acid, phosphoric acid, and the like) salts, organic acid (e.g., acetic acid, propionic acid, glutamic acid, citric acid and the like) salts, quaternary ammonium (e.g., methyl iodide, ethyl iodide, and the like) salts.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

In addition to salt forms, the present invention provides compounds, which are in a prodrug form. Prodrugs of the compounds described herein are those compounds that undergo chemical changes under physiological conditions to provide the compounds of the present invention. Additionally, prodrugs can be converted to the compounds of the present invention by chemical or biochemical methods in an ex vivo environment. For example, prodrugs can be converted to the compounds of the present invention when placed in a transdermal patch reservoir with a suitable enzyme or chemical reagent. In some embodiments, prodrugs of the compounds described herein (also referred to herein as "compound of the present invention") may be used in the methods described herein (including embodiments).

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. Certain compounds of the present invention can exist in polymorphic forms. In general, all physical forms are equivalent for the uses contemplated by the present invention and are intended to be within the scope of the present invention.

Certain compounds of the present invention may possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms unless specified otherwise. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, a compound described herein is also meant to include all stereochemical forms of the compound; i.e., the R and S configurations for each asymmetric center. Therefore, single stereochemical isomers as well as enantiomeric and diastereomeric mixtures of the present compounds are within the scope of the invention.

Unless otherwise stated, compound described herein are also meant to include compounds which differ only in the presence of one or more isotopically enriched atoms. For example, compounds described herein with replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^3$H), iodine-125 ($^{125}$I), or carbon-14 ($^{14}$C). All isotopic variations of the compounds of the present invention, whether radioactive or not, are encompassed within the scope of the present invention.

It should be noted that throughout the application that alternatives are written in Markush groups. It is specifically contemplated that each member of the Markush group should be considered separately, thereby comprising another embodiment.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Description of compounds of the present invention is limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions.

The term "modulator" refers to a composition that increases or decreases the level of a target molecule or the function of a target molecule or the level or function of a target cell (e.g., a target may be α1 adrenergic receptor (e.g., α1A-AR) and the function to be increased or decreased may be receptor activation or downstream signaling from the receptor (e.g. ERK protein, phosphorylated ERK, or pathway) or a target may be a cardiac cell and the modulator may increase or decrease the level or number of cells or modulate the health or survival of the cell). In some embodiments, a modulator is a compound that reduces the severity of one or more symptoms of a disease (e.g., loss of cell function, loss of cells). In some embodiments, a modulator reduces the deterioration of heart muscle cells or heart muscle cell function.

The term "preparation" is intended to include the formulation of the active agents (e.g. compound, drug) with material as a carrier providing a dosage form in which the active component with or without other carriers, is associated with a carrier. Similarly, cachets and lozenges are included. Tablets, powders, capsules, pills, cachets, and lozenges can be used as solid dosage forms suitable for oral administration.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, the certain methods presented herein successfully treat cardiomyopathy. For example, the certain methods presented herein successfully treat cardiotoxicity. For example, the certain methods presented herein successfully treat cardiomyopathy by decreasing the incidence of cardiomyopathy and/or preventing, stopping, reversing, or slowing the development of cardiomyopathy. For example, the certain methods presented herein successfully treat cardiotoxicity by decreasing the incidence of cardiotoxicity and/or preventing, stopping, reversing, or slowing the development of cardiotoxicity. The term "treating" and conjugations thereof, include prevention of an injury, pathology, condition, or disease (e.g. cardiomyopathy or cardiotoxicity). The term "treating" and conjugations thereof, includes a reduction the symptoms of an injury, pathology, condition, or disease (e.g. cardiomyopathy or cardiotoxicity). In embodiments treating is preventing. In embodiments, treating does not include preventing.

An "effective amount" is an amount sufficient to accomplish a stated purpose (e.g. achieve the effect for which it is administered, treat a disease, increase enzyme activity, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." The full therapeutic effect does not necessarily occur by administration of one dose, and may occur only after administration of a series of doses (e.g., divided doses wherein the therapeutically effective amount may be the amount in each individual dose that has a therapeutic effect when administered in a series of such doses or the therapeutically effective dose may be the amount in each individual dose wherein the therapeutic effect is achieved by each dose). Thus, a therapeutically effective amount may be administered in one or more administrations. A "reduction" of a symptom or symptoms (and grammatical equivalents of this phrase) means decreasing of the severity or frequency of the symptom(s), or elimination of the symptom(s). A "prophylactically effective amount" of an agent (e.g. compound, drug, or dabuzalgron, or an analog, pharmaceutically acceptable salt, or prodrug thereof) is an amount of an agent (e.g. compound, drug, or dabuzalgron, or an analog, pharmaceutically acceptable salt, or prodrug thereof) that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of an agent (e.g. compound, drug, antagonist, or dabuzalgron, or an analog, pharmaceutically acceptable salt, or prodrug thereof) required to decrease the activity of an enzyme relative to the absence of the agent (e.g. compound, drug, antagonist, or dabuzalgron, or an analog, pharmaceutically acceptable salt, or prodrug thereof). A "function disrupting amount," as used herein, refers to the amount of an agent (e.g. compound, drug, antagonist, or dabuzalgron, or an analog, pharmaceutically acceptable salt, or prodrug thereof) required to disrupt the function of an enzyme or protein relative to the absence of the agent (e.g. compound, drug, antagonist, or dabuzalgron, or an analog, pharmaceutically acceptable salt, or prodrug thereof). A "function increasing amount," as used herein, refers to the amount of an agent (e.g. compound, drug, agonist, or dabuzalgron, or an analog, pharmaceutically acceptable salt, or prodrug thereof) required to increase the function of an enzyme or protein relative to the absence of the agent (e.g. compound, drug, agonist, or dabuzalgron, or an analog, pharmaceutically acceptable salt, or prodrug thereof). The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy,* 20th Edition, 2003, Gennaro, Ed., Lippincott, Williams & Wilkins).

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In embodiments, a control is a patient not administered an α1 adrenergic receptor agonist (e.g. dabuzalgron, or an analog, pharmaceutically acceptable salt, or prodrug thereof). In embodiments, a control is a biological sample not administered an α1 adrenergic receptor agonist (e.g. dabuzalgron, or an analog, pharmaceutically acceptable salt, or prodrug thereof). In embodiments, a control is a cell not administered an α1 adrenergic receptor agonist (e.g. dabuzalgron, or an analog, pharmaceutically acceptable salt, or prodrug thereof). In embodiments, a control is a cell not administered dabuzalgron. In embodiments, a control is a patient not administered dabuzalgron. In embodiments, a control is a biological sample not administered dabuzalgron.

"Contacting" is used in accordance with its plain ordinary meaning and refers to the process of allowing at least two distinct species (e.g. agent (e.g. compound, drug, antagonist, agonist, or dabuzalgron, or an analog, pharmaceutically acceptable salt, or prodrug thereof), chemical compounds including biomolecules, or cells) to become sufficiently proximal to react, interact or physically touch. It should be understood, however, that the resulting reaction product can be produced directly from a reaction between the added reagents or from an intermediate from one or more of the added reagents which can be produced in the reaction mixture.

The term "contacting" may include allowing two species to react, interact, or physically touch, wherein the two species may be an agent (e.g. compound, drug, antagonist, agonist, or dabuzalgron, or an analog, pharmaceutically acceptable salt, or prodrug thereof) as described herein and a receptor (e.g. α1 adrenergic receptor, α1A-AR, α1B-AR, or α1D-AR); or an agent (e.g. compound, drug, antagonist, agonist, or dabuzalgron, or an analog, pharmaceutically acceptable salt, or prodrug thereof) as described herein and a cardiac cell or heart cell. In embodiments, a receptor is α1A-AR. In embodiments, a receptor is human α1A-AR.

As defined herein, the term "inhibition", "inhibit", "inhibiting" and the like in reference to a target-agent (e.g. compound, drug, antagonist) or protein-inhibitor interaction means negatively affecting (e.g., decreasing) the activity or function of the target or protein relative to the activity or function of the target or protein in the absence of the inhibitor or agent (e.g. compound, drug, antagonist). Thus, inhibition includes, at least in part, partially or totally blocking stimulation, decreasing, preventing, or delaying activation, or inactivating, desensitizing, or down-regulating signal transduction or enzymatic activity. In some embodiments, an "inhibitor" may be a compound that inhibits DNA replication or induces cell death, e.g., by binding, partially or totally blocking stimulation, decrease, prevent, or delay activation, or inactivate, desensitize, or down-regulate signal transduction or enzymatic activity necessary for DNA replication, cell viability, or cell survival.

As defined herein, the term "activation", "activate", "activating", "increase", "increasing" and the like in reference to a target-agent (e.g. compound, drug, agonist) or protein-agonist interaction means positively affecting (e.g. increasing) the activity or function of the target or protein relative to the activity or function of the target or protein in the absence of the activator or agent (e.g. compound, drug, agonist, or dabuzalgron, or an analog, pharmaceutically acceptable salt, or prodrug thereof). Thus, activation includes, at least in part, partially or totally increasing stimulation, increasing, enabling, or accelerating activation, or activating, sensitizing, or up-regulating signal transduction or enzymatic activity. In some embodiments, an "activator" may be a compound that increases DNA replication or reduces cell death, e.g., by binding, partially or totally increasing stimulation, increase, enable, or accelerate activation, or activate, sensitize, or up-regulate signal transduction or enzymatic activity necessary for DNA replication, cell viability, or cell survival. In embodiments, an activator is dabuzalgron. In embodiments, an activator is dabuzalgron or an analog, derivative, or prodrug thereof.

"Patient" or "subject in need thereof" refers to a living organism suffering from or prone to a condition that can be treated by administration of an agent (e.g. compound, drug, antagonist, agonist, or dabuzalgron, or an analog, pharmaceutically acceptable salt, or prodrug thereof) or pharmaceutical composition as provided herein. Non-limiting examples include humans, other mammals (e.g. mice, rats, dogs, monkeys, cows, goats, sheep, rabbits) and other non-mammalian animals. In some embodiments, a patient or subject in need thereof is a human with a disease or condition (e.g. heart muscle damage, cardiomyopathy, cardiotoxicity, or heart failure).

"Disease" or "condition" refer to a state of being or health status of a patient or subject capable of being treated with the compounds or methods provided herein. In some embodiments, the disease is a disease related to (e.g. caused by) heart muscle damage (e.g. cardiomyopathy, cardiotoxicity, heart failure). In some instances, "disease" or "condition" refers to cardiomyopathy, cardiotoxicity, heart failure, or cardiovascular disease. In some embodiments, the disease is heart muscle damage. In some embodiments, the disease is heart failure. In some embodiments, the disease is cardiomyopathy. In some embodiments, the disease is cardiotoxicity. In some embodiments, the disease is cardiotoxicity associated with anticancer agent administration to the subject. In some embodiments, the disease is cardiotoxicity associated with anthracycline administration to the subject. In some embodiments, the disease is cardiotoxicity associated with doxorubicin administration to the subject. In some embodiments, the disease is hypertrophic cardiomyopathy. In some embodiments, the disease is restrictive cardiomyopathy. In some embodiments, the disease is dilated cardiomyopathy. In some embodiments, the disease is dilated cardiomyopathy. In some embodiments, the disease is dilated congestive cardiomyopathy. In some embodiments, the disease is congestive cardiomyopathy. In some embodiments, the disease is cardiomyopathy associated with or caused by hypertension, heart valve disease, myocardial ischemia, myocardial inflammation, myocardial infarction, heart failure, pulmonary hypertension, myocardial stunning, myocardial hibernation, cardiac surgery, pressure overload-induced cardiac hypertrophy, or coronary intervention. In some embodiments, the disease is heart failure associated with or caused by cardiomyopathy. In some embodiments, the disease is heart failure associated with or caused by cardiomyopathy (e.g. associated with or caused by hypertension, heart valve disease, myocardial ischemia, myocardial inflammation, myocardial infarction, pulmonary hypertension, myocardial stunning, myocardial hibernation, cardiac surgery, pressure overload-induced cardiac hypertrophy, or coronary intervention). In some embodiments, the disease is heart failure associated with or caused by idiopathic cardiomyopathy. In some embodiments, the disease is a cardiovascular disease. In some embodiments, the disease is cardiomyopathy associated with or caused by hypertension, heart valve disease, myocardial ischemia, myocardial inflammation, heart failure, pulmonary hypertension, myocardial stunning, myocardial hibernation, cardiac surgery, pressure overload-induced cardiac hypertrophy, or coronary intervention. In some embodiments, the disease is heart failure associated with or caused by cardiomyopathy (e.g. associated with or caused by hypertension, heart valve disease, myocardial ischemia, myocardial inflammation, pulmonary hypertension, myocardial stunning, myocardial hibernation, cardiac surgery, pressure overload-induced cardiac hypertrophy, or coronary intervention). In some embodiments, the disease is cardiomyopathy associated with or caused by hypertension, heart valve disease, myocardial inflammation, heart failure, pulmonary hypertension, myocardial stunning, myocardial hibernation, cardiac surgery, pressure overload-induced cardiac hypertrophy, or coronary intervention. In some embodiments, the disease is heart failure associated with or caused by cardiomyopathy (e.g. associated with or caused by hypertension, heart valve disease, myocardial inflammation, pulmonary hypertension, myocardial stunning, myocardial hibernation, cardiac surgery, pressure overload-induced cardiac hypertrophy, or coronary intervention). In embodiments, the disease is not cardiomyopathy associated with or caused by myocardial infarction. In some embodiments, the disease is not heart failure associated with or caused by cardiomyopathy associated with or caused by myocardial infarction. In embodiments, the disease is not cardiomyopathy associated with or caused by myocardial ischemia. In some embodiments, the disease is not heart failure associated with or caused by cardiomyopathy associated with or caused by myocardial ischemia.

As used herein, the term "cardiovascular disease" refers to a disease or condition affecting the circulatory system, including the heart and blood vessels. In embodiments, cardiovascular disease includes diseases caused by or exacerbated by atherosclerosis. Exemplary cardiovascular diseases that may be treated with a compound or method provided herein include heart muscle damage, alcoholic cardiomyopathy, cardiomyopathy, cardiotoxicity, cardiomyopathy associated with anthracycline administration, cardiotoxicity associated with anthracycline administration, cardiotoxicity associated with doxorubicin administration, cardiomyopathy associated with doxorubicin administration, cardiomyopathy associated with anticancer agent administration, cardiotoxicity associated with anticancer agent administration, coronary artery disease, congenital heart disease, arrhythmogenic right ventricular cardiomyopathy, restrictive cardiomyopathy, noncompaction cardiomyopathy, diabetes mellitus, hypertension, hyperhomocysteinemia, hypercholesterolemia, atherosclerosis, ischemic heart disease, heart failure, cor pulmonale, hypertensive heart disease, left ventricular hypertrophy, coronary heart disease, (congestive) heart failure, hypertensive cardiomyopathy, cardiac arrhythmias, inflammatory heart disease, endocarditis, inflammatory cardiomegaly, myocarditis, valvular heart disease, stroke, hypertension, heart valve disease, myocardial ischemia, myocardial inflammation, heart failure, pulmonary hypertension, myocardial stunning, myocardial hibernation, cardiomyopathy associated with cardiac surgery, cardiomyopathy associated with coronary intervention or myocardial infarction, cardiomyopathy caused by genetic changes in cardiac proteins, cardiomyopathy associated with genetic mutations in one or more cardiac proteins, cardiomyopathy associated with aberrant expression or function of one or more cardiac proteins.

Exemplary cardiovascular diseases that may be treated with a compound or method provided herein include heart muscle damage, alcoholic cardiomyopathy, cardiomyopathy, cardiotoxicity, cardiomyopathy associated with anthracycline administration, cardiotoxicity associated with anthracycline administration, cardiotoxicity associated with doxorubicin administration, cardiomyopathy associated with doxorubicin administration, cardiomyopathy associated with anticancer agent administration, cardiotoxicity associated with anticancer agent administration, coronary artery disease, congenital heart disease, arrhythmogenic right ventricular cardiomyopathy, restrictive cardiomyopathy, noncompaction cardiomyopathy, diabetes mellitus, hypertension, hyperhomocysteinemia, hypercholesterolemia, atherosclerosis, ischemic heart disease, heart failure, cor pulmonale, hypertensive heart disease, left ventricular hypertrophy, coronary heart disease, (congestive) heart failure, hypertensive cardiomyopathy, cardiac arrhythmias, inflammatory heart disease, endocarditis, inflammatory cardiomegaly, myocarditis, valvular heart disease, stroke, hypertension, heart valve disease, myocardial ischemia, myocardial inflammation, heart failure, pulmonary hypertension, myocardial stunning, myocardial hibernation, cardiomyopathy associated with cardiac surgery, cardiomyopathy associated with coronary intervention or myocardial infarction, cardiomyopathy caused by genetic changes in cardiac proteins, cardiomyopathy associated with genetic mutations in one or more cardiac proteins, cardiomyopathy associated with aberrant expression or function of one or more cardiac proteins.

Exemplary cardiovascular diseases that may be treated with a compound or method provided herein include heart muscle damage, alcoholic cardiomyopathy, coronary artery disease, congenital heart disease, arrhythmogenic right ventricular cardiomyopathy, restrictive cardiomyopathy, noncompaction cardiomyopathy, diabetes mellitus, hypertension, hyperhomocysteinemia, hypercholesterolemia, atherosclerosis, heart failure, cor pulmonale, hypertensive heart disease, left ventricular hypertrophy, coronary heart disease, (congestive) heart failure, hypertensive cardiomyopathy, cardiac arrhythmias, inflammatory heart disease, endocarditis, inflammatory cardiomegaly, myocarditis, valvular heart disease, stroke, hypertension, heart valve disease, myocardial inflammation, heart failure, pulmonary hypertension, myocardial stunning, myocardial hibernation, cardiomyopathy associated with cardiac surgery, cardiomyopathy associated with coronary intervention, cardiomyopathy caused by genetic changes in cardiac proteins, cardiomyopathy associated with genetic mutations in one or more cardiac proteins, cardiomyopathy associated with aberrant expression or function of one or more cardiac proteins. In some embodiments, treating a cardiovascular disease includes treating a condition or symptom caused by a cardiovascular disease. A non-limiting example of such a treatment is treating complications due to a myocardial infarction, after the myocardial infarction has occurred. In some embodiments, a cardiovascular disease is cardiomyopathy. In some embodiments, cardiomyopathy is caused by another disease (e.g. a cardiovascular disease) and treatment of cardiomyopathy includes treating the causative disease (e.g. cardiovascular disease) of the cardiomyopathy. In some embodiments, the cardiomyopathy is dilated cardiomyopathy. In some embodiments, the cardiomyopathy is hypertrophic cardiomyopathy. In some embodiments, the cardiomyopathy is hypertrophic, restrictive, or dilated. In embodiments, cardiovascular disease does not include myocardial infarction. In embodiments, treating cardiovascular disease does not include treating a condition or symptom associated with or caused by myocardial infarction (e.g. after the myocardial infarction has occurred). In embodiments, cardiovascular disease does not include myocardial ischemia. In embodiments, treating cardiovascular disease does not include treating a condition or symptom associated with or caused by myocardial ischemia (e.g. after the myocardial ischemia has occurred). In embodiments, cardiovascular disease does not include ischemic heart disease. In embodiments, cardiovascular disease is cardiomyopathy. In embodiments, cardiovascular disease is cardiotoxicity. In embodiments, cardiovascular disease is cardiomyopathy associated with anthracycline administration. In embodiments, cardiovascular disease is cardiotoxicity associated with anthracycline administration. In embodiments, cardiovascular disease is cardiotoxicity associated with doxorubicin administration. In embodiments, cardiovascular disease is cardiomyopathy associated with doxorubicin administration. In embodiments, cardiovascular disease is cardiomyopathy associated with anticancer agent administration. In embodiments, cardiovascular disease is cardiotoxicity associated with anticancer agent administration.

As used herein, the term "cardiomyopathy" refers to a disease or condition affecting the heart, wherein a heart muscle (e.g., cell of the heart muscle) is damaged or the function of a heart muscle (e.g., cell of the heart muscle) is impaired (e.g., relative to a healthy fully functioning heart, heart muscle, of heart muscle cell. Exemplary cardiomyopathy that may be treated with a compound or method provided herein include heart muscle damage, alcoholic cardiomyopathy, arrhythmogenic right ventricular cardiomyopathy, restrictive cardiomyopathy, noncompaction cardiomyopathy, heart failure, (congestive) heart failure, hypertensive cardiomyopathy, cardiomyopathy associated with cardiac surgery, cardiomyopathy associated with coronary intervention or myocardial infarction, cardiomyopathy caused by genetic changes in cardiac proteins, cardiomyopathy associated with genetic mutations in one or more cardiac proteins, cardiomyopathy associated with aberrant expression or function of one or more cardiac proteins, and cardiomyopathy associated with anthracycline (e.g., doxocycline) treatment. In some embodiments, treating a cardiomyopathy includes treating a condition or symptom caused by a cardiomyopathy. In some embodiments, cardiomyopathy is caused by another disease (e.g., a cardiovascular disease) and treatment of cardiomyopathy includes treating the causative disease (e.g. cardiovascular disease) of the cardiomyopathy. In some embodiments, the cardiomyopathy is dilated cardiomyopathy. In some embodiments, the cardiomyopathy is hypertrophic cardiomyopathy. In some embodiments, the cardiomyopathy is hypertrophic, restrictive, or dilated.

As used herein, the term "cardiotoxicity" refers to a disease or condition affecting the heart, wherein a heart muscle (e.g., cell of the heart muscle) is damaged or the function of a heart muscle (e.g., cell of the heart muscle) is impaired (e.g., relative to a healthy fully functioning heart, heart muscle, of heart muscle cell), by a toxic agent (e.g., exogenous toxic agent, anthracycline, doxorubicin, agent administered to the subject, administered systemically, administered to the heart, administered locally, administered to a subject for treating another disease (e.g., cancer)). In embodiments, cardiotoxicity includes cardiomyopathy, heart muscle damage, alcoholic cardiomyopathy, arrhythmogenic right ventricular cardiomyopathy, restrictive cardiomyopathy, noncompaction cardiomyopathy, heart failure, (congestive) heart failure, hypertensive cardiomyopathy, cardiomyopathy associated with cardiac surgery, cardiomyopathy associated with coronary intervention or myocardial infarction, cardiomyopathy caused by genetic changes in cardiac proteins, cardiomyopathy associated with genetic mutations in one or more cardiac proteins, cardiotoxicity associated with anthracycline (e.g., doxocycline) treatment, and cardiomyopathy associated with anthracycline (e.g., doxocycline) treatment; all associated with administration of an agent toxic to the heart, heart tissue, heart muscle, or a heart cell. In some embodiments, treating a cardiotoxicity includes treating a condition or symptom caused by a cardiotoxicity. In embodiments, cardiotoxicity includes atrial arrhythmia. In embodiments, cardiotoxicity includes ventricular arrhythmia. In embodiments, cardiotoxicity includes conduction system abnormalities. In embodiments, cardiotoxicity includes prolongation of the QT interval.

As used herein, the term "disease-related cells" means cells that are associated with a disease or condition, which include but are not limited to cells that initiate a disease, cells that propogate a disease, cells that cause a disease, cells that cause one or more symptoms of a disease, cells that are a hallmark of a disease; cells that contain a particular protein or mRNA molecule that causes a symptom of the disease. In some embodiments, the disease is cardiotoxicity or cardiomyopathy and disease-related cells include heart muscle cells, cardiac muscle cells, or cardiomyocytes.

The term "expression" refers to a gene that is transcribed or translated at a detectable level. As used herein, expression also encompasses "overexpression," which refers to a gene that is transcribed or translated at a detectably greater level, usually in a disease-related cell, in comparison to a normal cell. Expression can be detected using conventional techniques for detecting protein (e.g., ELISA, Western blotting, flow cytometry, immunofluorescence, immunohistochemistry, etc.) or mRNA (e.g., RT-PCR, PCR, hybridization, etc.).

As used herein, the term "marker" refers to any biochemical marker, serological marker, genetic marker, or other clinical or echographic characteristic that can be used to diagnose or provide a prognosis for a disease (e.g., cardiomyopathy, cardiovascular disease).

The term "sample" includes sections of tissues such as biopsy and autopsy samples, and frozen sections taken for histological purposes. Such samples include blood and blood fractions or products (e.g., serum, plasma, platelets, red blood cells, and the like), sputum, tissue, cultured cells (e.g., primary cultures, explants, and transformed cells), stool, urine, other biological fluids (e.g., prostatic fluid, gastric fluid, intestinal fluid, renal fluid, lung fluid, cerebrospinal fluid, and the like), etc. A sample is typically obtained from a "subject" such as a eukaryotic organism, most preferably a mammal such as a primate, e.g., chimpanzee or human; cow; dog; cat; a rodent, e.g., guinea pig, rat, mouse; rabbit; or a bird; reptile; or fish. In some embodiments, the sample is obtained from a human.

A "biopsy" refers to the process of removing a tissue sample for diagnostic or prognostic evaluation, and to the tissue specimen itself. Any biopsy technique known in the art can be applied to the diagnostic and prognostic methods of the present invention (e.g. muscle biopsy or heart biopsy). The biopsy technique applied will depend on the tissue type to be evaluated (e.g., heart, muscle, etc.), among other factors. Representative biopsy techniques include, but are not limited to, excisional biopsy, incisional biopsy, needle biopsy, and surgical biopsy. A diagnosis or prognosis made by endoscopy or fluoroscopy can require a "core-needle biopsy", or a "fine-needle aspiration biopsy" which generally obtains a suspension of cells. Biopsy techniques are discussed, for example, in *Harrison's Principles of Internal Medicine*, Kasper, et al., eds., 16th ed., 2005, Chapter 70, and throughout Part V.

As used herein, the term "administering" means oral administration, parenteral administration, administration as a suppository, topical contact, intravenous, intraperitoneal, intramuscular, intralesional, intrathecal, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc. By "co-administer" it is meant that a composition described herein is administered at the same time, just prior to, or just after the administration of one or more additional therapies, for example additional agents (e.g. compounds, drugs, inhibitors, antagonists, agonists) useful in the treatment of cardiomyopathy or cardiotoxicity or agents useful in the treatment of one or more other symptoms of a cardiomyopathy associated disease or cardiotoxicity associated disease. The agents (e.g. compounds, drugs, agonists, or dabuzalgron, or an analog, pharmaceutically acceptable salt, or prodrug thereof) of the invention can be administered alone or can be coadministered to the patient. Coadministration is meant to include simultaneous or sequential administration of the agents (e.g. compounds, drugs, agonists, or dabuzalgron, or an analog, pharmaceutically acceptable salt, or prodrug thereof) individually or in combination (more than one agent (e.g. compound, drug, agonist)). Thus, the preparations can also be combined, when desired, with other active substances (e.g., to reduce metabolic degradation). The compositions of the present invention can be delivered transdermally, by a topical route, formulated as applicator sticks, solutions, suspensions, emulsions, gels, creams, ointments, pastes, jellies, paints, powders, and aerosols.

"Analog" is used in accordance with its plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof. Accordingly, an analog is a compound that is similar or comparable in function and appearance but not in structure or origin to a reference compound. In some embodiments, a reference compound is dabuzalgron. In embodiments, a dabuzalgron analog is a compound similar, but not identical in structure to dabuzalgron, having similar (e.g., identical) function on cardiomyopathy or cardiotoxicity or a symptom of cardiomyopathy or a symptom of cardiotoxicity.

The term "dabuzalgron" refers to N-[6-chloro-3-(4,5-dihydro-1H-imidazol-2-ylmethoxy)-2-methylphenyl]methanesulfonamide, or any salt form thereof (e.g. N-[6-chloro-3-(4,5-dihydro-1H-imidazol-2-ylmethoxy)-2-methylphenyl]methanesulfonamide hydrobromide), or any isomer thereof. Dabuzalgron has also been shown to be a potent and a more selective α1A AR agonist than the non-selective α1AR agonist phenylephrine. Dabuzalgron has also been shown to be a potent and a more selective α1A AR agonist than the non-selective α1AR agonists phenylephrine, methoxamine, and midodrine. In embodiments, dabuzalgron is N-[6-chloro-3-(4,5-dihydro-1H-imidazol-2-ylmethoxy)-2-methylphenyl]methanesulfonamide. Dabuzalgron is a partial agonist at the alpha-1A-adrenergic receptor. In embodiments, dabuzalgron is a salt form of N-[6-chloro-3-(4,5-dihydro-1H-imidazol-2-ylmethoxy)-2-methylphenyl]methanesulfonamide. In embodiments, dabuzalgron is N-[6-chloro-3-(4,5-dihydro-1H-imidazol-2-ylmethoxy)-2-methylphenyl]methanesulfonamide hydrobromide.

"Blood Pressure" is the pressure of the blood against the walls of the arteries when the heart contracts (systolic pressure) and when the heart is at rest (diastolic pressure). In some embodiments, hypertensive blood pressure may be considered systolic pressure of about 140 mmHg or higher and/or diastolic pressure of about 90 mmHg or higher. In some embodiments, hypertensive blood pressure may be considered systolic pressure of 140 mmHg or higher and/or diastolic pressure of 90 mmHg or higher. "Undesirable blood pressure" or "unhealthy blood pressure" or "high blood pressure" are interchangeable terms and refer to blood pressure levels that are above normal or above healthy blood pressure levels (e.g. hypertensive blood pressure). In some embodiments, high blood pressure is/can be determined by a person of ordinary skill in the art (e.g. doctor, cardiologist, internist, medical doctor). In some embodiments, a high blood pressure is hypertensive blood pressure. In some embodiments, a high blood pressure is 140/90 mmHg or higher. In some embodiments, a high blood pressure or undesirable blood pressure or unhealthy blood pressure is a blood pressure greater than the desirable blood pressure range recommended by the American Heart Association. In some embodiments, a high blood pressure or undesirable blood pressure or unhealthy blood pressure is a blood pressure categorized as hypertensive or pre-hypertensive by the American Heart Association.

In some aspects, the terms "associated" or "associated with" is used herein to describe a first disease in relation to a medical event, a biological compound or a second disease (e.g. a protein associated disease, a cardiomyopathy associated with another disease). Where used to describe a first disease in relation to such a medical event, a biological compound or a second disease, the terms "associated" or "associated with" means that the first disease (e.g., cardiomyopathy) results from, is correlated with, is caused by, or is a symptom of the medical event, biological compound or a second disease (e.g., cardiotoxicity). For example, cardiomyopathy associated with hypertension may be a cardiomyopathy that results (entirely or partially) from hypertension or cardiomyopathy wherein a particular symptom of the disease is caused (entirely or partially) by hypertension. For example, cardiomyopathy associated with anticancer agent administration (e.g., anthracycline) may be a cardiomyopathy that results (entirely or partially) from anticancer agent administration (e.g., anthracycline) or cardiomyopathy wherein a particular symptom of the disease is caused (entirely or partially) by anticancer agent administration (e.g., anthracycline). For example, cardiotoxicity associated with anticancer agent administration (e.g., anthracycline) may be a cardiotoxicity that results (entirely or partially) from anticancer agent administration (e.g., anthracycline) or cardiotoxicity wherein a particular symptom of the disease is caused (entirely or partially) by anticancer agent administration (e.g., anthracycline). For example, heart failure associated with heart damage (heart muscle damage) may be heart failure that results (entirely or partially) from heart damage (e.g. heart muscle damage) wherein a particular symptom of the disease is caused (entirely or partially) by heart damage (e.g. heart muscle damage). For example, heart failure associated with cardiomyopathy may be heart failure that results (entirely or partially) from cardiomyopathy wherein a particular symptom of the disease is caused (entirely or partially) by cardiomyopathy. For example, heart failure associated with cardiotoxicity may be heart failure that results (entirely or partially) from cardiotoxicity wherein a particular symptom of the disease is caused (entirely or partially) by cardiotoxicity. As used herein, what is described as being associated with a disease, if a causative agent, could be a target for treatment of the disease. For example, heart failure associated with cardiomyopathy or a cardiomyopathy associated heart failure, may be treated with dabuzalgron, in the instance where cardiomyopathy causes the heart failure. For example, cardiomyopathy associated with hypertension may be cardiomyopathy that a subject with hypertension is at higher risk of developing as compared to a subject without hypertension. In some embodiments, where the first disease is "associated" or "associated with" the medical event, biological compound or a second disease, the first disease (or symptom thereof) is caused by the medical event, biological compound or a second disease.

The term "aberrant" as used herein refers to different from normal. When used to described enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g., by administering a compound or using a method as described herein), results in reduction of the disease or one or more disease symptoms.

Cardiomyopathy is a disease of the heart muscle, which may be characterized by heart cell dysfunction or heart muscle dysfunction. This form of heart disease is often distinctive, both in general symptoms and in patterns of blood flow, to allow a diagnosis to be made. Increasing recognition of this disease, along with improved diagnostic techniques, has shown that cardiomyopathy is the major cause of heart failure, which has high morbidity and mortality. Cardiomyopathy can result from a variety of structural or functional abnormalities of the ventricular myocardium. There are three clinical classifications of cardiomyopathy: hypertrophic, restrictive, and dilated congestive. Dilated cardiomyopathy is a disorder of myocardial function where impaired systolic dysfunction and ventricular dilation occur, classified as ischemic or non-ischemic (e.g., toxic, genetic, idiopathic, etc.). Restrictive cardiomyopathy is a rare form that occurs as a consequence of the ventricular walls becoming rigid so that the chambers are unable to fill adequately, caused for example by infiltration with amyloid or some other foreign material. Hypertrophic cardiomyopathy is characterized by ventricular hypertrophy and may be congenital or acquired, commonly caused by hypertension. The prognosis for all three types of disease is guarded at best and often poor. Current treatment of cardiomyopathy involves beta-blockers, angiotensin converting enzyme inhibitors, use of anti-coagulants, and cardiac transplantation. When cardiomyopathy is sufficiently advanced, it causes congestive heart failure, with physiological symptoms including breathlessness with exertion or even at rest, swelling of the legs, ankles and feet, bloating (distention) of the abdomen with fluid, fatigue, irregular heartbeats, and dizziness, light-headedness and fainting.

The α1 adrenergic receptors (α1-ARs) are important mediators of sympathetic nervous system responses, particularly those involved in cardiovascular homeostasis, such as arteriolar smooth muscle constriction and cardiac contraction. In addition, α1-ARs have more recently been implicated in cardiac hypertrophy, cardio-protection, and in ischemic preconditioning. α1-ARs are activated by the catecholamines, norepinephrine and epinephrine.

The α1 adrenergic receptors are members of the superfamily of G protein-coupled receptors and mediate effects related to the regulation of cellular growth and function (Shibata et al. 2003, J. Bio. Chem. 278:672-678). α1-ARs consist of three subtypes: α1 A-, α1 B-, and α1 D-ARs Graham et al., 1996. Circ. Res. 78:737-749). The three different α1-AR subtypes are expressed in different tissues and various cell types. As a result, studies on the physiological effects mediated by each of the α1-ARs in individual tissues are complicated by the co-existence of multiple α1-AR subtypes (Minneman et al. 1994, Mol. Pharmacal. 46:929-936; Minneman and Esbenshade, 1994. Annu. Rev. Pharmacal. Toxicol., 34:117-133; Weinberg et. al, 1994; Biochem. Bio-phys Res. Commun. 201:1296-1304; Esbenshade et al. 1995; Mol. Pharmacal. 47:977-985; Shibata et al. 1995; Mol. Pharmacal. 48:250-258). Alpha-1-adrenergic receptor agonists are shown herein to be useful in the treatment and prevention of heart and brain diseases. Furthermore, alpha-1-adrenergic receptor agonists (e.g. dabuzalgron, or an analog, pharmaceutically acceptable salt, or prodrug thereof) are notable for increasing beneficial processes at both functional levels, for example cardiac contraction, and at trophic/protective levels, for example preventing cell death and repairing injury. In some embodiments, the present invention includes the use of alpha-1-adrenergic agonists at doses that are below those that have an effect on smooth muscle contraction.

The terms "Mitogen-activated protein kinase" and "MAPK" and "extracellular signal-regulated kinases" and "ERK" refer to a protein (including homologs, isoforms, and functional fragments thereof) with kinase activity in the MAP Kinase signaling pathway. The term includes any recombinant or naturally-occurring form of MAPK or variants thereof that maintain MAP Kinase activity (e.g. within at least 30%, 40%, 50%, 60%, 70%, 80%, 90%, 95%, or 100% activity compared to wildtype MAP Kinase). In embodiments, the MAP Kinase protein encoded by the MAPK gene has the amino acid sequence set forth in or corresponding to Entrez 5594, UniProt P28482, or RefSeq (protein) NP_002736 of MAPK1 or ERK2. In embodiments, the MAP Kinase gene has the nucleic acid sequence set forth in RefSeq (mRNA) NM_002745 (MAPK1 or ERK2). In embodiments, the amino acid sequence or nucleic acid sequence is the sequence known at the time of filing of the present application. In embodiments, the sequence corresponds to NP_002736.3 (MAPK1 or ERK2). In embodiments, the sequence corresponds to NM_002745.4 (MAPK1 or ERK2). In embodiments, the MAP Kinase is a human MAP Kinase, such as a human cancer causing MAP Kinase. In embodiments, the MAP Kinase protein encoded by the MAPK gene has the amino acid sequence set forth in or corresponding to Entrez 5595, UniProt P27361, or RefSeq (protein) NP_002737 of MAPK3 or ERK1. In embodiments, the MAP Kinase gene has the nucleic acid sequence set forth in RefSeq (mRNA) NM_002746 (MAPK3 or ERK1). In embodiments, the amino acid sequence or nucleic acid sequence is the sequence known at the time of filing of the present application. In embodiments, the sequence corresponds to NP_002737.2 (MAPK3 or ERK1). In embodiments, the sequence corresponds to NM_002746.2 (MAPK3 or ERK1). In embodiments, the MAP Kinase is a human MAP Kinase, such as a human cancer causing MAP Kinase.

In embodiments "ERK" refers to an ERK2. In embodiments "ERK" refers to an ERK1. In embodiments "ERK" refers to both ERK1/2.

The terms "alpha-1A adrenergic receptor" and "α1A" and "α1A-AR" and "ADRA1A" refer to a protein (including homologs, isoforms, and functional fragments thereof) with activity in the alpha-1A adrenergic receptor signaling pathway. The term includes any recombinant or naturally-occurring form of α1A-AR or variants thereof that maintain α1A-AR activity (e.g. within at least 30%, 40%, 50%, 60%, 70%, 80%, 90%, 95%, or 100% activity compared to wildtype α1A-AR). In embodiments, the α1A-AR protein encoded by the α1A-AR gene has the amino acid sequence set forth in or corresponding to Entrez 148, UniProt P35348, or RefSeq (protein) NP_000671. In embodiments, the α1A-AR gene has the nucleic acid sequence set forth in RefSeq (mRNA) NM_000680. In embodiments, the amino acid sequence or nucleic acid sequence is the sequence known at the time of filing of the present application. In embodiments, the sequence corresponds to NP_000671.2. In embodiments, the sequence corresponds to NM_000680.3. In embodiments, the α1A-AR protein encoded by the α1A-AR gene has the amino acid sequence set forth in or corresponding to Entrez 148, UniProt P35348, or RefSeq (protein) NP_150645. In embodiments, the α1A-AR gene has the nucleic acid sequence set forth in RefSeq (mRNA) NM_033302. In embodiments, the amino acid sequence or nucleic acid sequence is the sequence known at the time of filing of the present application. In embodiments, the sequence corresponds to NP_150645.2. In embodiments, the sequence corresponds to NM_033302.3.

II. Methods of Treatment

In a first aspect is provided a method of treating or preventing cardiomyopathy in a subject in need of such treatment, the method including administering a therapeutically or prophylactically effective amount of dabuzalgron, or an analog, pharmaceutically acceptable salt, or prodrug thereof. In embodiments, the method includes administering dabuzalgron.

In a another aspect is provided a method of treating or preventing cardiomyopathy in a subject in need of such treatment, the method including administering a therapeutically or prophylactically effective amount of dabuzalgron.

In embodiments of the method, the cardiomyopathy is dilated cardiomyopathy. In embodiments of the method, the cardiomyopathy is hypertrophic cardiomyopathy. In embodiments of the method, the cardiomyopathy is associated with hypertension, heart valve disease, myocardial ischemia, myocardial inflammation, myocardial infarction, heart failure, pulmonary hypertension, myocardial stunning, myocardial hibernation, cardiac surgery, pressure overload-induced cardiac hypertrophy, or coronary intervention. In embodiments, the method includes treating the cardiomyopathy. In some embodiments, the method includes preventing the cardiomyopathy. In some embodiments, the method does not include preventing the cardiomyopathy. In embodiments, the method includes cardiomyopathy associated with anthracycline treatment. In embodiments, the cardiomyopathy is associated with anthracycline treatment. In some embodiments, the cardiomyopathy is associated with doxorubicin treatment. In embodiments, the cardiomyopathy is associated with chemotherapy treatment. In embodiments, the cardiomyopathy is idiopathic cardiomyopathy. In embodiments, the cardiomyopathy is associated with myocardial infarction. In embodiments, the cardiomyopathy is associated with hypertension, heart valve disease, myocardial ischemia, myocardial inflammation, heart failure, pulmonary hypertension, myocardial stunning, myocardial hibernation, cardiac surgery, pressure overload-induced cardiac hypertrophy, or coronary intervention. In embodiments, the cardiomyopathy is associated with myocardial ischemia. In embodiments, the cardiomyopathy is associated with hypertension, heart valve disease, myocardial inflammation, heart failure, pulmonary hypertension, myocardial stunning, myocardial hibernation, cardiac surgery, pressure overload-induced cardiac hypertrophy, or coronary intervention. In embodiments, the method includes treating or preventing cardiomyopathy in a patient undergoing treatment with an anthracycline (e.g. doxorubicin, daunorubicin, epirubicin, idarubicin, adriamycin, or valrubicin). In embodiments, the cardiomyopathy is associated with (e.g., caused by) cardiotoxicity. In embodiments, the method includes treating cardiomyopathy in a patient undergoing treatment with an anthracycline (e.g. doxorubicin, daunorubicin, epirubicin, idarubicin, adriamycin, or valrubicin). In embodiments, the method includes preventing cardiomyopathy in a patient undergoing treatment with an anthracycline (e.g., doxorubicin, daunorubicin, epirubicin, idarubicin, adriamycin, or valrubicin). In embodiments, the method includes preventing the anthracycline-induced cardiomyopathy. In embodiments, the method includes treating but not preventing cardiomyopathy. In embodiments, the method includes treating but not preventing anthracycline-induced cardiomyopathy. In embodiments, the method includes preventing cardiomyopathy in a patient. In embodiments, the method includes administering dabuzalgron.

In another aspect is provided a method of treating or preventing heart failure in a subject in need of such treatment, the method including administering a therapeutically or prophylactically effective amount of dabuzalgron, or an analog, pharmaceutically acceptable salt, or prodrug thereof. In some embodiments, the method includes improving (e.g. increasing) heart contraction. In embodiments, the method includes improving (e.g., increasing) cardiogenesis. In embodiments, the method is treating heart failure in a subject in need of such treatment. In embodiments, the method is preventing heart failure in a subject in need of such treatment. In embodiments, the method is treating but not preventing heart failure in a subject in need of such treatment. In embodiments, the method includes administering dabuzalgron.

In another aspect is provided a method of improving heart contraction in a subject in need of such treatment, the method including administering a therapeutically effective amount of dabuzalgron, or an analog, pharmaceutically acceptable salt, or prodrug thereof. In some embodiments, improving heart contraction treats heart failure. In embodiments, improving heart contraction includes improving the volume of the heart contraction, improving strength of the heart contraction, or improving length of the contraction. In embodiments, the method includes administering dabuzalgron.

In another aspect is provided a method of treating or preventing cardiotoxicity in a subject in need of such treatment, the method including administering a therapeutically or prophylactically effective amount of dabuzalgron, or an analog, pharmaceutically acceptable salt, or prodrug thereof. In embodiments, the method includes administering dabuzalgron.

In embodiments, the method includes treating the cardiotoxicity. In some embodiments, the method includes preventing the cardiotoxicity. In some embodiments, the method does not include preventing the cardiotoxicity. In embodiments, the method includes cardiotoxicity associated with anthracycline treatment. In embodiments, the cardiotoxicity is associated with anthracycline treatment. In some embodiments, the cardiotoxicity is associated with doxorubicin treatment. In embodiments, the cardiotoxicity is associated with chemotherapy treatment. In embodiments, the cardiotoxicity is idiopathic cardiotoxicity. In embodiments, the method includes treating or preventing cardiotoxicity in a subject undergoing treatment with an anthracycline (e.g., doxorubicin, daunorubicin, epirubicin, idarubicin, adriamycin, or valrubicin). In embodiments, treating a cardiotoxicity includes treating a condition or symptom induced by a cardiotoxicity. In embodiments, cardiotoxicity includes atrial arrhythmia. In embodiments, cardiotoxicity includes ventricular arrhythmia. In embodiments, cardiotoxicity includes conduction system abnormalities. In embodiments, cardiotoxicity includes prolongation of the QT interval. In embodiments, the method includes treating cardiotoxicity in a patient undergoing treatment with an anthracycline (e.g., doxorubicin, daunorubicin, epirubicin, idarubicin, adriamycin, or valrubicin). In embodiments, the method includes preventing cardiotoxicity in a patient undergoing treatment with an anthracycline (e.g., doxorubicin, daunorubicin, epirubicin, idarubicin, adriamycin, or valrubicin). In embodiments, the method includes administering dabuzalgron.

In some embodiments of the methods, the subject's blood pressure does not increase as a result of the administration. In some embodiments of the methods, the subject's blood pressure increases by an amount equal to or less than 50, 40, 30, 20, 10, 9, 8, 7, 6, 5, 4, 3, 2, or 1 mmHg as a result of the administration. In some embodiments of the methods, the subject's blood pressure increases by an amount equal to or less than 50 mmHg as a result of the administration. In some embodiments of the methods, the subject's blood pressure increases by an amount equal to or less than 40 mmHg as a result of the administration. In some embodiments of the methods, the subject's blood pressure increases by an amount equal to or less than 30 mmHg as a result of the administration. In some embodiments of the methods, the subject's blood pressure increases by an amount equal to or less than 20 mmHg as a result of the administration. In some embodiments of the methods, the subject's blood pressure increases by an amount equal to or less than 10 mmHg as a result of the administration. In some embodiments of the methods, the subject's blood pressure increases by an amount equal to or less than 9 mmHg as a result of the administration. In some embodiments of the methods, the subject's blood pressure increases by an amount equal to or less than 8 mmHg as a result of the administration. In some embodiments of the methods, the subject's blood pressure increases by an amount equal to or less than 7 mmHg as a result of the administration. In some embodiments of the methods, the subject's blood pressure increases by an amount equal to or less than 6 mmHg as a result of the administration. In some embodiments of the methods, the subject's blood pressure increases by an amount equal to or less than 5 mmHg as a result of the administration. In some embodiments of the methods, the subject's blood pressure increases by an amount equal to or less than 4 mmHg as a result of the administration. In some embodiments of the methods, the subject's blood pressure increases by an amount equal to or less than 3 mmHg as a result of the administration. In some embodiments of the methods, the subject's blood pressure increases by an amount equal to or less than 2 mmHg as a result of the administration. In some embodiments of the methods, the subject's blood pressure increases by an amount equal to or less than 1 mmHg as a result of the administration. In some embodiments of the methods, the blood pressure that increases or does not increase following administration of dabuzalgron is systolic blood pressure. In some embodiments of the methods, the blood pressure that increases or doesn't increase following administration of dabuzalgron is diastolic blood pressure. In some embodiments of the methods, the patient's blood pressure does not become hypertensive blood pressure from normal blood pressure as a result of the administration. In some embodiments of the methods, the patient's systolic blood pressure does not become hypertensive blood pressure from normal blood pressure as a result of the administration. In some embodiments of the methods, the patient's diastolic blood pressure does not become hypertensive blood pressure from normal blood pressure as a result of the administration. In some embodiments of the methods, the patient's blood pressure does not become prehypertensive blood pressure from normal blood pressure as a result of the administration. In some embodiments of the methods, the patient's systolic blood pressure does not become prehypertensive blood pressure from normal blood pressure as a result of the administration. In some embodiments of the methods, the patient's diastolic blood pressure does not become prehypertensive blood pressure from normal blood pressure as a result of the administration. In some embodiments of the methods, the patient's blood pressure does not become high blood pressure or undesirable blood pressure or unhealthy blood pressure as a result of the administration. In some embodiments of the methods, the patient's blood pressure does not increase to more than 140/90 mmHg as a result of the administration. In embodiments, the method includes administering dabuzalgron.

In some embodiments of the methods, the effective amount is between about 0.0001 and 10000, 0.001 and 1000, 0.01 and 100, 0.1 and 10, 0.005 and 0.1, 0.005 and 0.05, or 0.007 and 0.02 micrograms/kilogram patient weight. In some embodiments of the methods, the effective amount is about 0.01 micrograms/kilogram patient weight. In some embodiments of the methods, the effective amount is 0.01 micrograms/kilogram patient weight. In some embodiments of the methods, the effective amount is the total amount administered to the patient in a day (e.g. between about 0.0001 and 10000, 0.001 and 1000, 0.01 and 100, 0.1 and 10, 0.005 and 0.1, 0.005 and 0.05, or 0.007 and 0.02 micrograms/kilogram patient weight/day or about 0.01 micrograms/kilogram patient weight/day). In some embodiments of the methods, the effective amount of dabuzalgron administered to a patient or subject in need thereof is about 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 micrograms dabuzalgron/kilograms patient or subject in need thereof/ administration. In some embodiments of the methods, the effective amount of dabuzalgron administered to a patient or subject in need thereof is about 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 micrograms dabuzalgron/kilograms patient or subject in need thereof/day.

In some embodiments of the methods, the effective amount is between about 0.0001 and 10000, 0.001 and 1000, 0.01 and 100, 0.1 and 100, 1 and 100, 10 and 100, 25 and 75, 1 and 50, 1 and 20, 5 and 15, 10 and 1000, 10 and 500, 10 and 250, 10 and 150, 50 and 150, 75 and 125, or 100 and 125 micrograms/kilogram patient weight. In some embodiments of the methods, the effective amount is about 10 micrograms/kilogram patient weight. In some embodiments of the methods, the effective amount is 100 micrograms/kilogram patient weight. In some embodiments of the methods, the effective amount is the total amount administered to the patient in a day (e.g. between about 0.0001 and 10000, 0.001 and 1000, 0.01 and 100, 0.1 and 100, 1 and 100, 10 and 100, 25 and 75, 1 and 50, 1 and 20, 5 and 15, 10 and 1000, 10 and 500, 10 and 250, 10 and 150, 50 and 150, 75 and 125, or 100 and 125 micrograms/kilogram patient weight/day or about 10 micrograms/kilogram patient weight/day or about 100 micrograms/kilogram patient weight/day). In some embodiments of the methods, the effective amount of dabuzalgron administered to a patient or subject in need thereof is 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 micrograms dabuzalgron/kilograms patient or subject in need thereof/administration. In some embodiments of the methods, the effective amount of dabuzalgron administered to a patient or subject in need thereof is 0.0001, 0.0002, 0.0003, 0.0004, 0.0005, 0.0006, 0.0007, 0.0008, 0.0009, 0.001, 0.002, 0.003, 0.004, 0.005, 0.006, 0.007, 0.008, 0.009, 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9, 10, 20, 30, 40, 50, 60, 70, 80, 90, 100, 200, 300, 400, 500, 600, 700, 800, 900, 1000, 2000, 3000, 4000, 5000, 6000, 7000, 8000, 9000, 10000, 20000, 30000, 40000, 50000, 60000, 70000, 80000, 90000, or 100000 micrograms dabuzalgron/kilograms patient or subject in need thereof/day. In some embodiments of the methods, the effective amount of dabuzalgron administered to a patient or subject in need thereof is about 20 micrograms dabuzalgron/kilograms patient or subject. In some embodiments of the methods, the effective amount of dabuzalgron administered to a patient or subject in need thereof is about 20 micrograms dabuzalgron/kilograms patient or subject/day. In some embodiments of the methods, the effective amount of dabuzalgron administered to a patient or subject in need thereof is about 40 micrograms dabuzalgron/kilograms patient or subject/day. In embodiments of the methods, the effective amount of dabuzalgron administered to a patient or subject in need thereof is about 1.5 mg. In embodiments of the methods, the effective amount of dabuzalgron administered to a patient or subject in need thereof is about 3.0 mg/day. In embodiments of the methods, the effective amount of dabuzalgron administered to a patient or subject in need thereof is about 0.5 to 2.5 mg. In embodiments of the methods, the effective amount of dabuzalgron administered to a patient or subject in need thereof is about 0.5 to 5 mg. In embodiments of the methods, the effective amount of dabuzalgron administered to a patient or subject in need thereof is about 0.5 to 10 mg. In embodiments of the methods, the effective amount of dabuzalgron administered to a patient or subject in need thereof is about 0.5 to 25 mg. In some embodiments of the methods, the effective amount of dabuzalgron administered to a patient or subject in need thereof is 20 micrograms dabuzalgron/kilograms patient or subject. In some embodiments of the methods, the effective amount of dabuzalgron administered to a patient or subject in need thereof is 20 micrograms dabuzalgron/kilograms patient or subject/day. In some embodiments of the methods, the effective amount of dabuzalgron administered to a patient or subject in need thereof is 40 micrograms dabuzalgron/kilograms patient or subject/day. In embodiments of the methods, the effective amount of dabuzalgron administered to a patient or subject in need thereof is 1.5 mg. In embodiments of the methods, the effective amount of dabuzalgron administered to a patient or subject in need thereof is 3.0 mg/day. In embodiments of the methods, the effective amount of dabuzalgron administered to a patient or subject in need thereof is 0.5 to 2.5 mg. In embodiments of the methods, the effective amount of dabuzalgron administered to a patient or subject in need thereof is 0.5 to 5 mg. In embodiments of the methods, the effective amount of dabuzalgron administered to a patient or subject in need thereof is 0.5 to 10 mg. In embodiments of the methods, the effective amount of dabuzalgron administered to a patient or subject in need thereof is 0.5 to 25 mg.

In some embodiments of the methods, the effective amount of dabuzalgron, or an analog, pharmaceutically acceptable salt, or prodrug thereof, is administered to a patient or subject in need thereof once. In some embodiments of the methods, the effective amount of dabuzalgron, or an analog, pharmaceutically acceptable salt, or prodrug thereof, is administered to a patient or subject in need thereof for one day. In some embodiments of the methods, the effective amount of dabuzalgron, or an analog, pharmaceutically acceptable salt, or prodrug thereof, is administered to a patient or subject in need thereof for two days. In some embodiments of the methods, the effective amount of dabuzalgron, or an analog, pharmaceutically acceptable salt, or prodrug thereof, is administered to a patient or subject in need thereof for three days. In some embodiments of the methods, the effective amount of dabuzalgron, or an analog, pharmaceutically acceptable salt, or prodrug thereof, is administered to a patient or subject in need thereof for four days. In some embodiments of the methods, the effective amount of dabuzalgron, or an analog, pharmaceutically acceptable salt, or prodrug thereof, is administered to a patient or subject in need thereof for five days. In some embodiments of the methods, the effective amount of dabuzalgron, or an analog, pharmaceutically acceptable salt, or prodrug thereof, is administered to a patient or subject in need thereof for six days. In some embodiments of the methods, the effective amount of dabuzalgron, or an analog, pharmaceutically acceptable salt, or prodrug thereof, is administered to a patient or subject in need thereof for seven days. In some embodiments of the methods, the effective amount of dabuzalgron, or an analog, pharmaceutically acceptable salt, or prodrug thereof, is administered to a patient or subject in need thereof for two weeks. In some embodiments of the methods, the effective amount of dabuzalgron, or an analog, pharmaceutically acceptable salt, or prodrug thereof, is administered to a patient or subject in need thereof for three weeks. In some embodiments of the methods, the effective amount of dabuzalgron, or an analog, pharmaceutically acceptable salt, or prodrug thereof, is administered to a patient or subject in need thereof for four weeks. In some embodiments of the methods, the effective amount of dabuzalgron, or an analog, pharmaceutically acceptable salt, or prodrug thereof, is administered to a patient or subject in need thereof for about one month. In some embodiments of the methods, the effective amount of dabuzalgron, or an analog, pharmaceutically acceptable salt, or prodrug thereof, is administered to a patient or subject in need thereof for about two months. In some embodiments of the methods, the effective amount of dabuzalgron, or an analog, pharmaceutically acceptable salt, or prodrug thereof, is administered to a patient or subject in need thereof for about three months. In some embodiments of the methods, the effective amount of dabuzalgron, or an analog, pharmaceutically acceptable salt, or prodrug thereof, is administered to a patient or subject in need thereof for about four months. In some embodiments of the methods, the effective amount of dabuzalgron, or an analog, pharmaceutically acceptable salt, or prodrug thereof, is administered to a patient or subject in need thereof for about five months. In some embodiments of the methods, the effective amount of dabuzalgron, or an analog, pharmaceutically acceptable salt, or prodrug thereof, is administered to a patient or subject in need thereof for about six months. In some embodiments of the methods, the effective amount of dabuzalgron, or an analog, pharmaceutically acceptable salt, or prodrug thereof, is administered to a patient or subject in need thereof for about 7, 8, 9, 10, 11, or 12 months.

In some embodiments of the methods, the effective amount of dabuzalgron, or an analog, pharmaceutically acceptable salt, or prodrug thereof, is administered to a patient or subject in need thereof for about one, two, three, four, five, six, seven, eight, nine, ten, 11, 12, 13, 14, 15,16, 17, 18, 19, 20, or more years. In some embodiments of the methods, the effective amount of dabuzalgron, or an analog, pharmaceutically acceptable salt, or prodrug thereof, is administered to a patient or subject in need thereof for the duration of the disease (e.g. cardiomyopathy, cardiotoxicity, disease associated with cardiomyopathy, cardiomyopathy associated with chemotherapy treatment (e.g., anthracycline treatment, doxorubicin treatment), or cardiotoxicity associated with chemotherapy treatment (e.g., anthracycline treatment, doxorubicin treatment)). In some embodiments of the methods, the administering is parenteral, intravenous, intraarterial, buccal, sublingual, oral, peroral, transdermal, or nasal. In some embodiments of the methods, the administering is to the heart. In some embodiments of the methods, the administering is to the heart muscle.

In some embodiments of the methods, the effective amount of dabuzalgron is administered to a patient or subject in need thereof once. In some embodiments of the methods, the effective amount of dabuzalgron is administered to a patient or subject in need thereof for one day. In some embodiments of the methods, the effective amount of dabuzalgron is administered to a patient or subject in need thereof for two days. In some embodiments of the methods, the effective amount of dabuzalgron is administered to a patient or subject in need thereof for three days. In some embodiments of the methods, the effective amount of dabuzalgron is administered to a patient or subject in need thereof for four days. In some embodiments of the methods, the effective amount of dabuzalgron is administered to a patient or subject in need thereof for five days. In some embodiments of the methods, the effective amount of dabuzalgron is administered to a patient or subject in need thereof for six days. In some embodiments of the methods, the effective amount of dabuzalgron is administered to a patient or subject in need thereof for seven days. In some embodiments of the methods, the effective amount of dabuzalgron is administered to a patient or subject in need thereof for two weeks. In some embodiments of the methods, the effective amount of dabuzalgron is administered to a patient or subject in need thereof for three weeks. In some embodiments of the methods, the effective amount of dabuzalgron is administered to a patient or subject in need thereof for four weeks. In some embodiments of the methods, the effective amount of dabuzalgron is administered to a patient or subject in need thereof for about one month. In some embodiments of the methods, the effective amount of dabuzalgron is administered to a patient or subject in need thereof for about two months. In some embodiments of the methods, the effective amount of dabuzalgron is administered to a patient or subject in need thereof for about three months. In some embodiments of the methods, the effective amount of dabuzalgron is administered to a patient or subject in need thereof for about four months. In some embodiments of the methods, the effective amount of dabuzalgron is administered to a patient or subject in need thereof for about five months. In some embodiments of the methods, the effective amount of dabuzalgron is administered to a patient or subject in need thereof for about six months. In some embodiments of the methods, the effective amount of dabuzalgron is administered to a patient or subject in need thereof for about 7, 8, 9, 10, 11, or 12 months.

In some embodiments of the methods, the effective amount of dabuzalgron is administered to a patient or subject in need thereof for about one, two, three, four, five, six, seven, eight, nine, ten, 11, 12, 13, 14, 15,16, 17, 18, 19, 20, or more years. In some embodiments of the methods, the effective amount of dabuzalgron is administered to a patient or subject in need thereof for the duration of the disease (e.g. cardiomyopathy, cardiotoxicity, disease associated with cardiomyopathy, cardiomyopathy associated with chemotherapy treatment (e.g., anthracycline treatment, doxorubicin treatment), or cardiotoxicity associated with chemotherapy treatment (e.g., anthracycline treatment, doxorubicin treatment)). In some embodiments of the methods, the administering is parenteral, intravenous, intraarterial, buccal, sublingual, oral, peroral, transdermal, or nasal. In some embodiments of the methods, the administering is to the heart. In some embodiments of the methods, the administering is to the heart muscle.

In some embodiments, the methods include an effective amount of dabuzalgron. In some embodiments, the methods include an effective amount of an analog of dabuzalgron. In some embodiments, the methods include an effective amount of an isomer of dabuzalgron. In some embodiments, the methods include an effective amount of a pharmaceutically acceptable salt of dabuzalgron. In some embodiments, the methods include an effective amount of a prodrug of dabuzalgron.

Therapeutically effective doses of dabuzalgron, or an analog, pharmaceutically acceptable salt, or prodrug thereof, for use in a mammal, which have no effect on blood pressure or which result in no significant increase in blood pressure or result in an acceptable increase in blood pressure (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mmHg, or does not change normal blood pressure to prehypertensive or hypertensive blood pressure, or does not cause the blood pressure to become unhealthy blood pressure or high blood pressure or undesirable blood pressure, or does not cause the blood pressure to be greater than 140/90 mmHg), yet prevent the onset or progression of cardiomyopathy or cardiotoxicity, are determined through standard methods in the art. For example, varying doses of dabuzalgron, or an analog, pharmaceutically acceptable salt, or prodrug thereof, are administered to a patient (e.g suffering from cardiomyopathy or at risk of developing cardiomyopathy or a patient suffering from cardiotoxicity or a patient at risk of developing cardiotoxicity or a person suffering from or at risk of suffering from cardiomyopathy or cardiotoxicity associated with chemotherapy (e.g., anthracycline treatment)), followed by monitoring of blood pressure. Assays to determine whether or not dabuzalgron, or an analog, pharmaceutically acceptable salt, or prodrug thereof, is effective in preventing the onset of cardiomyopathy, or reducing its progression, are known to persons having ordinary skill in the art and include monitoring of fractional shortening, ejection fraction, end-diastolic volume and troponin levels (methods described in Bielecka-Dabrowa et al. 2008, Cardiology J. 278:1-5; Nellessen et al. 2006, Clin. Cardial. 29:219-224). Assays to determine whether or not dabuzalgron, or an analog, pharmaceutically acceptable salt, or prodrug thereof, is effective in preventing the onset of cardiotoxicity, or reducing its progression, are known to persons having ordinary skill in the art and include monitoring of fractional shortening, ejection fraction, end-diastolic volume and troponin levels (methods described in Bielecka-Dabrowa et al. 2008, Cardiology J. 278:1-5; Nellessen et al. 2006, Clin. Cardial. 29:219-224). In one embodiment, no increase in blood pressure is observed when the blood pressure is measured 24 hours after treatment, in another embodiment no increase in blood pressure is observed when the blood pressure is measured 48 hours, 72 hours, 1 week or 1 month after treatment. In yet another embodiment, blood pressure, when measured after 48 hours, 72 hours, 1 week, or 1 month, increases less than 10% or less than 15% after treatment with dabuzalgron, or an analog, pharmaceutically acceptable salt, or prodrug thereof. In some embodiments, blood pressure increases (e.g., by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mmHg) following administration of a therapeutically effective or prophylactically effective amount of dabuzalgron, or an analog, pharmaceutically acceptable salt, or prodrug thereof. In some embodiments, blood pressure increases following administration of a therapeutically effective or prophylactically effective amount of dabuzalgron, or an analog, pharmaceutically acceptable salt, or prodrug thereof, but does not change from normal to prehypertensive or from normal to hypertensive or from prehypertensive to hypertensive blood pressure. In some embodiments, blood pressure increases following administration of a therapeutically effective or prophylactically effective amount of dabuzalgron, or an analog, pharmaceutically acceptable salt, or prodrug thereof, but does not become an undesirable blood pressure, high blood pressure, or unhealthy blood pressure. In some embodiments, blood pressure increases following administration of a therapeutically effective or prophylactically effective amount of dabuzalgron, or an analog, pharmaceutically acceptable salt, or prodrug thereof, but does not become greater than 140/90 mmHg.

Therapeutically effective doses of dabuzalgron for use in a mammal, which have no effect on blood pressure or which result in no significant increase in blood pressure or result in an acceptable increase in blood pressure (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mmHg, or does not change normal blood pressure to prehypertensive or hypertensive blood pressure, or does not cause the blood pressure to become unhealthy blood pressure or high blood pressure or undesirable blood pressure, or does not cause the blood pressure to be greater than 140/90 mmHg), yet prevent the onset or progression of cardiomyopathy or cardiotoxicity, are determined through standard methods in the art. For example, varying doses of dabuzalgron are administered to a patient (e.g suffering from cardiomyopathy or at risk of developing cardiomyopathy or a patient suffering from cardiotoxicity or a patient at risk of developing cardiotoxicity or a person suffering from or at risk of suffering from cardiomyopathy or cardiotoxicity associated with chemotherapy (e.g., anthracycline treatment)), followed by monitoring of blood pressure. Assays to determine whether or not dabuzalgron is effective in preventing the onset of cardiomyopathy, or reducing its progression, are known to persons having ordinary skill in the art and include monitoring of fractional shortening, ejection fraction, end-diastolic volume and troponin levels (methods described in Bielecka-Dabrowa et al. 2008, Cardiology J. 278:1-5; Nellessen et al. 2006, Clin. Cardial. 29:219-224). Assays to determine whether or not dabuzalgron is effective in preventing the onset of cardiotoxicity, or reducing its progression, are known to persons having ordinary skill in the art and include monitoring of fractional shortening, ejection fraction, end-diastolic volume and troponin levels (methods described in Bielecka-Dabrowa et al. 2008, Cardiology J. 278:1-5; Nellessen et al. 2006, Clin. Cardial. 29:219-224). In one embodiment, no increase in blood pressure is observed when the blood pressure is measured 24 hours after treatment, in another embodiment no increase in blood pressure is observed when the blood pressure is measured 48 hours, 72 hours, 1 week or 1 month after treatment. In yet another embodiment, blood pressure, when measured after 48 hours, 72 hours, 1 week, or 1 month, increases less than 10% or less than 15% after treatment with dabuzalgron. In some embodiments, blood pressure increases (e.g. by 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 mmHg) following administration of a therapeutically effective or prophylactically effective amount of dabuzalgron. In some embodiments, blood pressure increases following administration of a therapeutically effective or prophylactically effective amount of dabuzalgron but does not change from normal to prehypertensive or from normal to hypertensive or from prehypertensive to hypertensive blood pressure. In some embodiments, blood pressure increases following administration of a therapeutically effective or prophylactically effective amount of dabuzalgron but does not become an undesirable blood pressure, high blood pressure, or unhealthy blood pressure. In some embodiments, blood pressure increases following administration of a therapeutically effective or prophylactically effective amount of dabuzalgron but does not become greater than 140/90 mmHg.

Progression of cardiomyopathy may be monitored in part by measuring levels of serum biomarkers, such as creatine kinase, troponin, ST2 (e.g. soluble ST2), GDF-15, or brain natriuretic peptide (BNP). Progression of cardiotoxicity may be monitored in part by measuring levels of serum biomarkers, such as creatine kinase, troponin, ST2 (e.g. soluble ST2), GDF-15, or brain natriuretic peptide (BNP).

Progression of cardiomyopathy may be assessed in part by measuring fractional shortening (FS) or ejection fraction (EF). Progression of cardiotoxicity may be assessed in part by measuring fractional shortening (FS) or ejection fraction (EF). FS is used to measure left ventricle performance by measuring the change in the diameter of the left ventricle between the contracted and relaxed state on M-mode tracings and calculating the ratio according to the formula: [(LV end-diastolic diameter-LV end-systolic diameter)/LV end-diastolic diameter)]×100. EF is calculated from left ventricular volumes determined by 2-dimensional echo, as [(LV end-diastolic volume-LV end-systolic volume)/LV end-diastolic volume)]×100. A decrease in FS or EF is indicative of heart damage. In embodiments, a therapeutically effective amount of dabuzalgron, or an analog, pharmaceutically acceptable salt, or prodrug thereof, is administered to a subject suffering from or at risk of cardiomyopathy or cardiotoxicity, wherein the dabuzalgron, or an analog, pharmaceutically acceptable salt, or prodrug thereof, prevents more than 5-30% (e.g. more than 5, 6, 7, 8, 9, 10, 11, 12, 13, 14, 15, 16, 17, 18, 19, 20, 21, 22, 23, 24, 25, 26, 27, 28, 29, or 30%) reduction in the FS or EF as compared to a subject suffering from or at risk of cardiomyopathy or cardiotoxicity, not administered dabuzalgron, or an analog, pharmaceutically acceptable salt, or prodrug thereof. In another embodiment, administration of dabuzalgron, or an analog, pharmaceutically acceptable salt, or prodrug thereof, to a subject suffering from or at risk of cardiomyopathy or cardiotoxicity prevents more than 5% reduction in the FS or EF as compared to a subject suffering from or at risk of cardiomyopathy or cardiotoxicity, not administered dabuzalgron, or an analog, pharmaceutically acceptable salt, or prodrug thereof. In one embodiment, a therapeutically effective amount of dabuzalgron is administered to a subject suffering from or at risk of cardiomyopathy or cardiotoxicity, wherein the dabuzalgron prevents more than 5-30% (e.g. more than 5, 6, 7, 8, 9, 10, 11, 12, 13, 14, 15, 16, 17, 18, 19, 20, 21, 22, 23, 24, 25, 26, 27, 28, 29, or 30%) reduction in the FS or EF as compared to a subject suffering from or at risk of cardiomyopathy or cardiotoxicity, not administered dabuzalgron. In another embodiment, administration of dabuzalgron to a subject suffering from or at risk of cardiomyopathy or cardiotoxicity prevents more than 5% reduction in the FS or EF as compared to a subject suffering from or at risk of cardiomyopathy or cardiotoxicity, not administered dabuzalgron.

In one embodiment, a therapeutically effective amount of dabuzalgron, or an analog, pharmaceutically acceptable salt, or prodrug thereof, is administered to a subject suffering from or at risk of cardiomyopathy or cardiotoxicity, wherein the dabuzalgron, or an analog, pharmaceutically acceptable salt, or prodrug thereof, prevents more than 5-30% (e.g. more than 5, 6, 7, 8, 9, 10, 11, 12, 13, 14, 15, 16, 17, 18, 19, 20, 21, 22, 23, 24, 25, 26, 27, 28, 29, or 30%) increase in the end-diastolic volume as compared to a subject suffering from or at risk of cardiomyopathy or cardiotoxicity, not administered dabuzalgron, or an analog, pharmaceutically acceptable salt, or prodrug thereof. In another embodiment, administration of dabuzalgron, or an analog, pharmaceutically acceptable salt, or prodrug thereof, to a subject suffering from or at risk of cardiomyopathy or cardiotoxicity prevents more than 5% increase in the end-diastolic volume as compared to a subject suffering from or at risk of cardiomyopathy or cardiotoxicity, not administered dabuzalgron, or an analog, pharmaceutically acceptable salt, or prodrug thereof. In one embodiment, a therapeutically effective amount of dabuzalgron is administered to a subject suffering from or at risk of cardiomyopathy or cardiotoxicity, wherein the dabuzalgron prevents more than 5-30% (e.g. more than 5, 6, 7, 8, 9, 10, 11, 12, 13, 14, 15, 16, 17, 18, 19, 20, 21, 22, 23, 24, 25, 26, 27, 28, 29, or 30%) increase in the end-diastolic volume as compared to a subject suffering from or at risk of cardiomyopathy or cardiotoxicity, not administered dabuzalgron. In another embodiment, administration of dabuzalgron to a subject suffering from or at risk of cardiomyopathy or cardiotoxicity prevents more than 5% increase in the end-diastolic volume as compared to a subject suffering from or at risk of cardiomyopathy or cardiotoxicity, not administered dabuzalgron.

In some embodiments, cardiomyopathy or cardiotoxicity is detected by a method selected from the group consisting of X-ray (e.g. chest), echocardiogram, electrocardiogram, cardiac catheterization, cardiac biopsy, computerized tomography, and magnetic resonance imaging.

It is well known that creatine kinase (CK) or troponin are released from myocytes when myocyte necrosis occurs. Accordingly, measuring levels of CK or troponin in the serum may be done to assess the onset and progression of cardiomyopathy or cardiotoxicity in a subject. Measuring serum CK levels is done using methods known to those of ordinary skill in the art, for example, by a coupled reaction of glucokinase and glucose-6-phosphate dehydrogenase using a diagnostic kit. In one embodiment, a therapeutically effective amount of dabuzalgron, or an analog, pharmaceutically acceptable salt, or prodrug thereof, is administered to a subject suffering from or at risk of cardiomyopathy or cardiotoxicity, wherein the dabuzalgron, or an analog, pharmaceutically acceptable salt, or prodrug thereof, reduces the level of CK in the serum of the subject as compared to CK levels found in the serum of a subject suffering from or at risk of cardiomyopathy or cardiotoxicity, not administered dabuzalgron, or an analog, pharmaceutically acceptable salt, or prodrug thereof. In some embodiments, a therapeutically effective amount of dabuzalgron, or an analog, pharmaceutically acceptable salt, or prodrug thereof, is administered to a subject suffering from or at risk of cardiomyopathy or cardiotoxicity, wherein the dabuzalgron, or an analog, pharmaceutically acceptable salt, or prodrug thereof, reduces the level of troponin, BNP, GDF-15, or ST2 (e.g. soluble ST2) in the serum of the subject as compared to troponin, BNP, GDF-15, or ST2 (e.g. soluble ST2) levels respectively found in the serum of a subject suffering from or at risk of cardiomyopathy or cardiotoxicity, not administered dabuzalgron, or an analog, pharmaceutically acceptable salt, or prodrug thereof. In one embodiment, a therapeutically effective amount of dabuzalgron, or an analog, pharmaceutically acceptable salt, or prodrug thereof, is administered to a subject suffering from or at risk of cardiomyopathy or cardiotoxicity, wherein the dabuzalgron, or an analog, pharmaceutically acceptable salt, or prodrug thereof, increases the level GDF-15 in the serum of the subject as compared to GDF-15 levels found in the serum of a subject suffering from or at risk of cardiomyopathy or cardiotoxicity, not administered dabuzalgron, or an analog, pharmaceutically acceptable salt, or prodrug thereof. In some embodiments, a therapeutically effective amount of dabuzalgron, or an analog, pharmaceutically acceptable salt, or prodrug thereof, is administered to a subject suffering from or at risk of cardiomyopathy or cardiotoxicity, wherein the dabuzalgron, or an analog, pharmaceutically acceptable salt, or prodrug thereof, does not modulate the level of troponin, BNP, GDF-15, or ST2 (e.g. soluble ST2) in the serum of the subject as compared to troponin, BNP, GDF-15, or ST2 (e.g. soluble ST2) levels respectively found in the serum of a subject suffering from or at risk of cardiomyopathy or cardiotoxicity, not administered dabuzalgron, or an analog, pharmaceutically acceptable salt, or prodrug thereof. In some embodiments, a therapeutically effective amount of dabuzalgron, or an analog, pharmaceutically acceptable salt, or prodrug thereof, is administered to a subject suffering from or at risk of cardiomyopathy or cardiotoxicity, wherein the dabuzalgron, or an analog, pharmaceutically acceptable salt, or prodrug thereof, improves the level of troponin, BNP, GDF-15, or ST2 (e.g. soluble ST2) in the serum of the subject as compared to troponin, BNP, GDF-15, or ST2 (e.g. soluble ST2) levels respectively found in the serum of a subject suffering from or at risk of cardiomyopathy or cardiotoxicity, not administered dabuzalgron, or an analog, pharmaceutically acceptable salt, or prodrug thereof. In some embodiments, improvement of the level of BNP, GDF-15, or ST2 (e.g. soluble ST2) in the serum of the subject is lowering of the level. In some embodiments, improvement of the level of BNP, GDF-15, or ST2 (e.g. soluble ST2) in the serum of the subject is increasing the level. In some embodiments, improvement of the level of BNP, GDF-15, or ST2 (e.g. soluble ST2) in the serum of the subject is as recommended by the American Heart Association. In some embodiments, determining what constitutes an improvement of the level of BNP, GDF-15, or ST2 (e.g. soluble ST2) in the serum of the subject is well within the skill of a person of ordinary skill in the art (e.g. doctor, cardiologist, internist).

In one embodiment, a therapeutically effective amount of dabuzalgron is administered to a subject suffering from or at risk of cardiomyopathy or cardiotoxicity, wherein the dabuzalgron reduces the level of CK in the serum of the subject as compared to CK levels found in the serum of a subject suffering from or at risk of cardiomyopathy or cardiotoxicity, not administered dabuzalgron. In some embodiments, a therapeutically effective amount of dabuzalgron is administered to a subject suffering from or at risk of cardiomyopathy or cardiotoxicity, wherein the dabuzalgron reduces the level of troponin, BNP, GDF-15, or ST2 (e.g. soluble ST2) in the serum of the subject as compared to troponin, BNP, GDF-15, or ST2 (e.g. soluble ST2) levels respectively found in the serum of a subject suffering from or at risk of cardiomyopathy or cardiotoxicity, not administered dabuzalgron. In one embodiment, a therapeutically effective amount of dabuzalgron is administered to a subject suffering from or at risk of cardiomyopathy or cardiotoxicity, wherein the dabuzalgron increases the level GDF-15 in the serum of the subject as compared to GDF-15 levels found in the serum of a subject suffering from or at risk of cardiomyopathy or cardiotoxicity, not administered dabuzalgron. In some embodiments, a therapeutically effective amount of dabuzalgron is administered to a subject suffering from or at risk of cardiomyopathy or cardiotoxicity, wherein the dabuzalgron does not modulate the level of troponin, BNP, GDF-15, or ST2 (e.g. soluble ST2) in the serum of the subject as compared to troponin, BNP, GDF-15, or ST2 (e.g. soluble ST2) levels respectively found in the serum of a subject suffering from or at risk of cardiomyopathy or cardiotoxicity, not administered dabuzalgron. In some embodiments, a therapeutically effective amount of dabuzalgron is administered to a subject suffering from or at risk of cardiomyopathy or cardiotoxicity, wherein the dabuzalgron improves the level of troponin, BNP, GDF-15, or ST2 (e.g. soluble ST2) in the serum of the subject as compared to troponin, BNP, GDF-15, or ST2 (e.g. soluble ST2) levels respectively found in the serum of a subject suffering from or at risk of cardiomyopathy or cardiotoxicity, not administered dabuzalgron. In some embodiments, improvement of the level of BNP, GDF-15, or ST2 (e.g. soluble ST2) in the serum of the subject is lowering of the level. In some embodiments, improvement of the level of BNP, GDF-15, or ST2 (e.g. soluble ST2) in the serum of the subject is increasing the level. In some embodiments, improvement of the level of BNP, GDF-15, or ST2 (e.g. soluble ST2) in the serum of the subject is as recommended by the American Heart Association. In some embodiments, determining what constitutes an improvement of the level of BNP, GDF-15, or ST2 (e.g. soluble ST2) in the serum of the subject is well within the skill of a person of ordinary skill in the art (e.g. doctor, cardiologist, internist).

Another indicator of cardiomyopathy or cardiotoxicity is increased cardiomyocyte apoptosis. Cardiomyocyte apoptosis may be measured by methods known in the art, including for example by MRI, optionally including probes such as Annexin V (ANX), superparamagnetic iron oxide (SPIO), ANX conjugated to SPIO (ANX-SPIO), ANX conjugated to other detectable moieties, other phosphatidylserine binding detectable moieties, or other MM probes known in the art (see Dash, R. et al. *Magn. Reson. Med.* 2011; 66:1152-1162 incorporated herein in its entirety). Cardiomyopathy or cardiotoxicity may also be accompanied by an increase in fibrosis of the cardiac tissue. Fibrosis may be measured using Sirius Red staining, a method well known to skilled artisans. In one embodiment, a therapeutically effective amount of dabuzalgron, or an analog, pharmaceutically acceptable salt, or prodrug thereof, is administered to a subject suffering from or at risk of cardiomyopathy or cardiotoxicity, wherein the dabuzalgron, or an analog, pharmaceutically acceptable salt, or prodrug thereof, reduces the area of fibrosis in the heart as compared to a subject suffering from or at risk of cardiomyopathy or cardiotoxicity, not administered dabuzalgron, or an analog, pharmaceutically acceptable salt, or prodrug thereof. In one embodiment, a therapeutically effective amount of dabuzalgron is administered to a subject suffering from or at risk of cardiomyopathy or cardiotoxicity, wherein the dabuzalgron reduces the area of fibrosis in the heart as compared to a subject suffering from or at risk of cardiomyopathy or cardiotoxicity, not administered dabuzalgron.

In one embodiment, the method prevents a decrease in fractional shortening in the subject by more than 5% to 30% (e.g. more than 5, 6, 7, 8, 9, 10, 11, 12, 13, 14, 15, 16, 17, 18, 19, 20, 21, 22, 23, 24, 25, 26, 27, 28, 29, or 30%) as compared to fractional shortening in a subject suffering from or at risk of cardiomyopathy or cardiotoxicity, not administered dabuzalgron, or an analog, pharmaceutically acceptable salt, or prodrug thereof. In one embodiment, the method prevents a decrease in fractional shortening in the subject by more than 5% to 30% (e.g. more than 5, 6, 7, 8, 9, 10, 11, 12, 13, 14, 15, 16, 17, 18, 19, 20, 21, 22, 23, 24, 25, 26, 27, 28, 29, or 30%) as compared to fractional shortening in a subject suffering from or at risk of cardiomyopathy or cardiotoxicity, not administered dabuzalgron.

In one embodiment, the method prevents an increase in the amount of creatine kinase or troponin in the serum of the subject by more than 2-fold, 4-fold, or 5-fold as compared to the amount of creatine kinase or troponin in the serum of the subject suffering from or at risk of cardiomyopathy or cardiotoxicity, not administered dabuzalgron. In one embodiment, the method prevents an increase in the amount of ST2 (interleukin 1 receptor-like 1) (e.g., soluble ST2), GDF-15 (growth differentiation factor 15), or BNP (brain natriuretic peptide) as compared to the amount of ST2, GDF-15, or BNP in the serum of the subject suffering from or at risk of cardiomyopathy or cardiotoxicity, not administered dabuzalgron. In one embodiment, the method increases the amount of ST2 (interleukin 1 receptor-like 1) (e.g., soluble ST2), GDF-15 (growth differentiation factor 15), or BNP (brain natriuretic peptide) as compared to the amount ST2, GDF-15, or BNP in the serum of the subject suffering from or at risk of cardiomyopathy or cardiotoxicity, not administered dabuzalgron. In one embodiment, the method decreases the amount of ST2 (interleukin 1 receptor-like 1) (e.g., soluble ST2), GDF-15 (growth differentiation factor 15), or BNP (brain natriuretic peptide) as compared to the amount ST2, GDF-15, or BNP in the serum of the subject suffering from or at risk of cardiomyopathy or cardiotoxicity, not administered dabuzalgron.

In one embodiment, the method prevents an increase in the percentage of cardiac fibrosis area by more than 1% to 20% (e.g. by more than 1, 2, 3, 4, 5, 6, 7, 8, 9, 10, 11, 12, 13, 14, 15, 16, 17, 18, 19, or 20%) in the heart of the subject suffering from or at risk of cardiomyopathy or cardiotoxicity, not administered dabuzalgron.

In some embodiments, the methods include improving (e.g., increasing) heart contraction in a patient. In some embodiments, the methods include preventing heart muscle cells from dying. In some embodiments, the methods include stimulating repair of heart muscle. In some embodiments, the methods include stimulating anabolic processes or function in cells (e.g., cardiac muscle cells) or tissue (e.g., cardiac tissue).

Any of the methods including administration or use of dabuzalgron described herein, may instead administer or use an analog of dabuzalgron. Any of the methods including administration or use of dabuzalgron described herein, may instead administer or use a pharmaceutically acceptable salt of dabuzalgron. Any of the methods including administration or use of dabuzalgron described herein, may instead administer or use a prodrug of dabuzalgron.

The compounds of the invention can be administered alone or can be coadministered to the patient. Coadministration is meant to include simultaneous or sequential administration of the compounds individually or in combination (more than one compound). Thus, the preparations can also be combined, when desired, with other active substances (e.g., to reduce metabolic degradation).

The compounds of the present invention can be prepared and administered in a wide variety of oral, parenteral and topical dosage forms. Oral preparations include tablets, pills, powder, dragees, capsules, liquids, lozenges, cachets, gels, syrups, slurries, suspensions, etc., suitable for ingestion by the patient. The compounds of the present invention can also be administered by injection, that is, intravenously, intracranially, intracardiac administration, intramuscularly, intracutaneously, subcutaneously, intraduodenally, or intraperitoneally. Also, the compounds described herein can be administered by inhalation, for example, intranasally. Additionally, the compounds of the present invention can be administered transdermally. It is also envisioned that multiple routes of administration (e.g., intramuscular, oral, transdermal) can be used to administer the compounds of the invention. Accordingly, the present invention also provides pharmaceutical compositions comprising a pharmaceutically acceptable excipient and one or more compounds of the invention.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances that may also act as diluents, flavoring agents, binders, preservatives, tablet disintegrating agents, or an encapsulating material.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethyl-cellulose; and gums including arabic and tragacanth; as well as proteins including, but not limited to, gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol.

Liquid form preparations include solutions, suspensions, and emulsions, for example, water or water/propylene glycol solutions. For parenteral injection, liquid preparations can be formulated in solution in aqueous polyethylene glycol solution.

When parenteral application is needed or desired, particularly suitable admixtures for the compounds of the invention are injectable, sterile solutions, preferably oily or aqueous solutions, as well as suspensions, emulsions, or implants, including suppositories. In particular, carriers for parenteral administration include aqueous solutions of dextrose, saline, pure water, ethanol, glycerol, propylene glycol, peanut oil, sesame oil, polyoxyethylene-block polymers, and the like. Ampules are convenient unit dosages. The compounds of the invention can also be incorporated into liposomes or administered via transdermal pumps or patches. Pharmaceutical admixtures suitable for use in the present invention are well-known to those of skill in the art and are described, for example, in Pharmaceutical Sciences (17th Ed., Mack Pub. Co., Easton, Pa.) and WO 96/05309, the teachings of both of which are hereby incorporated by reference.

Aqueous solutions suitable for oral use can be prepared by dissolving the active component in water and adding suitable colorants, flavors, stabilizers, and thickening agents as desired. Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations that are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, J. Pharmacol. Exp. Ther. 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes.

Pharmaceutical compositions provided by the present invention include compositions wherein the active ingredient is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., modulating the activity of a target molecule (e.g. α1 adrenergic receptor), and/or reducing, eliminating, or slowing the progression of disease symptoms (e.g. cardiomyopathy or cardiotoxicity). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated, kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art. As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The ratio between toxicity and therapeutic effect for a particular compound is its therapeutic index and can be expressed as the ratio between $LD_{50}$ (the amount of compound lethal in 50% of the population) and $ED_{50}$ (the amount of compound effective in 50% of the population). Compounds that exhibit high therapeutic indices are preferred. Therapeutic index data obtained from cell culture assays and/or animal studies can be used in formulating a range of dosages for use in humans. The dosage of such compounds preferably lies within a range of plasma concentrations that include the $ED_{50}$ with little or no toxicity. The dosage may vary within this range depending upon the dosage form employed and the route of administration utilized. See, e.g. Fingl et al., In: THE PHARMACOLOGICAL BASIS OF THERAPEUTICS, Ch. 1, p. 1, 1975. The exact formulation, route of administration and dosage can be chosen by the individual physician in view of the patient's condition and the particular method in which the compound is used.

In another embodiment, the compositions of the present invention are useful for parenteral administration, such as intravenous (IV) administration or administration into a body cavity or lumen of an organ. The formulations for administration will commonly comprise a solution of the compositions of the present invention dissolved in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables. These solutions are sterile and generally free of undesirable matter. These formulations may be sterilized by conventional, well known sterilization techniques. The formulations may contain pharmaceutically acceptable auxiliary substances as required to approximate physiological conditions such as pH adjusting and buffering agents, toxicity adjusting agents, e.g., sodium acetate, sodium chloride, potassium chloride, calcium chloride, sodium lactate and the like. The concentration of the compositions of the present invention in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

In some embodiments, co-administration includes administering one active agent within 0.5, 1, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another.

As non-limiting examples, the compositions, drugs, and compounds described herein can be co-administered with or used in combination with cardiomyopathy or cardiotoxicity agents including, but not limited to beta-adrenergic blockers, angiotensin converting enzyme inhibitors, or aldosterone or angiotensin receptor blockers. As non-limiting examples, the compositions, drugs, and compounds described herein can be co-administered with or used in combination with other agents useful in increasing the cellular uptake (e.g. uptake by cardiac cells) of the compositions, drugs, or compounds (e.g., dabuzalgron, or an analog, pharmaceutically acceptable salt, or prodrug thereof) for treating diseases (e.g., cardiomyopathy, cardiotoxicity, heart muscle damage). In some embodiments the cellular uptake is increased by activating a transporter protein in the cell.

The pharmaceutical compositions of the present invention may be sterilized by conventional, well-known sterilization techniques or may be produced under sterile conditions. Aqueous solutions can be packaged for use or filtered under aseptic conditions and lyophilized, the lyophilized preparation being combined with a sterile aqueous solution prior to administration. The compositions can contain pharmaceutically acceptable auxiliary substances as required to approximate physiological conditions, such as pH adjusting and buffering agents, tonicity adjusting agents, wetting agents, and the like, e.g., sodium acetate, sodium lactate, sodium chloride, potassium chloride, calcium chloride, sorbitan monolaurate, and triethanolamine oleate.

Formulations suitable for oral administration can comprise: (a) liquid solutions, such as an effective amount of a packaged dabuzalgron, or an analog, pharmaceutically acceptable salt, or prodrug thereof, suspended in diluents, e.g., water, saline, or PEG 400; (b) capsules, sachets, or tablets, each containing a predetermined amount of dabuzalgron, or an analog, pharmaceutically acceptable salt, or prodrug thereof, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise dabuzalgron, or an analog, pharmaceutically acceptable salt, or prodrug thereof, in a flavor, e.g., sucrose, as well as pastilles comprising dabuzalgron, or an analog, pharmaceutically acceptable salt, or prodrug thereof, in an inert base, such as gelatin and glycerin or sucrose and acacia emulsions, gels, and the like, containing, in addition to dabuzalgron, or an analog, pharmaceutically acceptable salt, or prodrug thereof, carriers known in the art.

The alpha-1 adrenergic receptor agonist of choice (e.g. dabuzalgron, or an analog, pharmaceutically acceptable salt, or prodrug thereof), alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like. In some embodiments, aerosol formulations are used to administer an alpha-1 adrenergic receptor agonist of choice (e.g. dabuzalgron, or an analog, pharmaceutically acceptable salt, or prodrug thereof) to the lungs.

Formulations suitable for parenteral administration, such as, for example, by intraarticular (in the joints), intravenous, intramuscular, intratumoral, intradermal, intraperitoneal, intracranial, intracardiac, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. Injection solutions and suspensions can also be prepared from sterile powders, granules, and tablets. In the practice of the present invention, compositions can be administered, for example, by intravenous infusion, intracardiac administration, orally, topically, intraperitoneally, intravesically, intracranially, or intrathecally. Parenteral administration, oral administration, and intravenous administration are the preferred methods of administration. The formulations of compounds can be presented in unit-dose or multi-dose sealed containers, such as ampoules and vials.

The pharmaceutical preparation is preferably in unit dosage form. In such form the preparation is subdivided into unit doses containing appropriate quantities of the active component, e.g., dabuzalgron. In such form the preparation is subdivided into unit doses containing appropriate quantities of the active component, e.g., dabuzalgron, or an analog, pharmaceutically acceptable salt, or prodrug thereof. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form. The composition can, if desired, also contain other compatible therapeutic agents.

The compounds described herein can be used in combination with one another, with other active agents known to be useful in treating cardiomyopathy, cardiotoxicity, cardiovascular diseases, or with adjunctive agents that may not be effective alone, but may contribute to the efficacy of the active agent.

In another aspect is provided a method of modulating the activity of an α1A adrenergic receptor. The method including contacting the α1A adrenergic receptor with an effective amount of a compound described herein (e.g., dabuzalgron or an analog, pharmaceutically acceptable salt, or prodrug thereof). In embodiments, the modulating the activity of the α1A adrenergic receptor is increasing the activity of the alpha-1 adrenergic receptor. In embodiments, the modulating the activity of the α1A adrenergic receptor is increasing the activity of the α1A adrenergic receptor relative to the absence of the compound (e.g., dabuzalgron or an analog, pharmaceutically acceptable salt, or prodrug thereof). In some embodiments of the method of modulating the activity of an α1A adrenergic receptor, the compound is less effective at modulating the activity of other adrenergic receptors. In some embodiments of the method, the compound modulates the activity of α1A adrenergic receptor at least two-fold more than it modulates the activity of other adrenergic receptors. In some embodiments of the method, the compound modulates the activity of α1A adrenergic receptor at least five-fold more than it modulates the activity of other adrenergic receptors. In some embodiments of the method, the compound modulates the activity of α1A adrenergic receptor at least 10-fold more than it modulates the activity of other adrenergic receptors. In some embodiments of the method, the compound modulates the activity of α1A adrenergic receptor at least 50-fold more than it modulates the activity of other adrenergic receptors. In some embodiments of the method, the compound modulates the activity of α1A adrenergic receptor at least 100-fold more than it modulates the activity of other adrenergic receptors. In some embodiments of the method, the compound modulates the activity of α1A adrenergic receptor at least 1000-fold more than it modulates the activity of other adrenergic receptors. In some embodiments of the method of modulating the activity of an α1A adrenergic receptor, the compound is less effective at modulating the activity of other α1 adrenergic receptors. In some embodiments of the method, the compound modulates the activity of an α1A adrenergic receptor at least two-fold more than it modulates the activity of other al adrenergic receptors. In some embodiments of the method, the compound modulates the activity of an α1A adrenergic receptor at least five-fold more than it modulates the activity of other α1 adrenergic receptors. In some embodiments of the method, the compound modulates the activity of an α1A adrenergic receptor at least 10-fold more than it modulates the activity of other α1 adrenergic receptors. In some embodiments of the method, the compound modulates the activity of an α1A adrenergic receptor at least 50-fold more than it modulates the activity of other α1 adrenergic receptors. In some embodiments of the method, the compound modulates the activity of an α1A adrenergic receptor at least 100-fold more than it modulates the activity of other α1 adrenergic receptors. In some embodiments of the method, the compound modulates the activity of an α1A adrenergic receptor at least 1000-fold more than it modulates the activity of other α1 adrenergic receptors.

In another aspect is provided a method of increasing the activity of an α1A adrenergic receptor. The method including contacting the α1A adrenergic receptor with an effective amount of a compound described herein (e.g., dabuzalgron or an analog, pharmaceutically acceptable salt, or prodrug thereof). In embodiments, increasing the activity of the α1A adrenergic receptor is increasing the activity of the α1A adrenergic receptor relative to the absence of the compound (e.g., dabuzalgron or an analog, pharmaceutically acceptable salt, or prodrug thereof). In some embodiments of the method of increasing the activity of an α1A adrenergic receptor, the compound is less effective at increasing the activity of other adrenergic receptors. In some embodiments of the method, the compound increases the activity of α1A adrenergic receptor at least two-fold more than it increases the activity of other adrenergic receptors. In some embodiments of the method, the compound increases the activity of α1A adrenergic receptor at least five-fold more than it increases the activity of other adrenergic receptors. In some embodiments of the method, the compound increases the activity of α1A adrenergic receptor at least 10-fold more than it increases the activity of other adrenergic receptors. In some embodiments of the method, the compound increases the activity of α1A adrenergic receptor at least 50-fold more than it increases the activity of other adrenergic receptors. In some embodiments of the method, the compound increases the activity of α1A adrenergic receptor at least 100-fold more than it increases the activity of other adrenergic receptors. In some embodiments of the method, the compound increases the activity of α1A adrenergic receptor at least 1000-fold more than it increases the activity of other adrenergic receptors. In some embodiments of the method of increasing the activity of an α1A adrenergic receptor, the compound is less effective at increasing the activity of other α1 adrenergic receptors. In some embodiments of the method, the compound increases the activity of an α1A adrenergic receptor at least two-fold more than it increases the activity of other α1 adrenergic receptors. In some embodiments of the method, the compound increases the activity of an α1A adrenergic receptor at least five-fold more than it increases the activity of other α1 adrenergic receptors. In some embodiments of the method, the compound increases the activity of an α1A adrenergic receptor at least 10-fold more than it increases the activity of other α1 adrenergic receptors. In some embodiments of the method, the compound increases the activity of an α1A adrenergic receptor at least 50-fold more than it increases the activity of other α1 adrenergic receptors. In some embodiments of the method, the compound increases the activity of an α1A adrenergic receptor at least 100-fold more than it increases the activity of other α1 adrenergic receptors. In some embodiments of the method, the compound increases the activity of an α1A adrenergic receptor at least 1000-fold more than it increases the activity of other α1 adrenergic receptors.

In embodiments of the methods described herein the compound (e.g., dabuzalgron or an analog, pharmaceutically acceptable salt, or prodrug thereof) activates ERK. In embodiments of the methods described herein the compound (e.g., dabuzalgron or an analog, pharmaceutically acceptable salt, or prodrug thereof) increases the activity of ERK. In embodiments of the methods described herein, the compound (e.g., dabuzalgron or an analog, pharmaceutically acceptable salt, or prodrug thereof) increases the cytoprotective activity of ERK. In embodiments of the methods described herein the compound (e.g., dabuzalgron or an analog, pharmaceutically acceptable salt, or prodrug thereof) reduces cell death (e.g., cell death associated with anthracycline administration). In embodiments of the methods described herein, the compound (e.g., dabuzalgron or an analog, pharmaceutically acceptable salt, or prodrug thereof) reduces cytochrome c release (e.g., from the membrane, from mitochondria, from mitochondrial membrane). In embodiments of the methods described herein, the compound (e.g., dabuzalgron or an analog, pharmaceutically acceptable salt, or prodrug thereof) mitigates (e.g., reduced or counteracted) reduction or loss of mitochondrial membrane potential. In embodiments of the methods described herein, the compound (e.g., dabuzalgron or an analog, pharmaceutically acceptable salt, or prodrug thereof) prevents heart failure. In embodiments of the methods described herein, the compound (e.g., dabuzalgron or an analog, pharmaceutically acceptable salt, or prodrug thereof) treats heart failure. In embodiments of the methods described herein, the compound (e.g., dabuzalgron or an analog, pharmaceutically acceptable salt, or prodrug thereof) treats systolic heart failure. In embodiments of the methods described herein, the compound (e.g., dabuzalgron or an analog, pharmaceutically acceptable salt, or prodrug thereof) treats cardiomyocyte injury (e.g., associated with anthracycline treatment). In embodiments of the methods described herein, the compound (e.g., dabuzalgron or an analog, pharmaceutically acceptable salt, or prodrug thereof) does not modulate transcription or expression levels of atrial natriuretic peptide, beta myosin heavy chain, or alpha-skeletal actin. In embodiments of the methods described herein, the compound (e.g., dabuzalgron or an analog, pharmaceutically acceptable salt, or prodrug thereof) prevents or treats decrease in contractile function associated with anthracycline treatment. In embodiments of the methods described herein, the compound (e.g., dabuzalgron or an analog, pharmaceutically acceptable salt, or prodrug thereof) treats or prevents cardiac fibrosis (e.g., associated with anthracycline treatment). In embodiments of the methods described herein, the compound (e.g., dabuzalgron or an analog, pharmaceutically acceptable salt, or prodrug thereof) increases levels of cytochrome c oxidase proteins. In embodiments of the methods described herein, the compound (e.g., dabuzalgron or an analog, pharmaceutically acceptable salt, or prodrug thereof) increases levels of complex 1 proteins. In embodiments of the methods described herein, the compound (e.g., dabuzalgron or an analog, pharmaceutically acceptable salt, or prodrug thereof) increases the levels of complex 1 proteins and ATP synthase proteins. In embodiments of the methods described herein, the compound (e.g., dabuzalgron or an analog, pharmaceutically acceptable salt, or prodrug thereof) increases ATP levels in cells (e.g., cardiomyocytes, heart cells, ATP levels in heart cells relative to ATP levels in heart cells associated with anthracycline treatment). In embodiments of the methods described herein, the compound (e.g., dabuzalgron or an analog, pharmaceutically acceptable salt, or prodrug thereof) increases ERK phosphorylation. In embodiments of the methods described herein, the compound (e.g., dabuzalgron or an analog, pharmaceutically acceptable salt, or prodrug thereof) reduces cell death (e.g., apoptosis or necrosis). In embodiments of the methods described herein, the compound (e.g., dabuzalgron or an analog, pharmaceutically acceptable salt, or prodrug thereof) reduces cell death associated with anthracycline treatment (e.g., apoptosis or necrosis). In embodiments of the methods described herein, the compound (e.g., dabuzalgron or an analog, pharmaceutically acceptable salt, or prodrug thereof) reduced cytochrome c release (e.g., associated with anthracycline treatment). In embodiments of the methods described herein, the compound (e.g., dabuzalgron or an analog, pharmaceutically acceptable salt, or prodrug thereof) reduced caspase cleavage or PARP cleavage (e.g., associated with anthracycline treatment). In embodiments of the methods described herein, the compound (e.g., dabuzalgron or an analog, pharmaceutically acceptable salt, or prodrug thereof) does not cause cardiac hypertrophy. In embodiments of the methods described herein, the compound (e.g., dabuzalgron or an analog, pharmaceutically acceptable salt, or prodrug thereof) does not increase blood pressure. In embodiments of the methods described herein, the compound (e.g., dabuzalgron or an analog, pharmaceutically acceptable salt, or prodrug thereof) does not increase heart rate. In embodiments of the methods described herein, the compound (e.g., dabuzalgron or an analog, pharmaceutically acceptable salt, or prodrug thereof) increases the force or energy of muscle contractions (e.g., compared to the absence of the compound). In embodiments of the methods described herein, the compound (e.g., dabuzalgron or an analog, pharmaceutically acceptable salt, or prodrug thereof) increases the activity of ERK (e.g., compared to the absence of the compound). In embodiments of the methods described herein, the compound (e.g., dabuzalgron or an analog, pharmaceutically acceptable salt, or prodrug thereof) increases the activity of MEK (e.g., compared to the absence of the compound).

In another aspect is provided a method of modulating the activity of an α1A adrenergic receptor. The method including contacting the α1A adrenergic receptor with an effective amount of a compound described herein (e.g., dabuzalgron). In embodiments, the modulating the activity of the α1A adrenergic receptor is increasing the activity of the alpha-1 adrenergic receptor. In embodiments, the modulating the activity of the α1A adrenergic receptor is increasing the activity of the α1A adrenergic receptor relative to the absence of the compound (e.g., dabuzalgron). In some embodiments of the method of modulating the activity of an α1A adrenergic receptor, the compound is less effective at modulating the activity of other adrenergic receptors. In some embodiments of the method, the compound modulates the activity of α1A adrenergic receptor at least two-fold more than it modulates the activity of other adrenergic receptors. In some embodiments of the method, the compound modulates the activity of α1A adrenergic receptor at least five-fold more than it modulates the activity of other adrenergic receptors. In some embodiments of the method, the compound modulates the activity of α1A adrenergic receptor at least 10-fold more than it modulates the activity of other adrenergic receptors. In some embodiments of the method, the compound modulates the activity of α1A adrenergic receptor at least 50-fold more than it modulates the activity of other adrenergic receptors. In some embodiments of the method, the compound modulates the activity of α1A adrenergic receptor at least 100-fold more than it modulates the activity of other adrenergic receptors. In some embodiments of the method, the compound modulates the activity of α1A adrenergic receptor at least 1000-fold more than it modulates the activity of other adrenergic receptors. In some embodiments of the method of modulating the activity of an α1A adrenergic receptor, the compound is less effective at modulating the activity of other α1 adrenergic receptors. In some embodiments of the method, the compound modulates the activity of an α1A adrenergic receptor at least two-fold more than it modulates the activity of other α1 adrenergic receptors. In some embodiments of the method, the compound modulates the activity of an α1A adrenergic receptor at least five-fold more than it modulates the activity of other α1 adrenergic receptors. In some embodiments of the method, the compound modulates the activity of an α1A adrenergic receptor at least 10-fold more than it modulates the activity of other α1 adrenergic receptors. In some embodiments of the method, the compound modulates the activity of an α1A adrenergic receptor at least 50-fold more than it modulates the activity of other α1 adrenergic receptors. In some embodiments of the method, the compound modulates the activity of an α1A adrenergic receptor at least 100-fold more than it modulates the activity of other α1 adrenergic receptors. In some embodiments of the method, the compound modulates the activity of an α1A adrenergic receptor at least 1000-fold more than it modulates the activity of other α1 adrenergic receptors.

In another aspect is provided a method of increasing the activity of an α1A adrenergic receptor. The method including contacting the α1A adrenergic receptor with an effective amount of a compound described herein (e.g., dabuzalgron). In embodiments, the increasing the activity of the α1A adrenergic receptor is increasing the activity of the α1A adrenergic receptor relative to the absence of the compound (e.g., dabuzalgron). In some embodiments of the method of increasing the activity of an α1A adrenergic receptor, the compound is less effective at increasing the activity of other adrenergic receptors. In some embodiments of the method, the compound increases the activity of α1A adrenergic receptor at least two-fold more than it increases the activity of other adrenergic receptors. In some embodiments of the method, the compound increases the activity of α1A adrenergic receptor at least five-fold more than it increases the activity of other adrenergic receptors. In some embodiments of the method, the compound increases the activity of α1A adrenergic receptor at least 10-fold more than it increases the activity of other adrenergic receptors. In some embodiments of the method, the compound increases the activity of α1A adrenergic receptor at least 50-fold more than it increases the activity of other adrenergic receptors. In some embodiments of the method, the compound increases the activity of α1A adrenergic receptor at least 100-fold more than it increases the activity of other adrenergic receptors. In some embodiments of the method, the compound increases the activity of α1A adrenergic receptor at least 1000-fold more than it increases the activity of other adrenergic receptors. In some embodiments of the method of increasing the activity of an α1A adrenergic receptor, the compound is less effective at increasing the activity of other α1 adrenergic receptors. In some embodiments of the method, the compound increases the activity of an α1A adrenergic receptor at least two-fold more than it increases the activity of other α1 adrenergic receptors. In some embodiments of the method, the compound increases the activity of an α1A adrenergic receptor at least five-fold more than it increases the activity of other α1 adrenergic receptors. In some embodiments of the method, the compound increases the activity of an α1A adrenergic receptor at least 10-fold more than it increases the activity of other α1 adrenergic receptors. In some embodiments of the method, the compound increases the activity of an α1A adrenergic receptor at least 50-fold more than it increases the activity of other α1 adrenergic receptors. In some embodiments of the method, the compound increases the activity of an α1A adrenergic receptor at least 100-fold more than it increases the activity of other α1 adrenergic receptors. In some embodiments of the method, the compound increases the activity of an α1A adrenergic receptor at least 1000-fold more than it increases the activity of other α1 adrenergic receptors.

In embodiments of the methods described herein the compound (e.g., dabuzalgron) activates ERK. In embodiments of the methods described herein the compound (e.g., dabuzalgron) increases the activity of ERK. In embodiments of the methods described herein, the compound (e.g., dabuzalgron) increases the cytoprotective activity of ERK. In embodiments of the methods described herein the compound (e.g., dabuzalgron) reduces cell death (e.g., cell death associated with anthracycline administration). In embodiments of the methods described herein, the compound (e.g., dabuzalgron) reduces cytochrome c release (e.g., from the membrane, from mitochondria, from mitochondrial membrane). In embodiments of the methods described herein, the compound (e.g., dabuzalgron) mitigates (e.g., reduced or counteracted) reduction or loss of mitochondrial membrane potential. In embodiments of the methods described herein, the compound (e.g., dabuzalgron) prevents heart failure. In embodiments of the methods described herein, the compound (e.g., dabuzalgron) treats heart failure. In embodiments of the methods described herein, the compound (e.g., dabuzalgron) treats systolic heart failure. In embodiments of the methods described herein, the compound (e.g., dabuzalgron) treats cardiomyocyte injury (e.g., associated with anthracycline treatment). In embodiments of the methods described herein, the compound (e.g., dabuzalgron) does not modulate transcription or expression levels of atrial natriuretic peptide, beta myosin heavy chain, or alpha-skeletal actin. In embodiments of the methods described herein, the compound (e.g., dabuzalgron) prevents or treats decrease in contractile function associated with anthracycline treatment. In embodiments of the methods described herein, the compound (e.g., dabuzalgron) treats or prevents cardiac fibrosis (e.g., associated with anthracycline treatment). In embodiments of the methods described herein, the compound (e.g., dabuzalgron) increases levels of cytochrome c oxidase proteins. In embodiments of the methods described herein, the compound (e.g., dabuzalgron) increases levels of complex 1 proteins. In embodiments of the methods described herein, the compound (e.g., dabuzalgron) increases the levels of complex 1 proteins and ATP synthase proteins. In embodiments of the methods described herein, the compound (e.g., dabuzalgron) increases ATP levels in cells (e.g., cardiomyocytes, heart cells, ATP levels in heart cells relative to ATP levels in heart cells associated with anthracycline treatment). In embodiments of the methods described herein, the compound (e.g., dabuzalgron) increases ERK phosphorylation. In embodiments of the methods described herein, the compound (e.g., dabuzalgron) reduces cell death (e.g., apoptosis or necrosis). In embodiments of the methods described herein, the compound (e.g., dabuzalgron) reduces cell death associated with anthracycline treatment (e.g., apoptosis or necrosis). In embodiments of the methods described herein, the compound (e.g., dabuzalgron) reduced cytochrome c release (e.g., associated with anthracycline treatment). In embodiments of the methods described herein, the compound (e.g., dabuzalgron) reduced caspase cleavage or PARP cleavage (e.g., associated with anthracycline treatment). In embodiments of the methods described herein, the compound (e.g., dabuzalgron) does not cause cardiac hypertrophy. In embodiments of the methods described herein, the compound (e.g., dabuzalgron) does not increase blood pressure. In embodiments of the methods described herein, the compound (e.g., dabuzalgron) does not increase heart rate. In embodiments of the methods described herein, the compound (e.g., dabuzalgron) increases the force or energy of muscle contractions (e.g., compared to the absence of the compound). In embodiments of the methods described herein, the compound (e.g., dabuzalgron) increases the activity of ERK (e.g., compared to the absence of the compound). In embodiments of the methods described herein, the compound (e.g., dabuzalgron) increases the activity of MEK (e.g., compared to the absence of the compound).

III. Additional Embodiments

Embodiment P1

A method of treating or preventing cardiomyopathy in a subject in need of such treatment, said method comprising administering a therapeutically or prophylactically effective amount of dabuzalgron, or an analog, pharmaceutically acceptable salt, or prodrug thereof.

Embodiment P2

The method of embodiment P1, wherein said cardiomyopathy is associated with anthracycline administration, hypertension, heart valve disease, myocardial ischemia, myocardial infarction, myocardial inflammation, heart failure, pulmonary hypertension, myocardial stunning, myocardial hibernation, cardiac surgery, genetic mutation, genetic changes in cardiac proteins, or coronary intervention.

Embodiment P3

The method of embodiment P1, wherein said cardiomyopathy is associated with anthracycline administration.

Embodiment P4

The method of embodiment P3, wherein said anthracycline is doxorubicin, daunorubicin, epirubicin, idarubucin, adriamycin, or valrubicin.

Embodiment P5

The method of one of embodiments P2 to P4, wherein the dabuzalgron, or an analog, pharmaceutically acceptable salt, or prodrug thereof, is co-administered with the anthracycline.

Embodiment P6

The method of one of embodiments P1 to P4, wherein the dabuzalgron, or an analog, pharmaceutically acceptable salt, or prodrug thereof, is administered before administration of the anthracycline.

Embodiment P7

The method of one of embodiments P1 to P4, wherein the dabuzalgron, or an analog, pharmaceutically acceptable salt, or prodrug thereof, is administered after administration of the anthracycline.

Embodiment P8

The method of one of embodiments P1 to P7, wherein said method comprises treating said cardiomyopathy.

Embodiment P9

The method of one of embodiments P1 to P7, wherein said method comprises preventing said cardiomyopathy.

Embodiment P10

The method of one of embodiments P1 to P9, wherein said patient's blood pressure does not increase as a result of said administration.

Embodiment P11

The method of one of embodiments P1 to P9, wherein said patient's blood pressure increases by an amount equal to or less than 50, 40, 30, 20, 10, 9, 8, 7, 6, 5, 4, 3, 2, or 1 mmHg as a result of said administration.

Embodiment P12

The method of embodiment P11, wherein said blood pressure is systolic blood pressure.

Embodiment P13

The method of one of embodiments P1 to P12, wherein said effective amount is between about 0.001 and 1000, 0.1 and 100, 1 and 50, or 5 and 25 micrograms/kilogram patient weight.

Embodiment P14

The method of one of embodiments P1 to P12, wherein said effective amount is about 20 micrograms/kilogram patient weight.

Embodiment P15

The method of one of embodiments P1 to P12, wherein said effective amount is 20 micrograms/kilogram patient weight Embodiment P16

The method of one of embodiments P1 to P15, wherein said effective amount is the total amount administered to said patient in a day.

Embodiment P17

The method of one of embodiments P1 to P16, wherein said administering is parenteral, intravenous, intraarterial, buccal, sublingual, oral, peroral, transdermal, or nasal.

Embodiment P18

A method of treating or preventing cardiac cell mitochondria dysfunction, said method comprising contacting the cardiac cell with an effective amount of dabuzalgron, or an analog, pharmaceutically acceptable salt, or prodrug thereof.

Embodiment P19

A method of treating or preventing cardiac cell death, said method comprising contacting the cardiac cell with an effective amount of dabuzalgron, or an analog, pharmaceutically acceptable salt, or prodrug thereof.

Embodiment P20

The method of embodiment P19, wherein the cardiac cell death is apoptosis.

Embodiment P21

The method of embodiment P19, wherein the cardiac cell death is necrosis.

Embodiment P22

A method of treating or preventing heart failure in a patient in need of such treatment, said method comprising administering a therapeutically or prophylactically effective amount of dabuzalgron, or an analog, pharmaceutically acceptable salt, or prodrug thereof.

IV. Further Embodiments

Embodiment 1

A method of treating or preventing cardiomyopathy in a subject in need of such treatment, said method comprising administering a therapeutically or prophylactically effective amount of dabuzalgron, or an analog, pharmaceutically acceptable salt, or prodrug thereof.

Embodiment 2

The method of embodiment 1, wherein said cardiomyopathy is associated with anthracycline administration, hypertension, heart valve disease, myocardial ischemia, myocardial infarction, myocardial inflammation, heart failure, pulmonary hypertension, myocardial stunning, myocardial hibernation, cardiac surgery, genetic mutation, genetic changes in cardiac proteins, or coronary intervention.

Embodiment 3

The method of embodiment 1, wherein said cardiomyopathy is associated with anthracycline administration.

Embodiment 4

The method of embodiment 3, wherein said anthracycline is doxorubicin, daunorubicin, epirubicin, idarubicin, adriamycin, or valrubicin.

Embodiment 5

The method of one of embodiments 2 to 4, wherein the dabuzalgron, or an analog, pharmaceutically acceptable salt, or prodrug thereof (e.g., dabuzalgron), is co-administered with the anthracycline.

Embodiment 6

The method of one of embodiments 1 to 4, wherein the dabuzalgron, or an analog, pharmaceutically acceptable salt, or prodrug thereof (e.g., dabuzalgron), is administered before administration of the anthracycline.

Embodiment 7

The method of one of embodiments 1 to 4, wherein the dabuzalgron, or an analog, pharmaceutically acceptable salt, or prodrug thereof (e.g., dabuzalgron), is administered after administration of the anthracycline.

Embodiment 8

The method of one of embodiments 1 to 7, wherein said method comprises treating said cardiomyopathy (e.g., but not preventing).

Embodiment 9

The method of one of embodiments 1 to 7, wherein said method comprises preventing said cardiomyopathy (e.g., but not treating).

Embodiment 10

The method of one of embodiments 1 to 9, wherein said patient's blood pressure does not increase as a result of said administration.

Embodiment 11

The method of one of embodiments 1 to 9, wherein said patient's blood pressure increases by an amount equal to or less than 50, 40, 30, 20, 10, 9, 8, 7, 6, 5, 4, 3, 2, or 1 mmHg as a result of said administration.

Embodiment 12

The method of embodiment 11, wherein said blood pressure is systolic blood pressure.

Embodiment 13

The method of one of embodiments 1 to 12, wherein said effective amount is between about 0.001 and 1000, 0.1 and 100, 1 and 50, or 5 and 25 micrograms/kilogram patient weight.

Embodiment 14

The method of one of embodiments 1 to 12, wherein said effective amount is about 20 micrograms/kilogram patient weight.

Embodiment 15

The method of one of embodiments 1 to 12, wherein said effective amount is 20 micrograms/kilogram patient weight Embodiment 16

The method of one of embodiments 1 to 15, wherein said effective amount is the total amount administered to said patient in a day.

Embodiment 17

The method of one of embodiments 1 to 16, wherein said administering is parenteral, intravenous, intraarterial, buccal, sublingual, oral, peroral, transdermal, or nasal.

Embodiment 18

A method of treating or preventing cardiac cell mitochondria dysfunction, said method comprising contacting the cardiac cell with an effective amount of dabuzalgron, or an analog, pharmaceutically acceptable salt, or prodrug thereof.

Embodiment 19

A method of treating or preventing cardiac cell death, said method comprising contacting the cardiac cell with an effective amount of dabuzalgron, or an analog, pharmaceutically acceptable salt, or prodrug thereof.

Embodiment 20

The method of embodiment 19, wherein the cardiac cell death is apoptosis.

Embodiment 21

The method of embodiment 19, wherein the cardiac cell death is necrosis.

Embodiment 22

A method of treating or preventing heart failure in a patient in need of such treatment, said method comprising administering a therapeutically or prophylactically effective amount of dabuzalgron, or an analog, pharmaceutically acceptable salt, or prodrug thereof (e.g., dabuzalgron).

V. Examples

There are three alpha-1 adrenergic receptor (α1-AR) subtypes: A, B, and D. The α1A and B are found in the myocardium, whereas the α1D predominates in coronary arteries. The oral α1A-AR agonist, dabuzalgron, was well tolerated in multiple clinical trials of treatment for urinary incontinence, but development was halted due to lack of efficacy. Doxorubicin (DOX) is a widely used antineoplastic agent with dose-limiting cardiotoxicity that can lead to heart failure. Treatment options for DOX-induced cardiotoxicity are limited. Mice lacking the α1A-AR (AKO) and wild type (WT) littermates were treated with DOX, then an oral subpressor, non-hypertrophic dose of dabuzalgron or vehicle for 7 days. Dabuzalgron preserved contractile function and limited cardiac fibrosis in DOX-treated WT mice. AKO mice had worse survival and contractile function after DOX; neither was improved by dabuzalgron. RNAseq on DOX-treated heart tissue identified dabuzalgron-mediated differences in pathways related to mitochondrial function and energy production, and dabuzalgron preserved cardiac ATP production after DOX. These beneficial effects were abrogated by ERK1/2 inhibition with trametinib. In cardiomyocytes, dabuzalgron protected against DOX-induced cell death and preserved mitochondrial membrane potential. Selective activation of the α1A-AR with the well-tolerated oral agonist dabuzalgron prevents DOX cardiotoxicity, likely due in part to preservation of mitochondrial function in cardiomyocytes. Alpha-1-adrenergic receptor agonists can be used for the prevention and treatment of heart muscle injuries and diseases. One part of the invention is to use a drug or drugs that activate alpha-1 adrenergic receptors in cardiac muscle cells or other cardiac cells, to treat heart muscle diseases, or to prevent heart muscle disease from occurring. Diseases treated by giving an alpha-1 adrenergic agonist after the disease is present would include, but not be limited to: cardiotoxicity, heart failure; cardiomyopathy from hypertension or valve disease or ischemia or idiopathic; myocardial stunning; myocardial hibernation; myocardial dysfunction post-myocardial infarction; myocardial dysfunction post-cardiac surgery; myocardial dysfunction post-coronary intervention; anthracycline-induced cardiomyopathy; other cancer chemotherapy-induced cardiomyopathy; right ventricle failure from pulmonary hypertension or other causes. Diseases prevented by giving an alpha-1-adrenergic agonist before the disease is present would be the same, with two specific examples being anthracycline-induced cardiomyopathy and preconditioning before coronary intervention or bypass or other invasive procedures.

For all cardiac indications, a drug or drugs would be given to activate alpha-1-adrenergic receptors, receptors that normally are activated by catecholamines such as norepinephrine or epinephrine. The drug might activate all subtypes of alpha-1-adrenergic receptor (there are currently 3 known subtypes), or only one or two of the subtypes, or only a particular active state of the subtype (receptors have multiple active states). The effect of the drug would be to increase post-receptor signaling in the cell, for example the cardiac muscle cell, and this increased signaling would have beneficial effects in the heart by increasing beneficial anabolic or trophic or metabolic processes, or by stimulating mechanisms that protect from cell injury or death, or by increasing cardiogenesis. The therapeutic potential of α1A activation in the heart has not been explored well. Doxorubicin (DOX) is a widely used antineoplastic agent with dose-limiting cardiotoxicity that can lead to heart failure. Treatment options for DOX-induced cardiotoxicity are limited. The selective oral α1A agonist dabuzalgron was well tolerated in clinical trials, but development was halted due to lack of efficacy in the treatment of urinary incontinence. In some embodiments, the drug or compound (e.g. dabuzalgron) and/or methods described herein bind to the alpha-1A subtype.

Another mechanism of benefit, in addition to the trophic and protective mechanisms described herein above, is to stimulate acute adaptive processes. This includes improving cardiac function by activating contraction.

Example 1

An Oral Selective Alpha-1A Adrenergic Receptor Agonist Prevents Doxorubicin Cardiotoxicity Mice were treated with DOX followed by a subpressor and non-hypertrophic dose of dabuzalgron or vehicle by mouth for 7 days. Treatment with dabuzalgron preserved contractile function and limited fibrosis in wild type mice but had no effect in mice lacking the α1A-AR. RNAseq on heart tissue identified differences in pathways related to mitochondrial function and energy production and dabuzalgron preserved ATP production after DOX. In cardiomyocytes, dabuzalgron activated cytoprotective ERK, protected against DOX-induced cell death, decreased cytochrome c release and apoptotic effectors, and mitigated loss of mitochondrial membrane potential. Selective activation of the α1A-AR with the well-tolerated oral agonist dabuzalgron prevents doxorubicin (DOX) cardiotoxicity, likely due in part to preservation of mitochondrial function in cardiomyocytes.

Evidence from numerous studies in cells and animals indicates that alpha-1 adrenergic receptors (α1-ARs) play numerous protective roles in the heart. [1] There are three α1-AR subtypes: α1A, α1B, and α1D. In rodent and human myocardium, the α1A and α1B predominate and there is no measurable α1D. The α1D is the major α1-AR subtype in human and mouse coronary arteries, where its activation promotes vasoconstriction. [2,3] The role of the α1B remains unclear, but multiple lines of evidence suggest that the cardioprotective effects of non-selective α1-AR agonists are mediated by the α1A. Mice overexpressing the α1A have increased contractility,[4] and are protected from ischemia-reperfusion injury,[5] myocardial infarction,[6] and transverse aortic constriction.[7] Abrogation of these beneficial processes may also account for the two-fold increase in incident heart failure (HF) in hypertensive patients treated with the non-selective doxazosin in ALLHAT. [8] This and other evidence from animal and human studies suggest that activating myocardial α1-ARs could be therapeutically effective in HF.

In this study, we used the selective α1A agonist dabuzalgron to test our hypothesis that selective stimulation of myocardial α1As could confer cardioprotection without increasing afterload through vascular α1-AR activation. Dabuzalgron (also referred to herein as Ro 115-1240, or 1240) was developed for the treatment of urinary incontinence. It showed excellent α1A selectivity in preclinical testing[9] and was well tolerated by a total of 1,223 women in a Phase 1 trial (11) two Phase 2 randomized multicenter trials; (Roche NN16378 and NN16691, roche-trials.com) and a subsequent open-label study. (Roche NN16586) Importantly, there were no significant changes in BP in the subjects who received dabuzalgron in any of these trials, suggesting that the chosen dose did not affect vascular tone. When interim analysis of the Phase 2 trials revealed no clinically meaningful difference in urinary incontinence between the dabuzalgron and placebo groups, enrollment was closed and further development of dabuzalgron was halted.

We chose initially to test the therapeutic efficacy of dabuzalgron using an anthracycline injury model.[11-13] Anthracyclines, including DOX, are highly effective and commonly used chemotherapeutic agents, but have dose-limiting cardiotoxicity. Though the incidence of anthracycline-induced cardiomyopathy has declined with contemporary dosing regimens, left ventricular dysfunction still occurs in 20-30% of anthracycline recipients [14, 15] and remains an important cause of systolic HF. Numerous mechanisms contribute to cardiomyocyte injury after anthracycline administration, but mitochrondrial dysfunction and broad deficits in cardiomyocyte energy production are central to the pathogenesis.[16]

We show that dabuzalgron protects against the cardiotoxic effects of DOX in vitro and in vivo by activating the α1A-AR and demonstrate that the preservation of mitochondrial function is one novel mechanism underlying this benefit.

Example 2

Selective α1-AR Activation with Dabuzalgron does not Affect Heart Rate, Blood Pressure, or Heart Size in Wild Type Mice Given that non-selective α1-AR agonists such as phenylephrine can increase BP and cause cardiomyocyte hypertrophy, we sought to determine whether the selective α1A agonist, dabuzalgron, would have similar effects. Untreated mice were trained on the tail cuff apparatus daily for 5 days. On Days 6-10, mice received dabuzalgron (1-100 µg/kg/day) or vehicle by gavage twice daily for 5 days with daily BP measurements. After 5 days, there was no difference in systolic BP or HR between mice treated with vehicle and mice treated with any dose of dabuzalgron (FIG. 1A).

Figure 1B:
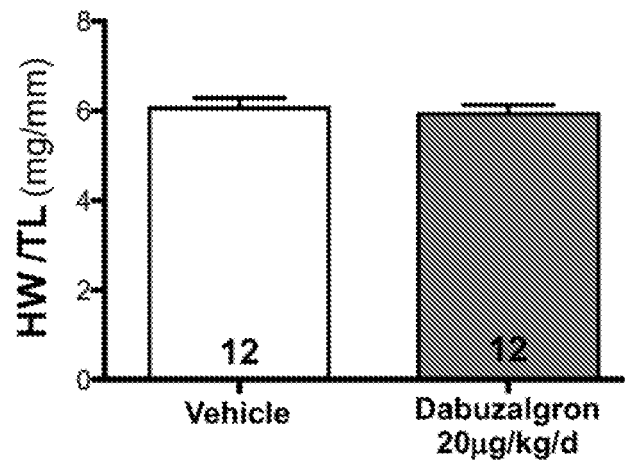

To test the effect of an α1A agonist on cardiac hypertrophy, we administered dabuzalgron (1-100 µg/kg/day) or vehicle by gavage twice daily for 7 days. There was no measurable change in body weight or heart weight at any dose (Table 1), and no difference in heart weight indexed to tibia length could be found when comparing wild type mice treated with dabuzalgron and water. (FIG. 1B). Collectively these findings suggest that the chosen doses of dabulzagron do not increase vascular tone or promote cardiac hypertrophy, two properties attributed to non-selective α1-AR activation.

TABLE 1

Indexed heart weight after 7-day gavage treatment with dabuzalgron (Ro 115-1240) in uninjured mice.

| Ro 115-1240 µg/kg/day (n) Wild type | Body weight, initial (g) | Body weight, final (g) | Tibia length (mm) | Heart weight (mg) | Heart/body weight (%) | Heart weight/ tibia length (mg/mm) |
|---|---|---|---|---|---|---|
| Vehicle (12) | 27.2 ± 1.0 | 26.9 ± 0.8 | 17.5 ± 0.2 | 109 ± 4 | 0.40 ± 0.01 | 6.2 ± 0.2 |
| 0.2 (3) | 25.5 ± 0.3 | 25.3 ± 0.4 | 17.3 ± 0.1 | 106 ± 4 | 0.42 ± 0.01 | 6.1 ± 0.3 |
| 2 (6) | 26.0 ± 0.8 | 25.9 ± 0.8 | 17.5 ± 0.1 | 106 ± 4 | 0.41 ± 0.02 | 6.1 ± 0.2 |
| 20 (12) | 27.9 ± 1.2 | 27.3 ± 1.1 | 17.5 ± 0.1 | 110 ± 4 | 0.41 ± 0.01 | 5.9 ± 0.2 |
| 200 (7) | 28.4 ± 1.8 | 27.4 ± 1.6 | 17.6 ± 0.2 | 113 ± 6 | 0.41 ± 0.01 | 6.1 ± 0.3 |

All values are mean ± SEM, n given in parentheses

Figure 1C:
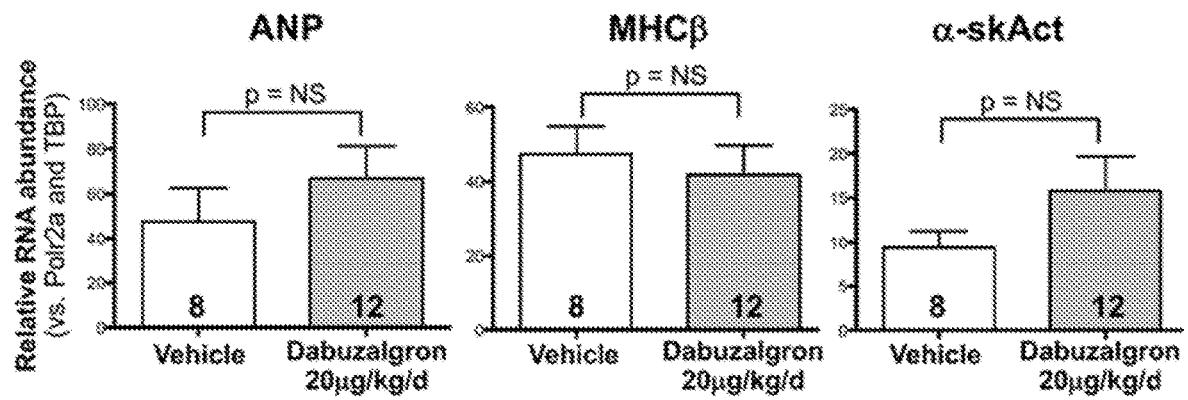

We used qRT-PCR to assay traditionally accepted molecular markers of hypertrophy in the hearts of mice treated with dabuzalgron. There was no change in the transcript abundance of atrial natriuretic peptide, beta myosin heavy chain, or alpha-skeletal actin. (FIG. 1C)

Example 3

Dabuzalgron Protects Against Doxorubicin Cardiotoxicity by Activating the α1A-AR To test whether therapeutic activation of the α1A could prevent DOX-induced cardiac injury, we treated WT mice and mice lacking the α1A (AKO) with DOX 20 mg/kg intraperitoneal (i.p.) injection followed by 7 days gavage with either water or dabuzalgron 10 µg/kg twice daily. (FIG. 2A) There was no difference in baseline heart weight in WT and AKO mice. (Table 2) All animals treated with DOX lost 10-15% of their body weight. Raw heart weight and heart weight indexed to tibia length were lower in mice treated with DOX than in vehicle-treated WT and AKO controls. (Table 2) Survival was 78% in wild type mice treated with DOX and 86% (p=NS by Fisher's exact test) in mice treated with DOX and gavaged with dabuzalgron. Survival in 16 AKO mice treated with DOX was 38% (p=0.08 vs. DOX-treated WT mice by Fisher's exact test) and unaffected by dabuzalgron administration.

Previous studies in rodents(20) and humans(21) have demonstrated that □1-AR activation increases inotropy in failing heart tissue, though has minimal effects on contractility of the uninjured heart. Conscious echocardiography on Day 7 after DOX treatment in WT mice revealed a decrease in contractile function that was prevented by administration of dabuzalgron. (FIG. 2B, Table 3) Fractional shortening and left ventricular end systolic volume both were preserved in animals that received dabuzalgron after DOX, (Table 3)

TABLE 2

Indexed heart weight after 7-day doxorubicin treatment with or without dabuzalgron (Ro 115-1240) 20 µg/kg/d.

| Treatment | 7-day survival | Body Wt Day 0 (g) | Body Wt Day 7 (g) | Tibia (mm) | Heart Wt (mg) | HW/BW (%) | HW/TL (mg/mm) | Lung Wt/TL (mg/mm) |
|---|---|---|---|---|---|---|---|---|
| WILD TYPE | | | | | | | | |
| Vehicle (12) | 100% | 27.3 ± 0.6 | 27.8 ± 0.6 | 17.2 ± 0.1 | 126 ± 3 | 0.45 ± 0.01 | 7.3 ± 0.2 | 7.1 ± 1.2 |
| Dox + vehicle (14) | 78% | 28.1 ± 0.7 | 25.1 ± 1.2* | 17.9 ± 0.2 | 104 ± 7* | 0.41 ± 0.01* | 5.8 ± 0.4* | 8.2 ± 0.3 |
| Dox + dabuzalgron (14) | 86% | 27.3 ± 0.5 | 24.3 ± 0.6* | 17.6 ± 0.1 | 97 ± 5* | 0.41 ± 0.02* | 5.5 ± 0.3* | 7.7 ± 0.4 |
| α1A-KO | | | | | | | | |
| Vehicle (3) | 100% | 26.7 ± 0.9 | 26.7 ± 0.9 | 17.0 ± 0.0 | 118 ± 7 | 0.44 ± 0.02 | 6.9 ± 0.4 | 5.2 ± 0.3 |
| Dox + vehicle (3) | 38% | 29.9 ± 0.7 | 26.8 ± 1.2 | 17.5 ± 0.3 | 101 ± 9 | 0.42 ± 0.02 | 5.8 ± 0.3* | 5.0 ± 0.3 |
| Dox + dabuzalgron (4) | 50% | 29.3 ± 0.6 | 26.4 ± 1.2 | 17.4 ± 0.1 | 101 ± 5* | 0.39 ± 0.01* | 5.6 ± 0.2* | 5.1 ± 0.2 |

All values are mean ± SEM, n given in parentheses.
Anatomic data are included only for mice that survived 7 days.
HW = heart weight;
BW = body weight;
TL = tibia length;
Wt = weight DOX treatment decreased survival and this decrease was not fully mitigated by treatment with dabuzalgron in this experiment and over this time period. Survival in AKO mice treated with DOX was 50% and unaffected by dabuzalgron administration, as seen in Table 2.

Figure 2A:
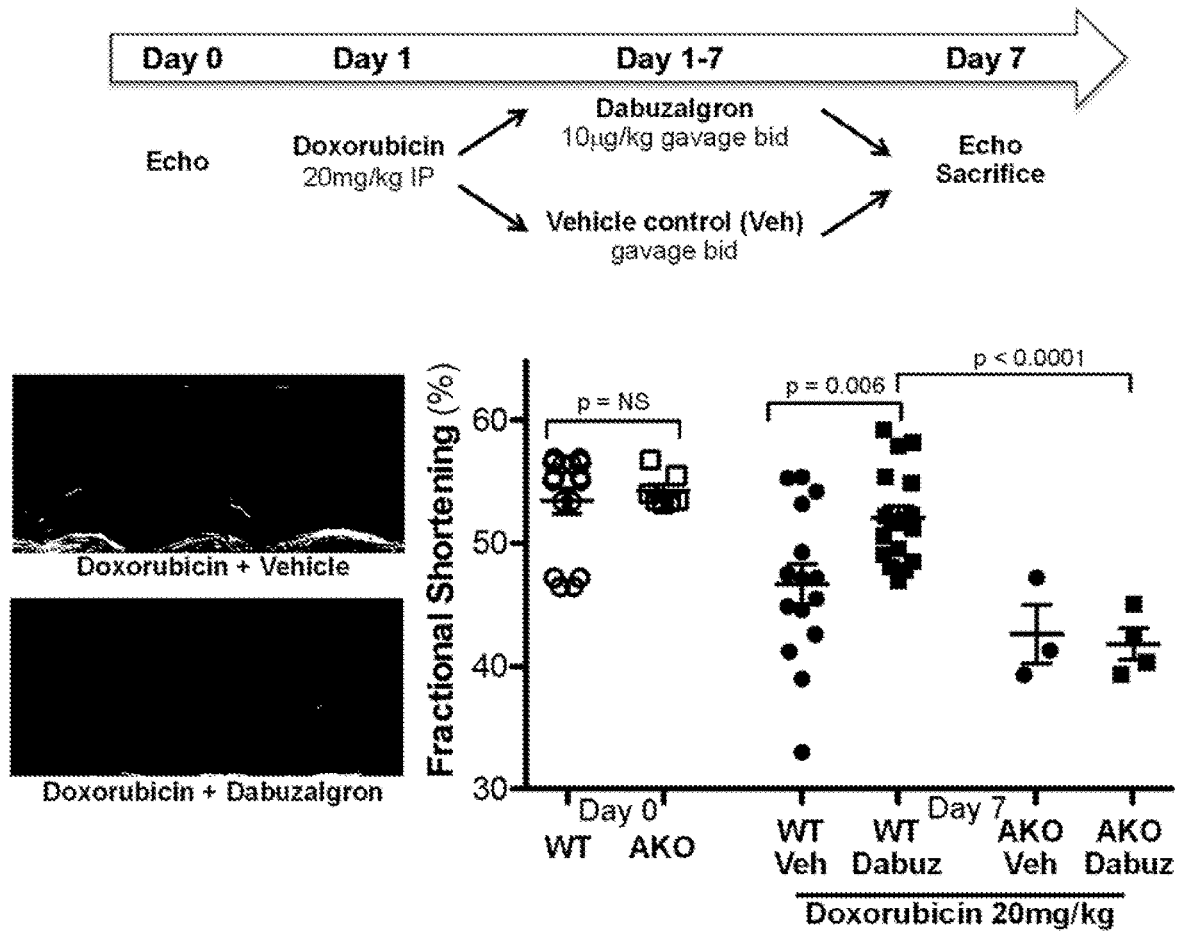
FIGS. 2A-2B. Dabuzalgron protects mice against doxorubicin cardiotoxicity by activating the $\alpha$1A-AR. Wild type (WT) mice and knockout mice lacking the $\alpha$1A-AR (AKO) underwent baseline echocardiography, then received either DOX 20 mg/kg or vehicle control (VC, phosphate buffered saline) by a single i.p. injection followed by 7 days of treatment with either dabuzalgron 10 µg/kg or water by gavage twice daily. On Day 7 the mice underwent echocardiography prior to sacrifice.
Figure 2B:
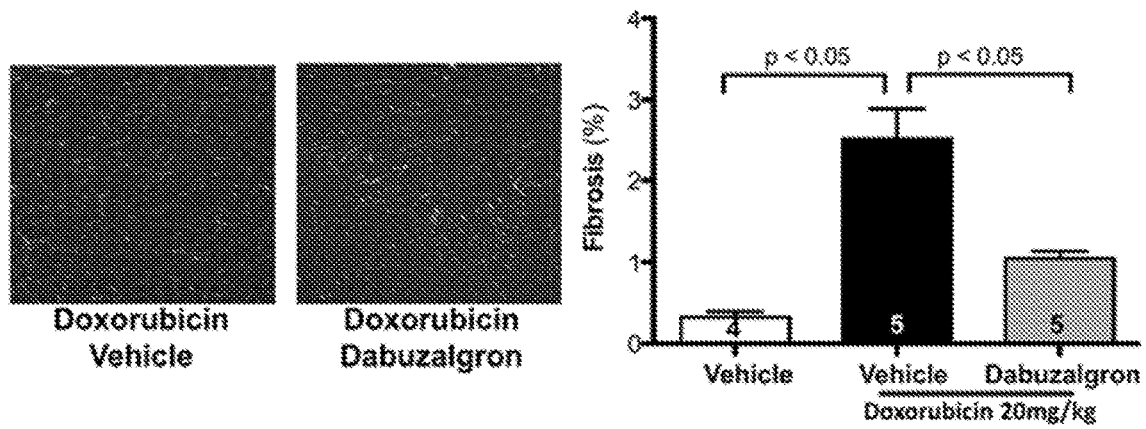

Conscious echocardiography on Day 7 revealed a decrease in contractile function after DOX treatment in WT mice that was prevented by administration of dabuzalgron. (FIG. 2A, Table 3)

though dabuzalgron had no effect on echocardiographic parameters in uninjured mice. There was no difference in baseline contractile function of WT and AKO mice. (FIG. 2B) However, the surviving DOX-treated AKO mice had significantly lower fractional shortening than DOX-treated WT mice. ($p<0.01$, FIG. 2B) This profound reduction in contractile function was not rescued by dabuzalgron. (FIG. 2B) The burden of fibrosis as detected by Masson Trichrome increased significantly after DOX, (FIG. 2C) but treatment with dabuzalgron mitigated this increase.

TABLE 3

Echocardiographic parameters after doxorubicin treatment with or without dabuzalgron (Ro 115-1240) 20 µg/kg/d.

| | HR | LVIDd | LVIDs | FS | LVd vol | LVs vol | IVSd | PWd |
|---|---|---|---|---|---|---|---|---|
| WILD TYPE | | | | | | | | |
| Dox + vehicle (14) Day 0 | 658 ± 30 | 2.9 ± 0.1 | 1.4 ± 0.1 | 54 ± 2 | 34 ± 4 | 5 ± 1 | 0.9 ± 0 | 0.8 ± 0 |
| Day 7 | 613 ± 23 | 2.8 ± 0.1 | 1.5 ± 0.1 | 46 ± 2 | 31 ± 3 | 7 ± 2 | 0.9 ± 0 | 0.8 ± 0 |
| Dox + 1240 (14) Day 0 | 630 ± 59 | 3.0 ± 0.2 | 1.4 ± 0.1 | 50 ± 3 | 36 ± 6 | 5 ± 1 | 0.9 ± 0.1 | 0.9 ± 0 |
| Day 7 | 667 ± 10* | 2.8 ± 0.1 | 1.3 ± 0* | 53 ± 1* | 31 ± 2 | 5 ± 0* | 0.9 ± 0 | 0.9 ± 0 |
| α1A-KO | | | | | | | | |
| Dox + vehicle (3) Day 0 | 679 ± 38 | 3.0 ± 0.1 | 1.3 ± 0.0 | 55 ± 1 | 34 ± 2 | 5 ± 0 | 1.1 ± 0.1 | 1.1 ± 0.1 |
| Day 7 | 661 ± 21 | 3.0 ± 0.2 | 1.7 ± 0.1 | 43 ± 2 | 34 ± 4 | 9 ± 2 | 1.2 ± 0.0 | 1.1 ± 0.0 |
| Dox + 1240 (3) Day 0 | 703 ± 13 | 2.8 ± 0.1 | 1.3 ± 0.1 | 54 ± 1 | 30 ± 3 | 4 ± 1 | 1.1 ± 0.0 | 1.1 ± 0.1 |
| Day 7 | 618 ± 19 | 2.8 ± 0.1 | 1.6 ± 0.0 | 42 ± 2 | 29 ± 2 | 8 ± 1 | 1.1 ± 0.0 | 1.1 ± 0.1 |

2D guided M-mode echocardiography was performed on unanesthetized mice, n given in parentheses.
All values are mean ± SEM,
*$p < 0.05$ vs. Dox + vehicle.
FS = Fractional Shortening (%); HR = Heart Rate (beats per minute); IVSd = Interventricular Septal thickness, diastole (cm); LVd vol = Left Ventricular diastolic volume (mL); LVs vol = Left Ventricular systolic volume (mL); LVIDd = Left Ventricular Internal Diameter, diastole (cm); LVIDs = Left Ventricular Internal Diameter, systole (cm); LVm = LV mass, calculated; PWd = Posterior Wall, diastole (cm).

In summary, treatment with dabuzalgron preserved contractile function and reduced fibrosis after DOX administration. AKO mice treated with DOX had worse survival and more profoundly impaired contractile function than WT mice. Neither parameter was affected by dabulzagron in AKOs, indicating that the beneficial effects of dabulzagron require the presence of the α1A.

Example 4

Dabuzalgron Preserves In Vivo Abundance of Mitochondrial Function Transcripts, Upregulates PGC1α, and Restores ATP Synthesis after Treatment with Doxorubicin To investigate the mechanisms behind dabuzalgron's cardioprotective effects after DOX, we used RNAseq to analyze heart tissue from mice treated with DOX with and without dabuzalgron. An omnibus test of transcript abundance across all groups was performed with DESeq2 with groups encoded as categorical variables. One hundred-one genes were identified as significant by meeting the q<0.05 threshold (the set of genes with a 5% false discovery rate). Note, genes of potential interest can be found in Table 4.

TABLE 4

Genes of potential interest

| Gene | Base Mean | log2FoldChange | lfcSE | stat | pvalue | padj |
|---|---|---|---|---|---|---|
| Cox7a1\|12865 | 341 | 0.5 | 0.2 | 39.1 | 0 | 1.61E−06 |
| Myl2\|17906 | 28101 | 0.43 | 0.14 | 38.4 | 0 | 1.61E−06 |
| Aqp1\|11826 | 318 | 0.97 | 0.2 | 35.7 | 0 | 3.79E−06 |
| Atp5k\|11958 | 362 | 0.37 | 0.16 | 30.4 | 0 | 4.44E−05 |
| Fhl2\|14200 | 790 | 0.19 | 0.2 | 27.8 | 0 | 0.00011 |
| Atp5j2\|57423 | 337 | 0.36 | 0.17 | 27.7 | 0 | 0.00011 |
| Cox7b\|66142 | 421 | 0.58 | 0.16 | 28.3 | 0 | 0.00011 |
| Cox6b1\|110323 | 805 | 0.44 | 0.13 | 28.1 | 0 | 0.00011 |
| Fabp4\|11770 | 560 | 0 | 0.15 | 25.8 | 0 | 0.00021 |
| Enah\|13800 | 99 | −0.72 | 0.22 | 25.7 | 0 | 0.00021 |
| Gm12070 | 375 | 0.17 | 0.15 | 25.5 | 0 | 0.00022 |
| Apoe\|11816 | 197 | −0.22 | 0.18 | 25.3 | 0 | 0.00023 |
| Ttll1\|319953 | 189 | 0.17 | 0.17 | 24.8 | 0 | 0.00028 |
| Rrad\|56437 | 84 | −1.1 | 0.27 | 23.5 | 0 | 0.0005 |
| Armc2\|213402 | 142 | 0.09 | 0.19 | 23.2 | 0 | 0.00054 |
| Fabp3\|14077 | 3374 | −0.14 | 0.16 | 22.9 | 0 | 0.00059 |
| Actb\|11461 | 194 | 0.31 | 0.22 | 21.8 | 0 | 0.00101 |
| Atp5g1\|11951 | 590 | 0.48 | 0.16 | 20.9 | 0 | 0.00152 |
| Sesn1\|140742 | 85 | 1.07 | 0.24 | 19.7 | 0.0001 | 0.00229 |
| Tpm1\|22003 | 27599 | 0.47 | 0.2 | 19.8 | 0.0001 | 0.00229 |
| Gm12070\|654472 | 4048 | 0.55 | 0.17 | 19.8 | 0.0001 | 0.00229 |
| Ndufa4\|17992 | 454 | 0.38 | 0.18 | 19.9 | 0 | 0.00229 |
| Tmsb4x\|19241 | 137 | 0.68 | 0.21 | 19.4 | 0.0001 | 0.00249 |
| Myom2\|17930 | 1191 | 0.48 | 0.22 | 19.3 | 0.0001 | 0.00252 |
| Mtus2\|77521 | 148 | −0.41 | 0.19 | 18.9 | 0.0001 | 0.00297 |
| Nr1d1\|217166 | 84 | −0.95 | 0.26 | 18.8 | 0.0001 | 0.00314 |
| Ube\|22190 | 2230 | 0.65 | 0.16 | 18.6 | 0.0001 | 0.00324 |
| Mylk4\|238564 | 336 | 0.36 | 0.22 | 18.4 | 0.0001 | 0.00349 |
| Ivns1abp\|117198 | 1353 | 0.68 | 0.16 | 18.1 | 0.0001 | 0.00406 |
| Eno3\|13808 | 845 | 0.56 | 0.18 | 17.4 | 0.0002 | 0.00478 |
| Actg1\|11465 | 116 | 0.63 | 0.28 | 17.7 | 0.0001 | 0.00478 |
| Myh14\|71960 | 259 | −0.36 | 0.21 | 17.5 | 0.0002 | 0.00478 |
| Cox8b\|12869 | 376 | 0.16 | 0.14 | 17.3 | 0.0002 | 0.00478 |
| Pfkfb2\|18640 | 282 | 0.67 | 0.2 | 17.6 | 0.0002 | 0.00478 |
| Atp5o\|28080 | 740 | 0.39 | 0.14 | 17.3 | 0.0002 | 0.00478 |
| Rhobtb1\|69288 | 157 | 0.63 | 0.2 | 17.5 | 0.0002 | 0.00478 |
| Fam160b2\|239170 | 176 | 0.46 | 0.2 | 17.3 | 0.0002 | 0.00479 |
| Dgat2\|67800 | 362 | 0.47 | 0.15 | 17.2 | 0.0002 | 0.00479 |
| Ckmt2\|76722 | 2127 | 0.42 | 0.21 | 17.2 | 0.0002 | 0.00479 |
| Gapdh\|14433 | 3001 | 0.49 | 0.17 | 16.9 | 0.0002 | 0.00544 |
| Lrprc\|72416 | 274 | 0.14 | 0.16 | 16.8 | 0.0002 | 0.0056 |
| Frmd5\|228564 | 181 | 0.82 | 0.21 | 16.2 | 0.0003 | 0.00708 |
| Atp2a2\|11938 | 21514 | 0.3 | 0.19 | 16.2 | 0.0003 | 0.00708 |
| Flot1\|14251 | 139 | −0.76 | 0.23 | 16.1 | 0.0003 | 0.00727 |
| Casq2\|12373 | 590 | 0.31 | 0.18 | 15.9 | 0.0003 | 0.00781 |
| Acaa2\|52538 | 588 | 0.26 | 0.2 | 15.4 | 0.0004 | 0.00945 |

TABLE 4-continued

Genes of potential interest

| Gene | Base Mean | log2FoldChange | lfcSE | stat | pvalue | padj |
|---|---|---|---|---|---|---|
| Ttn\|22138 | 2150 | 0.06 | 0.17 | 15.4 | 0.0005 | 0.00945 |
| Hrc\|15464 | 1924 | 0.24 | 0.13 | 15.4 | 0.0004 | 0.00945 |
| Fkbp4\|14228 | 283 | 0.18 | 0.2 | 15.5 | 0.0004 | 0.00945 |
| Plec\|18810 | 246 | −0.71 | 0.2 | 15.3 | 0.0005 | 0.00969 |
| Cox4i1\|12857 | 1701 | 0.39 | 0.15 | 15.1 | 0.0005 | 0.01081 |
| Ndufs2\|226646 | 778 | 0.33 | 0.16 | 15 | 0.0006 | 0.011 |
| Spag7\|216873 | 203 | 0.3 | 0.18 | 14.9 | 0.0006 | 0.01128 |
| Doc2g\|60425 | 335 | −0.31 | 0.2 | 14.9 | 0.0006 | 0.01128 |
| Uqcrq\|22272 | 230 | −0.95 | 0.26 | 14.6 | 0.0007 | 0.01259 |
| Klhl21\|242785 | 285 | 0.41 | 0.23 | 14.3 | 0.0008 | 0.0141 |
| Vegfa\|22339 | 509 | 0.36 | 0.15 | 14.1 | 0.0009 | 0.01563 |
| Ehd4\|98878 | 268 | −0.1 | 0.2 | 14.1 | 0.0009 | 0.01571 |
| Rplp1\|56040 | 121 | −0.78 | 0.23 | 14 | 0.0009 | 0.01631 |
| Uqcrh\|66576 | 505 | 0.5 | 0.18 | 13.6 | 0.0011 | 0.01913 |
| Polr2a\|20020 | 191 | −0.22 | 0.21 | 13.5 | 0.0012 | 0.02023 |
| Ifngr2\|15980 | 98 | 0.4 | 0.23 | 13.2 | 0.0014 | 0.02279 |
| Adssl1\|11565 | 121 | −0.18 | 0.24 | 13.2 | 0.0014 | 0.02279 |
| Ankrd23\|78321 | 261 | −0.62 | 0.25 | 13 | 0.0015 | 0.02419 |
| Ncor2\|20602 | 120 | −0.61 | 0.22 | 13 | 0.0015 | 0.02419 |
| Cpt2\|12896 | 108 | −0.14 | 0.24 | 12.8 | 0.0017 | 0.02657 |
| Lamb2\|16779 | 341 | −0.26 | 0.15 | 12.6 | 0.0018 | 0.02714 |
| Oxct1\|67041 | 565 | 0.17 | 0.17 | 12.6 | 0.0018 | 0.02714 |
| Tnnt2\|21956 | 51047 | 0.45 | 0.13 | 12.7 | 0.0018 | 0.02714 |
| Ndufa3\|66091 | 174 | 0.23 | 0.17 | 12.5 | 0.0019 | 0.02827 |
| Mef2d\|17261 | 170 | −0.66 | 0.19 | 12.5 | 0.0019 | 0.02839 |
| Cox6c\|12864 | 579 | 0.35 | 0.15 | 12.5 | 0.002 | 0.02856 |
| Adck3\|67426 | 332 | 0.09 | 0.14 | 12.2 | 0.0022 | 0.02983 |
| Hspa5\|14828 | 256 | −0.63 | 0.18 | 12.3 | 0.0021 | 0.02983 |
| Chchd10\|103172 | 311 | −0.67 | 0.24 | 12.3 | 0.0022 | 0.02983 |
| Uba52\|22186 | 267 | 0.58 | 0.19 | 12.2 | 0.0022 | 0.02983 |
| Ndufv3\|78330 | 253 | 0.23 | 0.18 | 12.3 | 0.0021 | 0.02983 |
| Nme2\|18103 | 155 | 0.49 | 0.18 | 12.2 | 0.0023 | 0.03034 |
| Perp\|64058 | 90 | 0.19 | 0.24 | 12.1 | 0.0024 | 0.03119 |
| Tnni3\|21954 | 14712 | 0.33 | 0.17 | 11.9 | 0.0026 | 0.0334 |
| Pln\|18821 | 9408 | 0.33 | 0.15 | 11.9 | 0.0026 | 0.0334 |
| Atp1a1\|11928 | 724 | −0.43 | 0.14 | 11.9 | 0.0027 | 0.03361 |
| Fyco1\|17281 | 957 | 0.03 | 0.17 | 11.9 | 0.0027 | 0.03361 |
| Ddrgk1\|77006 | 132 | 0.23 | 0.22 | 11.8 | 0.0028 | 0.03365 |
| Mb\|17189 | 51394 | 0.36 | 0.2 | 11.8 | 0.0028 | 0.03365 |
| Hspa8\|15481 | 686 | 0.06 | 0.16 | 11.8 | 0.0028 | 0.03365 |
| Prkar1a\|19084 | 375 | −0.41 | 0.17 | 11.6 | 0.003 | 0.03653 |
| Idh3b\|170718 | 504 | 0.31 | 0.15 | 11.4 | 0.0034 | 0.04026 |
| D19Wsu162e\|226178 | 142 | 0.42 | 0.2 | 11.4 | 0.0034 | 0.04026 |
| Hk1\|15275 | 162 | −0.28 | 0.2 | 11.2 | 0.0036 | 0.04125 |
| Cryab\|12955 | 3327 | 0.14 | 0.15 | 11.2 | 0.0037 | 0.04125 |
| Nfic\|18029 | 168 | −0.52 | 0.2 | 11.2 | 0.0036 | 0.04125 |
| Atp5f1\|11950 | 580 | 0.34 | 0.17 | 11.2 | 0.0037 | 0.04125 |
| Tpt1\|22070 | 420 | 0.42 | 0.24 | 11.2 | 0.0036 | 0.04125 |
| Pdk4\|27273 | 369 | −2.22 | 0.72 | 11.2 | 0.0038 | 0.04154 |
| Etfb\|110826 | 728 | 0.33 | 0.14 | 10.8 | 0.0044 | 0.04746 |
| Mdh1\|17449 | 1465 | 0.23 | 0.15 | 10.8 | 0.0044 | 0.04746 |
| Uqcrc2\|67003 | 455 | 0.29 | 0.17 | 10.8 | 0.0045 | 0.04746 |
| Sdhb\|67680 | 590 | 0.19 | 0.17 | 10.9 | 0.0044 | 0.04746 |

Figure 3A:
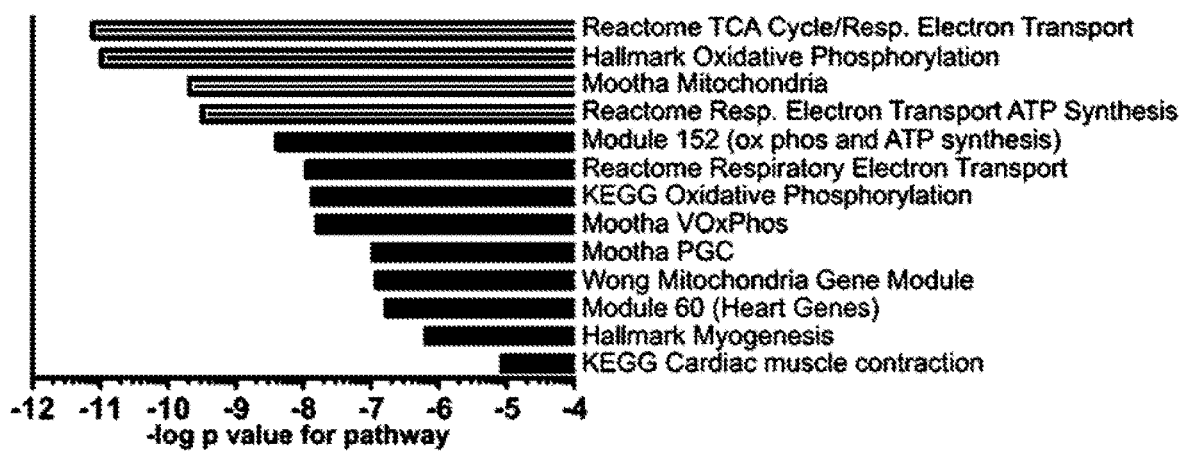
FIGS. 3A-3E. Dabuzalgron augments mitochondrial transcript expression and function in hearts from mice treated with doxorubicin. Male mice were treated with either doxorubicin 20 mg/kg or vehicle (phosphate buffered saline, PBS) by a single intraperitoneal injection followed by 7 days of treatment with either Dabuzalgron 10 µg/kg or water by gavage twice daily. Heart tissue was collected immediately after sacrifice on Day 7.

Gene set analysis was performed based on the univariate statistics calculated from DESeq2. (Table 5 and Table 6) Marked differences were identified in numerous pathways related to mitochondrial function, as seen in FIG. 3A.

TABLE 5

RNAseq pathways enriched with p value < $10^{-4}$

| Pathways | P value | Genes in set |
|---|---|---|
| REACTOME_TCA_CYCLE_AND_RESPIRATORY_ELECTRON_TRANSPORT | 7.68E-12 | 112 |
| HALLMARK_OXIDATIVE_PHOSPHORYLATION | 1.04E-11 | 194 |
| MOOTHA_HUMAN_MITODB_6_2002 | 5.17E-11 | 407 |
| MOOTHA_MITOCHONDRIA | 2.04E-10 | 421 |
| REACTOME_RESPIRATORY_ELECTRON_TRANSPORT_ATP_SYNTHESIS_BY_CHEMIOSMOTIC_COUPLING | 3.20E-10 | 76 |
| KAAB_HEART_ATRIUM_VS_VENTRICLE_DN | 4.19E-10 | 245 |
| KEGG_OLFACTORY_TRANSDUCTION | 1.25E-09 | 233 |
| MODULE_152 | 4.00E-09 | 120 |
| PID_CD8_TCR_PATHWAY | 5.69E-09 | 50 |

TABLE 5-continued

RNAseq pathways enriched with p value < $10^{-4}$

| Pathways | P value | Genes in set |
|---|---|---|
| KEGG_PARKINSONS_DISEASE | 9.16E−09 | 105 |
| BIOCARTA_PML_PATHWAY | 9.73E−09 | 16 |
| REACTOME_RESPIRATORY_ELECTRON_TRANSPORT | 1.12E−08 | 61 |
| KEGG_OXIDATIVE_PHOSPHORYLATION | 1.36E−08 | 106 |
| MOOTHA_VOXPHOS | 1.60E−08 | 83 |
| BURTON_ADIPOGENESIS_6 | 2.09E−08 | 176 |
| MODULE_62 | 3.31E−08 | 86 |
| KEGG_ALZHEIMERS_DISEASE | 4.12E−08 | 143 |
| TERAO_AOX4_TARGETS_SKIN_UP | 8.54E−08 | 32 |
| REACTOME_DNA_REPAIR | 9.42E−08 | 100 |
| MOOTHA_PGC | 1.06E−07 | 392 |
| WONG_MITOCHONDRIA_GENE_MODULE | 1.20E−07 | 212 |
| HSIAO_HOUSEKEEPING_GENES | 1.20E−07 | 357 |
| MODULE_114 | 1.42E−07 | 309 |
| MODULE_60 | 1.67E−07 | 380 |
| RIBONUCLEOPROTEIN_BINDING | 1.78E−07 | 12 |
| KAMMINGA_EZH2_TARGETS | 1.79E−07 | 39 |
| MODULE_151 | 2.56E−07 | 292 |
| STEIN_ESRRA_TARGETS_UP | 2.64E−07 | 344 |
| KEGG_HUNTINGTONS_DISEASE | 2.70E−07 | 153 |
| BIOCARTA_RELA_PATHWAY | 3.01E−07 | 16 |
| MITOCHONDRION | 4.19E−07 | 315 |
| HEMATOPOIETIN_INTERFERON_CLASSD200_DOMAIN_CYTOKINE_RECEPTOR_BINDING | 4.32E−07 | 22 |
| GNF2_ELAC2 | 6.36E−07 | 43 |
| HALLMARK_MYOGENESIS | 6.48E−07 | 190 |
| POSITIVE_REGULATION_OF_MULTICELLULAR_ORGANISMAL_PROCESS | 1.66E−06 | 54 |
| REACTOME_TRANSPORT_OF_MATURE_MRNA_DERIVED_FROM_AN_INTRONLESS_TRANSCRIPT | 1.71E−06 | 32 |
| KEGG_REGULATION_OF_AUTOPHAGY | 1.78E−06 | 34 |
| GNF2_SPINK1 | 1.90E−06 | 11 |
| CROONQUIST_IL6_DEPRIVATION_DN | 2.51E−06 | 94 |
| REACTOME_ANTIGEN_PROCESSING_UBIQUITINATION_PROTEASOME_DEGRADATION | 3.05E−06 | 189 |
| ELVIDGE_HIF1A_AND_HIF2A_TARGETS_UP | 3.07E−06 | 39 |
| chr1q41 | 3.07E−06 | 26 |
| REACTOME_HIV_INFECTION | 3.36E−06 | 177 |
| STEIN_ESRRA_TARGETS | 3.83E−06 | 474 |
| MODULE_6 | 4.11E−06 | 346 |
| MOSERLE_IFNA_RESPONSE | 4.32E−06 | 22 |
| chr15q14 | 4.37E−06 | 34 |
| MODULE_12 | 5.25E−06 | 326 |
| BARRIER_COLON_CANCER_RECURRENCE_UP | 6.39E−06 | 40 |
| HALLMARK_FATTY_ACID_METABOLISM | 6.65E−06 | 151 |
| MODULE_1 | 7.47E−06 | 336 |
| MODULE_5 | 8.08E−06 | 379 |
| KEGG_CARDIAC_MUSCLE_CONTRACTION | 8.54E−06 | 64 |
| TGACCTY_V$ERR1_Q2 | 8.97E−06 | 891 |
| SWEET_LUNG_CANCER_KRAS_DN | 9.74E−06 | 395 |
| HALLMARK_ADIPOGENESIS | 1.03E−05 | 191 |
| MODULE_93 | 1.03E−05 | 160 |
| KIM_ALL_DISORDERS_OLIGODENDROCYTE_NUMBER_CORR_UP | 1.08E−05 | 695 |
| MODULE_83 | 1.14E−05 | 295 |
| MODULE_2 | 1.26E−05 | 354 |
| GSE1432_1H_VS_6H_IFNG_MICROGLIA_DN | 1.42E−05 | 176 |
| REACTOME_ASPARAGINE_N_LINKED_GLYCOSYLATION | 1.65E−05 | 79 |
| MORF_RAN | 1.67E−05 | 256 |
| GSE14000_TRANSLATED_RNA_VS_MRNA_DC_UP | 1.88E−05 | 188 |
| KEGG_FOLATE_BIOSYNTHESIS | 1.93E−05 | 11 |
| REACTOME_SYNTHESIS_OF_BILE_ACIDS_AND_BILE_SALTS | 2.17E−05 | 18 |
| WAGNER_APO2_SENSITIVITY | 2.18E−05 | 19 |
| REACTOME_NEP_NS2_INTERACTS_WITH_THE_CELLULAR_EXPORT_MACHINERY | 2.46E−05 | 27 |
| MODULE_38 | 2.75E−05 | 407 |
| MARTINEZ_TP53_TARGETS_DN | 2.82E−05 | 509 |
| HUMMERICH_SKIN_CANCER_PROGRESSION_DN | 2.99E−05 | 97 |
| KIM_BIPOLAR_DISORDER_OLIGODENDROCYTE_DENSITY_CORR_UP | 3.05E−05 | 625 |
| BERENJENO_TRANSFORMED_BY_RHOA_DN | 3.30E−05 | 365 |
| PROTEIN_METHYLTRANSFERASE_ACTIVITY | 3.55E−05 | 13 |
| GSE10236_KLRG1INT_VS_KLRG1HIGH_EFF_CD8_TCELL_DN | 3.69E−05 | 170 |
| GSE7460_CD8_TCELL_VS_TREG_ACT_DN | 3.73E−05 | 184 |
| SULFOTRANSFERASE_ACTIVITY | 3.73E−05 | 22 |
| FLECHNER_BIOPSY_KIDNEY_TRANSPLANT_REJECTED_VS_OK_DN | 3.81E−05 | 497 |
| YOSHIMURA_MAPK8_TARGETS_UP | 3.93E−05 | 1081 |
| REACTOME_GPCR_DOWNSTREAM_SIGNALING | 3.94E−05 | 549 |
| S_ADENOSYLMETHIONINE_DEPENDENT_METHYLTRANSFERASE_ACTIVITY | 4.05E−05 | 22 |
| REGULATION_OF_IMMUNE_SYSTEM_PROCESS | 4.35E−05 | 50 |
| chr13q13 | 4.37E−05 | 20 |
| YU_MYC_TARGETS_UP | 4.39E−05 | 38 |

TABLE 5-continued

RNAseq pathways enriched with p value < $10^{-4}$

| Pathways | P value | Genes in set |
|---|---|---|
| chr11p12 | 4.50E−05 | 11 |
| BIOCARTA_CYTOKINE_PATHWAY | 4.56E−05 | 11 |
| STRUCTURAL_MOLECULE_ACTIVITY | 4.69E−05 | 193 |
| REACTOME_NEGATIVE_REGULATION_OF_FGFR_SIGNALING | 4.81E−05 | 29 |
| CYTOPLASMIC_PART | 4.84E−05 | 1256 |
| MORF_SOD1 | 5.17E−05 | 265 |
| CHEOK_RESPONSE_TO_MERCAPTOPURINE_UP | 5.41E−05 | 12 |
| SUMI_HNF4A_TARGETS | 5.56E−05 | 27 |
| MARTINEZ_RB1_TARGETS_UP | 5.75E−05 | 597 |
| FEEDING_BEHAVIOR | 5.98E−05 | 12 |
| WEST_ADRENOCORTICAL_TUMOR_MARKERS_UP | 6.06E−05 | 19 |
| MODULE_77 | 6.39E−05 | 27 |
| DNA_REPLICATION | 6.53E−05 | 91 |
| SHIN_B_CELL_LYMPHOMA_CLUSTER_9 | 6.56E−05 | 16 |
| GSE24634_TEFF_VS_TCONV_DAY7_IN_CULTURE_UP | 6.74E−05 | 175 |
| CHEN_ETV5_TARGETS_TESTIS | 6.76E−05 | 15 |
| MODULE_22 | 6.94E−05 | 44 |
| MCBRYAN_PUBERTAL_BREAST_4_5WK_DN | 6.98E−05 | 180 |
| GNF2_MYL3 | 7.22E−05 | 29 |
| AGTCTTA, MIR-499 | 7.83E−05 | 64 |
| PID_P38_ALPHA_BETA_PATHWAY | 8.11E−05 | 31 |
| WONG_ADULT_TISSUE_STEM_MODULE | 8.14E−05 | 660 |
| PID_TXA2PATHWAY | 8.20E−05 | 54 |
| KANG_DOXORUBICIN_RESISTANCE_UP | 8.63E−05 | 50 |
| MODULE_43 | 8.94E−05 | 91 |
| MODULE_88 | 9.07E−05 | 672 |
| MORF_ACTG1 | 9.12E−05 | 127 |
| GSE17974_0H_VS_4H_IN_VITRO_ACT_CD4_TCELL_DN | 9.29E−05 | 167 |
| GNF2_MYL2 | 9.71E−05 | 30 |
| REACTOME_ZINC_TRANSPORTERS | 9.90E−05 | 13 |
| REACTOME_NUCLEOTIDE_EXCISION_REPAIR | 9.98E−05 | 46 |

TABLE 6

RNAseq pre-specified pathway analysis

| Pathways | P value | Genes in set |
|---|---|---|
| REACTOME_TCA_CYCLE_AND_RESPIRATORY_ELECTRON_TRANSPORT | 7.68E−12 | 112 |
| HALLMARK_OXIDATIVE_PHOSPHORYLATION | 1.04E−11 | 194 |
| REACTOME_RESPIRATORY_ELECTRON_TRANSPORT_ATP_SYNTHESIS_BY_CHEMIOSMOTIC_COUPLING | 3.20E−10 | 76 |
| KAAB_HEART_ATRIUM_VS_VENTRICLE_DN | 4.19E−10 | 245 |
| REACTOME_RESPIRATORY_ELECTRON_TRANSPORT | 1.12E−08 | 61 |
| MOOTHA_PGC | 1.06E−07 | 392 |
| MITOCHONDRION | 4.19E−07 | 315 |
| HALLMARK_FATTY_ACID_METABOLISM | 6.65E−06 | 151 |
| KEGG_CARDIAC_MUSCLE_CONTRACTION | 8.54E−06 | 64 |
| YANG_BCL3_TARGETS_UP | 0.000321895 | 323 |
| STRUCTURAL_CONSTITUENT_OF_MUSCLE | 0.000690522 | 29 |
| REACTOME_FORMATION_OF_ATP_BY_CHEMIOSMOTIC_COUPLING | 0.000834816 | 13 |
| HALLMARK_HYPOXIA | 0.00178533 | 183 |
| REGULATION_OF_HEART_CONTRACTION | 0.003647298 | 23 |
| HALLMARK_P53_PATHWAY | 0.013850996 | 188 |
| KYNG_RESPONSE_TO_H2O2 | 0.017897901 | 65 |
| MOOTHA_GLYCOLYSIS | 0.026451641 | 18 |
| HALLMARK_GLYCOLYSIS | 0.033988771 | 191 |
| KEGG_PPAR_SIGNALING_PATHWAY | 0.035107916 | 63 |
| KEGG_GLYCOLYSIS_GLUCONEOGENESIS | 0.037928758 | 54 |
| REACTOME_GLYCOLYSIS | 0.056439728 | 23 |
| KEGG_REGULATION_OF_ACTIN_CYTOSKELETON | 0.065196891 | 194 |
| CHEN_LVAD_SUPPORT_OF_FAILING_HEART_DN | 0.07199588 | 38 |
| FATTY_ACID_METABOLIC_PROCESS | 0.11200352 | 57 |
| NADH_DEHYDROGENASE_COMPLEX | 0.116276143 | 14 |
| ELECTRON_TRANSPORT_GO_0006118 | 0.142743659 | 48 |
| BIOCARTA_P53_PATHWAY | 0.257777775 | 16 |

Figure 3B:
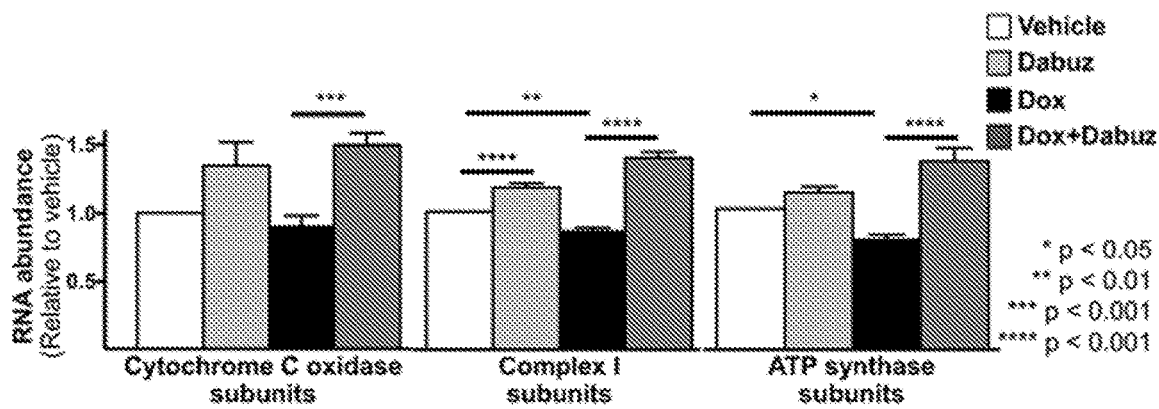
Figure 3C:
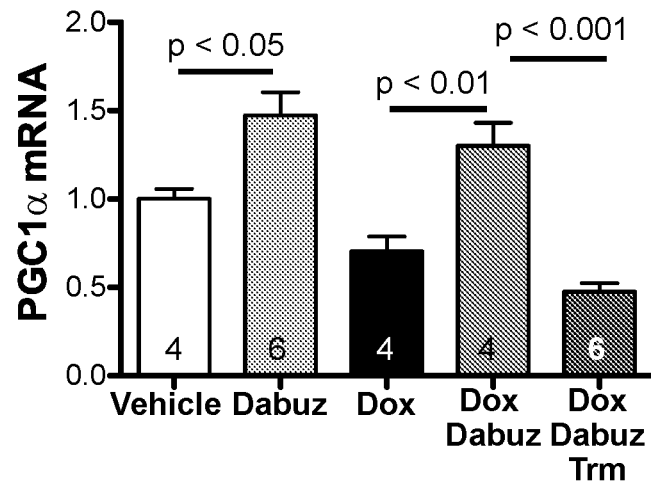
Figure 3D:
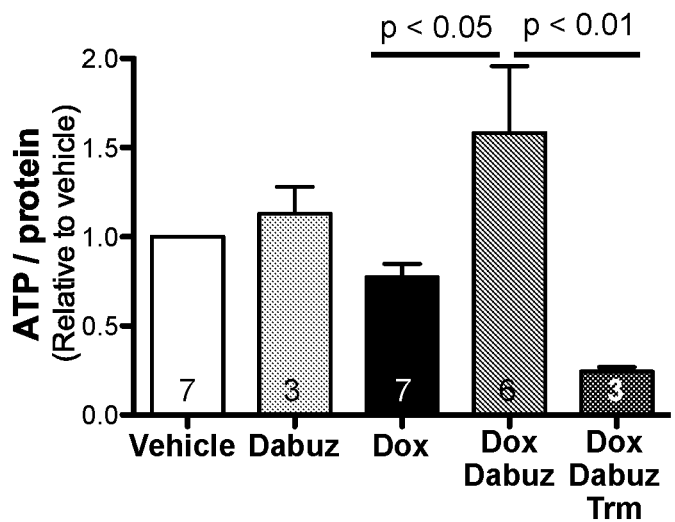
Figure 3E:
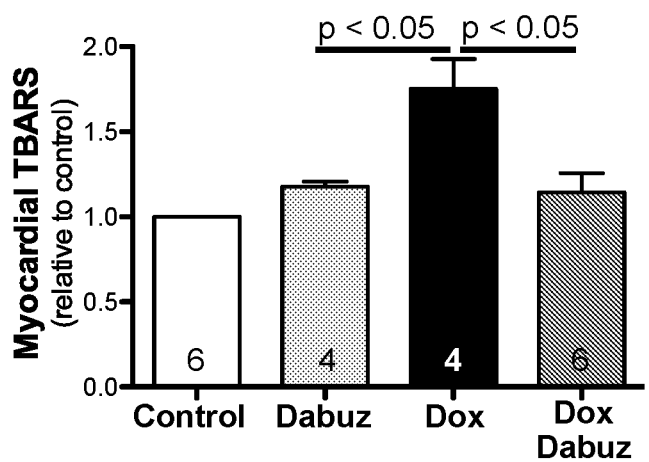

Further analysis of transcripts within these mitochondrial pathways revealed that DOX decreased the abundance of Complex I (42 genes) and ATP synthase subunits (17 genes). (FIG. 3B) Treatment with dabuzalgron restored expression of these gene sets and also increased expression of Cytochrome C oxidase subunits (25 genes) after DOX. Treatment with dabuzalgron in the absence of DOX increased Complex I subunit abundance, but had no significant effect on Cytochrome C or ATP synthase. (FIG. 3B). Many of the genes encoding electron transport and other key mitochondrial proteins are under transcriptional regulation by peroxisome proliferator-activated receptor gamma coactivator 1-alpha.(22) We found that DOX decreased PGC1α abundance in vivo, (FIG. 3C) consistent with prior reports. (23) Treatment with dabuzalgron increased PGC1α abundance in the hearts of mice treated with either DOX or vehicle control. (FIG. 3C). To assess the functional effect of these transcriptional differences, we assayed ATP content in freshly harvested heart homogenates. DOX decreased ATP content by 23±7% compared to untreated hearts, consistent with previous reports.(17) (FIG. 3D) Treatment with dabuzalgron restored ATP content in the hearts of DOX-treated mice, but did not affect ATP in uninjured mice. Using the highly selective MEK inhibitor, trametinib, we found that inhibiting activation of ERK1/2 abrogated dabuzalgron's beneficial effect on ATP synthesis after DOX. Oxidative stress is central to the pathobiology of DOX cardiotoxicity and arises in part from compromised mitochondrial function.(24) To assess further the functional implications of these transcriptional findings, we measured thiobarbituric acid reactive substances (TBARS), in mouse heart tissue. TBARS, a measure of lipid peroxidation, were more abundant in the hearts of mice treated with DOX. Co-administration of dabuzalgron normalized TBARS content. (FIG. 3E), In summary, dabuzalgron protected against the reduction in transcripts related to mitochondrial function, preserved ATP content, and reduced oxidative stress in the hearts of mice treated with DOX. These beneficial effects may be mediated by activation of ERK1/2 and upregulation of PGC1a.

To assess the functional effect of these transcriptional differences, we assayed ATP content in freshly harvested heart homogenates. DOX decreased ATP content by 23±7% compared to untreated hearts. (FIG. 3C) Treatment with dabuzalgron restored ATP content in the hearts of DOX-treated mice, but did not affect ATP in untreated mice.

In summary, dabuzalgron protected against the reduction in transcripts related to mitochondrial function and preserved ATP content in the hearts of mice treated with DOX.

Figure 4A:
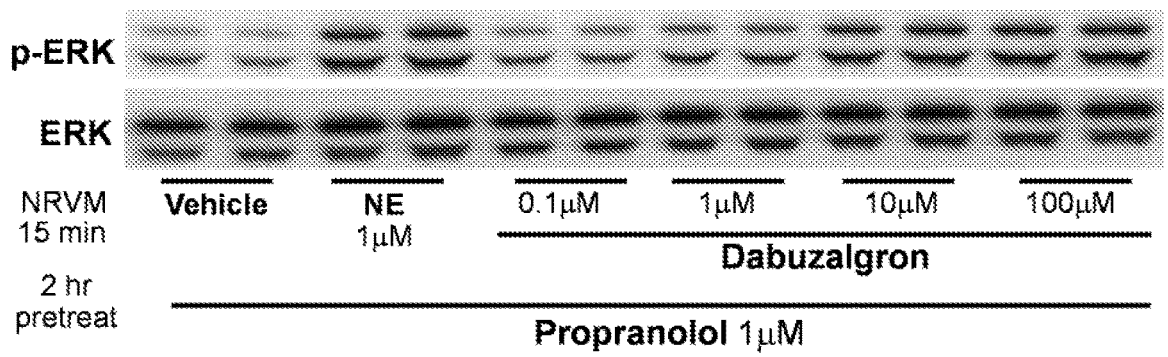
FIGS. 4A-4F. In neonatal rat ventricular myocytes, dabuzalgron activates ERK, a canonical downstream signaling partner of the α1A-AR. Neonatal rat ventricular myocytes (NRVMs) were pre-treated with the β-AR antagonist propranolol then exposed for 15 minutes to various concentrations of dabuzalgron, using the non-selective α1-AR agonist norepinephrine (NE) as a positive control. The reaction was stopped immediately and lysates were blotted for total and phospho-ERK (pERK).
Figure 4B:
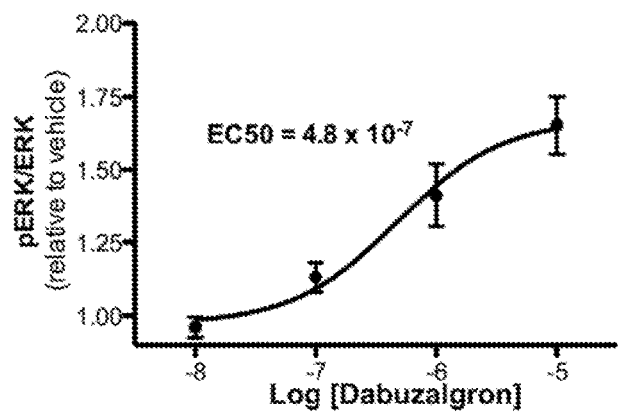
Figure 4C:
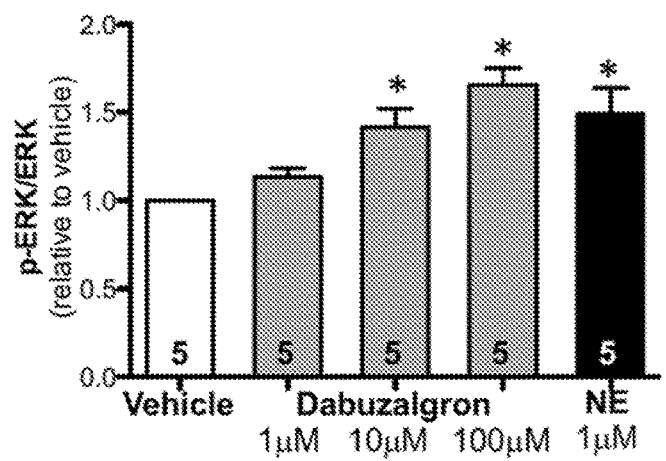
Figure 4D:
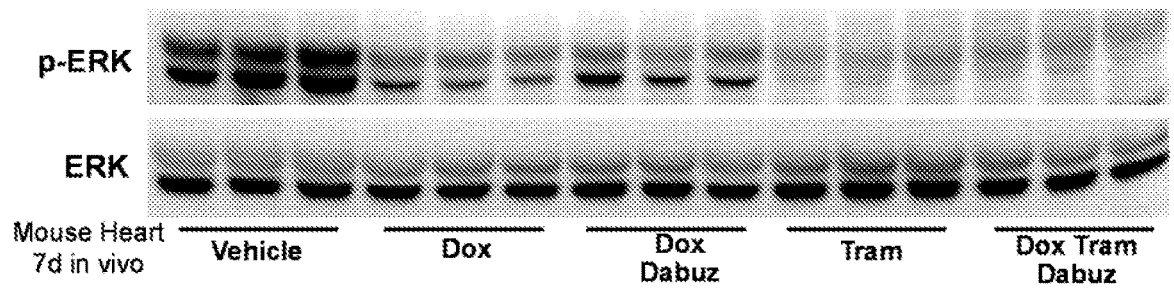
Figure 4E:
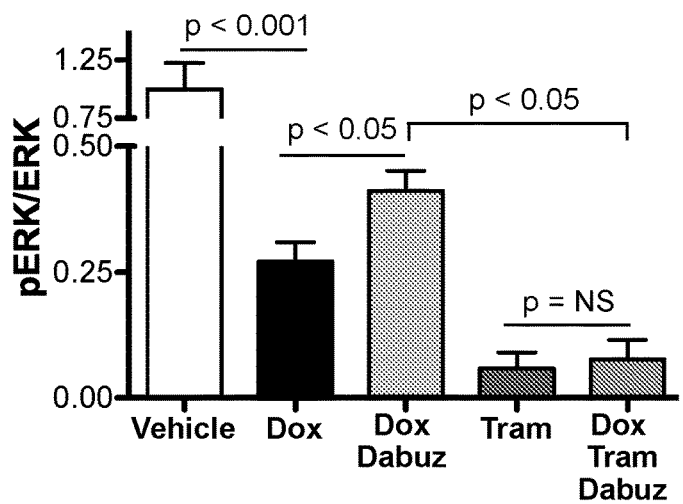
Figure 4F:
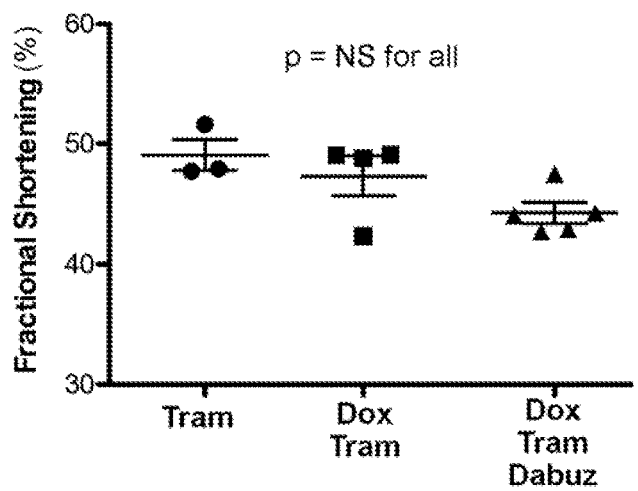

Dabuzalgron protects neonatal rat ventricular myocytes from cell death due to doxorubicin. ERK1/2 activation contributes to the cardioprotective effects of dabuzalgron. Neonatal rat ventricular myocytes (NRVMs) express the α1A and α1B subtypes, have been used extensively to assess the effects of non-selective α1-AR activation, and faithfully predict in vivo α1-AR biology.(25,26) To test the effect of an α1A agonist on uninjured NRVMs, we administered various concentrations of dabuzalgron. After 15 minutes of treatment, we blotted NRVM lysates for activation of ERK, (FIG. 4A) a canonical downstream signaling partner of the α1A that mediates the cytoprotective effects of α1A activation in vitro.(13) Dabuzalgron increased ERK phosphorylation in a dose-dependent fashion with an EC50 of 4.8× 10−7 M. (FIG. 4B) The pERK/ERK ratio was increased roughly 1.5 fold after treatment with dabuzalgron 10 μM, an effect equivalent to norepinephrine (NE) 1 μM (in the presence of the non-selective α-AR blocker, propranolol 1 μM). (FIG. 4C). We then tested the role of ERK activation in dabuzalgron's cardioprotective effects in vivo, using trametinib. Trametinib (1 mg/kg by gavage once daily) almost completely eliminated ERK activation. (FIG. 4D and FIG. 4E) DOX also reduced ERK activation, consistent with previous reports.(27) Treatment with dabuzalgron partially mitigated that effect but could not restore ERK activation after trametinib. (FIG. 4D and FIG. 4E) Co-administration of trametinib with DOX and dabuzalgron abrogated dabuzalgron's protective effect on contractile function, (FIG. 4F) suggesting that α1A-mediated positive inotropy requires ERK activation.

Figure 5A:
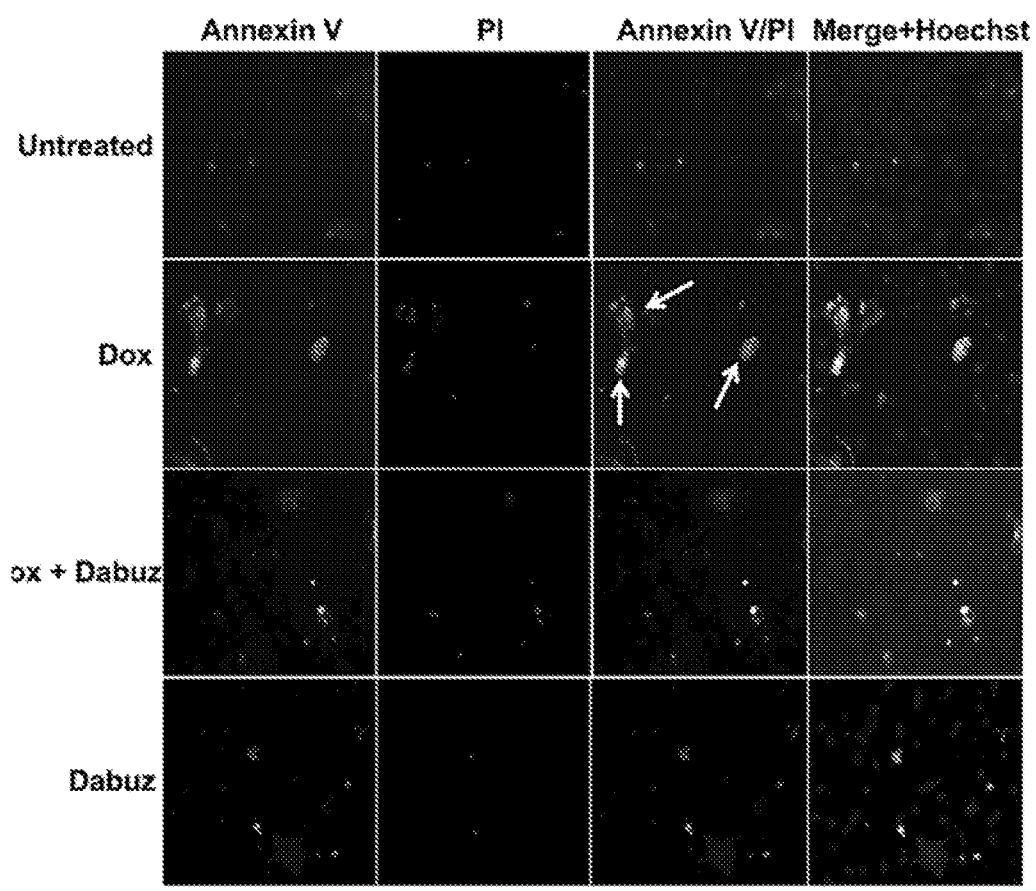
FIGS. 5A-5B. In neonatal rat ventricular myocytes, dabuzalgron protects against apoptotic and necrotic cell death due to doxorubicin. Neonatal rat ventricular myocytes (NRVMs) were treated for 4 hours with doxorubicin 204 in the presence and absence of dabuzalgron 10 μM. Apoptosis was detected using FITC-labeled Annexin V, cell death was detected using propridium iodide, and nuclei were labeled with Hoechst.

To test the cytoprotective effects of an α1A agonist, we treated NRVMs with DOX 204 in the presence and absence of dabuzalgron 1004 then assayed apoptosis and cell death using Annexin V-Fluos and propidium iodide (FIG. 5A). Four hour treatment with DOX increased apoptosis (Annexin V staining), and necrotic cell death (costaining with Annexin V and propidium iodide). (FIG. 5B) Concomitant treatment with dabuzalgron abrogated these effects. Treatment with dabuzalgron in the absence of DOX did not change Annexin V or propidium iodide staining when compared to untreated cells.

Example 5

Dabuzalgron Regulates Activators of Apoptosis and Mitochondrial Membrane Potential in Neonatal Rat Ventricular Myocytes In light of our findings that treatment with dabuzalgron preserved mitochondrial function in vivo and protected against cell death in vitro after DOX exposure, we sought to explore the effect of dabuzalgron on aspects of mitochondrial function in NRVMs. Maintenance of mitochondrial membrane potential is essential to ATP generation, and loss of membrane potential can contribute to apoptosis by increasing cytochrome c release[24], leading to activation of pro-apoptotic effectors. DOX interferes with the cellular capacity to maintain mitochondrial membrane potential and mitochondrial dysfunction contributes significantly to doxorubicin cardiotoxicity.[25]

Figure 6A:
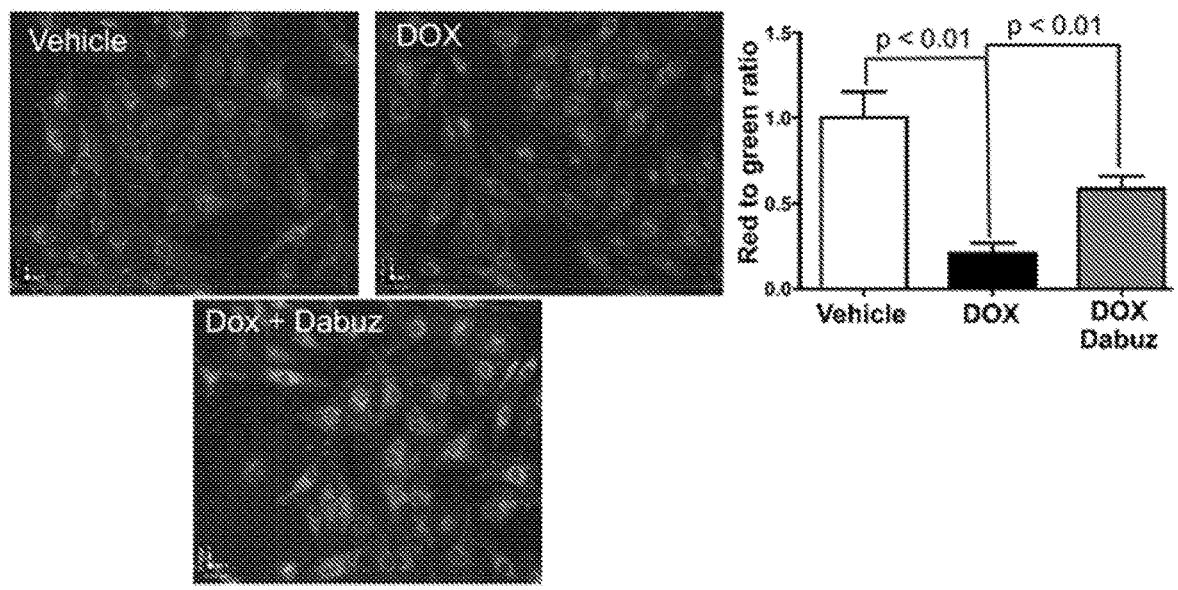
FIG. 6A-6C. In neonatal rat ventricular myocytes, dabuzalgron regulates activators of apoptosis and protects mitochondrial membrane potential after treatment with doxorubicin. Neonatal rat ventricular myocytes (NRVMs) were treated for 4 hours with doxorubicin 2 μM in the presence and absence of Dabuzalgron 10 μM.
Figure 6B:
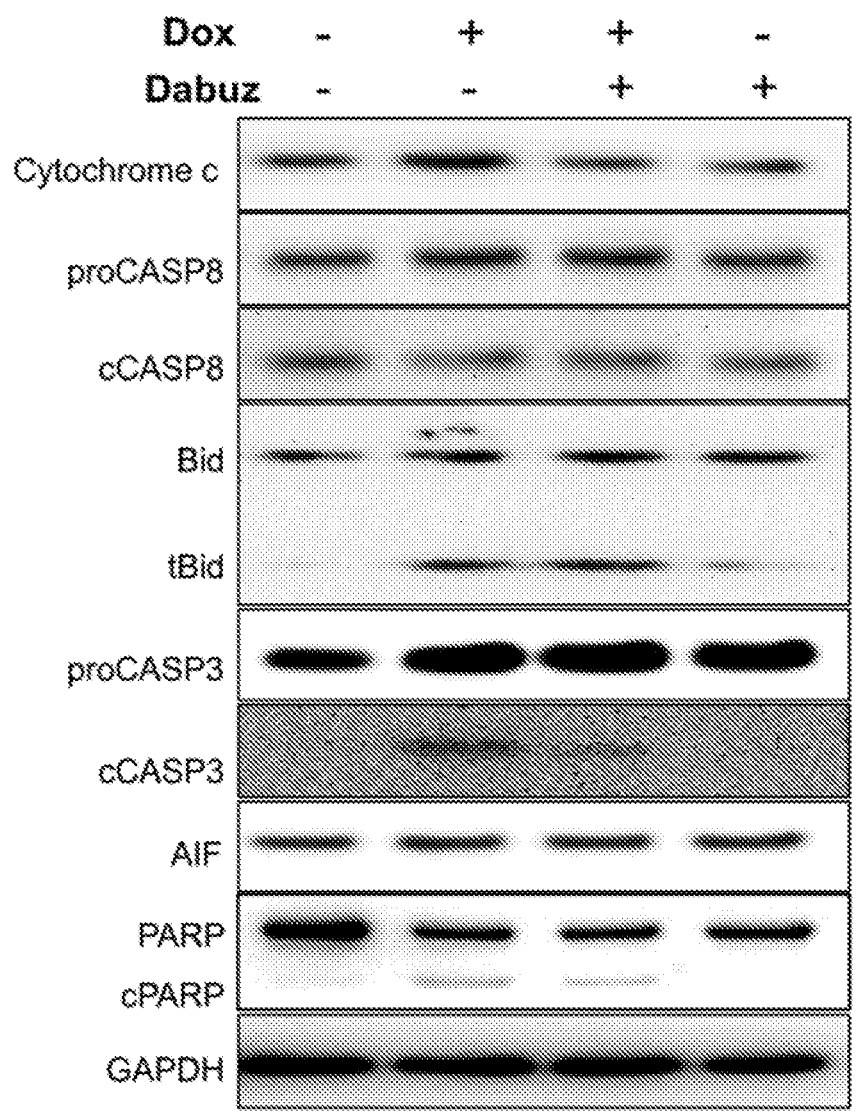
Figure 6C:
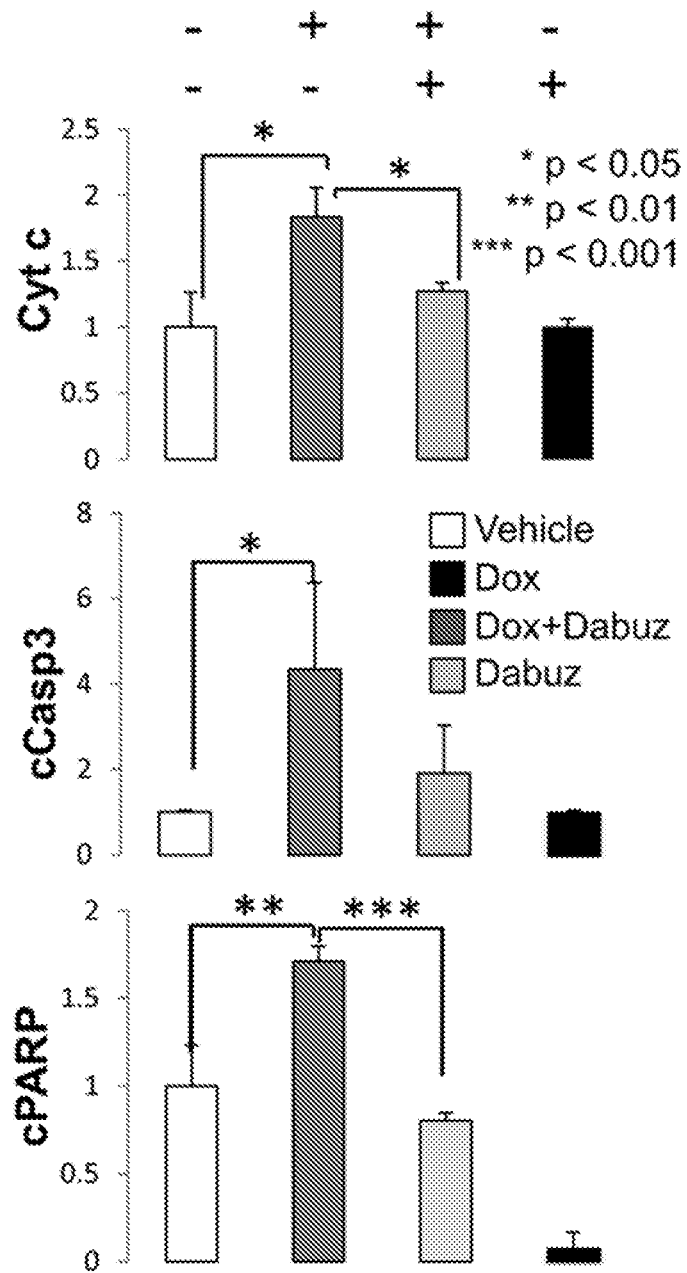
Figure 7:
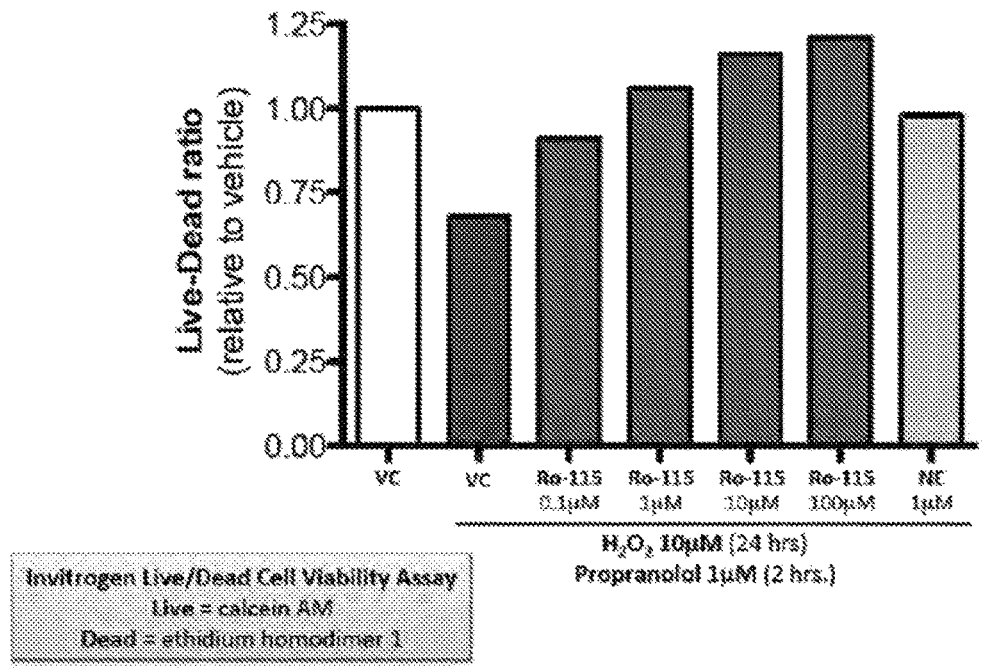
FIG. 7. Ro-115 (i.e. dabuzalgron) protects neonatal rat ventricular myocytes from toxic stimuli. Consistent with activation of cardioprotective ERK, dabuzalgron prevents myocyte death caused by toxic injuries. Shown in FIG. 7 is dabuzalgron (Ro-115) prevents myocyte death caused by oxidative stress with $H_2O_2$.
Figure 8:
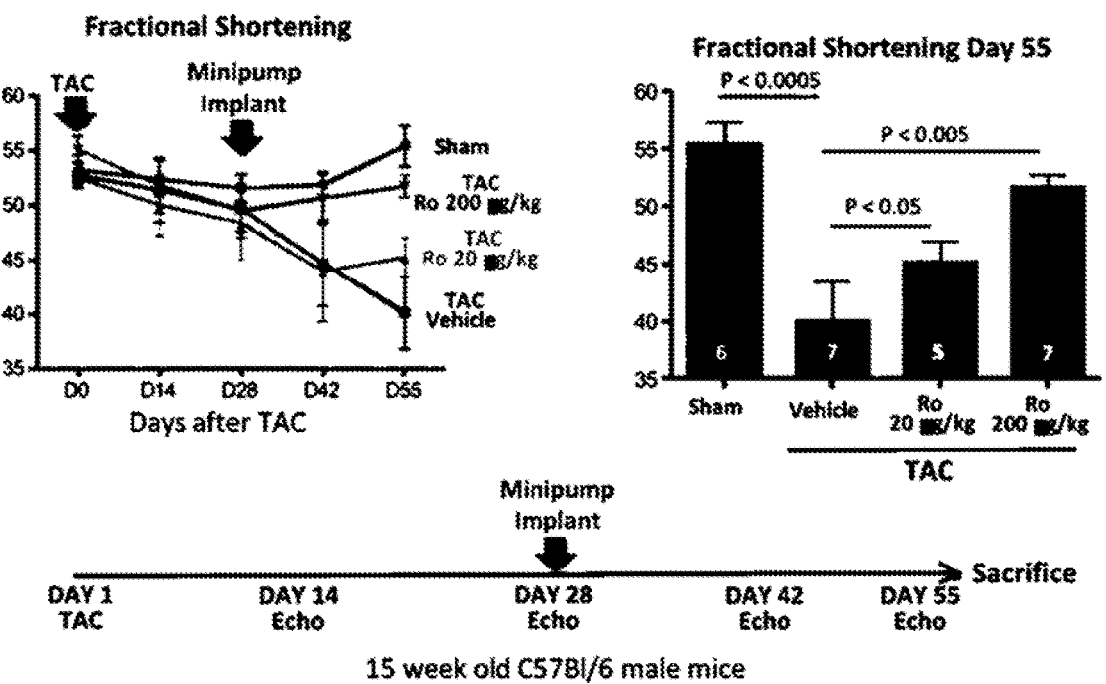
FIG. 8. Ro-115 (i.e., dabuzalgron) protects the mouse heart in vivo from pressure overload cardiomyopathy caused by transverse aortic constriction (AOC). Mice had TAC surgery on day 0, and 4 weeks later had osmotic minipumps implanted under the skin, to continuously deliver Ro-115 (i.e., dabuzalgron) or vehicle. Two doses of Ro-115 (i.e., dabuzalgron) were given, 20 ug/kg/d or 200 ug/kg/d. Cardiac function was measured before TAC, and every 2 weeks, using echocardiography. At the study end on day 55, both doses of Ro-115 (i.e., dabuzalgron) caused significant improvement in cardiac function (fractional shortening) compared with vehicle, indicating treatment of rescue of cardiomyopathy.

To test the effect of α1A activation on mitochondrial membrane potential, we treated NRVMs with DOX 204 for 4 hours in the presence of absence of dabuzalgron 10 μM then stained with the membrane permeant dye, JC-1. JC-1 exists as a green fluorescent monomer at low mitochondrial membrane potential and a red fluorescent aggregate at high mitochondrial membrane potential. DOX led to a profound loss of mitochondrial membrane potential that was partially rescued by coadministration of dabuzalgron. (FIGS. 6A-6C).

To examine the role of α1A-mediated mitochondrial protection on DOX-induced apoptosis, we immunoblotted lysates from NRVMs for cytochrome c and downstream effectors of apoptosis. DOX increased cytochrome c release and caused cleavage of caspases and PARP, suggesting that mitochondrial damage induced activation of the intrinsic apoptosis pathway, consistent with previous characterizations of doxorubicin cytotoxicity.[26] Co-administration of dabuzalgron abrogated these changes (FIGS. 6A-6C).

Figure 5B:
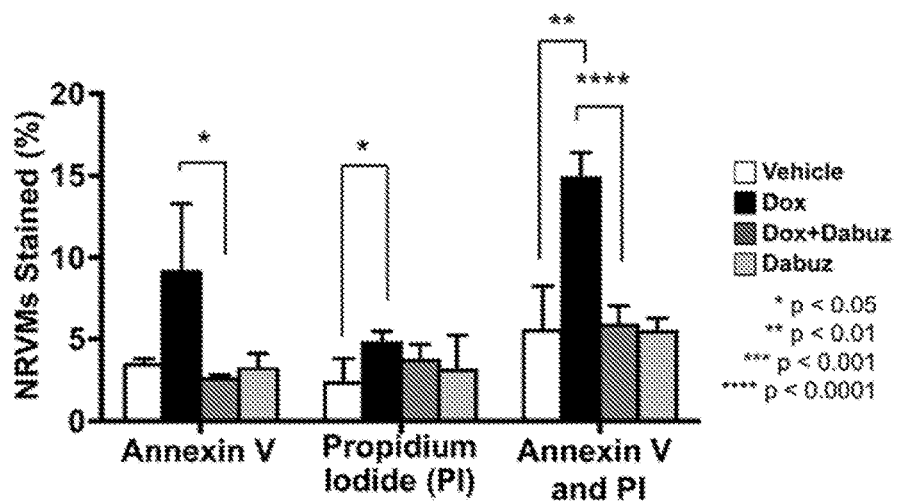

In summary, activation of the α1A-AR with dabuzalgron mitigated the detrimental effects of DOX on mitochondrial membrane potential and abrogated the activation of important elements of the apoptotic response to mitochondrial damage. These findings suggest that preservation of mitochondrial function may underlie the cytoprotective effects of α1A activation (FIGS. 5A-5B).

An important finding of this study is the demonstration that the oral selective α1A-AR agonist, dabuzalgron, is protective against anthracycline-induced cardiotoxicity. We chose to study dabuzalgron because of its α1A subtype selectivity and the fact that it was well tolerated in two large randomized clinical trials. We found that its cardioprotective effect is mediated in part through preservation of mitochondrial function, a mechanism that has not been attributed previously to α1A activation.

α1-ARs play central roles in cardiovascular biology. They are best known for their roles in the vasculature, where α1-AR activation promotes vasoconstriction. Though cardiac α1-ARs are a minor AR subpopulation relative to β1-ARs, they contribute to numerous important processes in the heart.[27] At high doses, non-selective α1-AR agonists such as phenylephrine and norepinephrine increase BP experimentally and clinically. Importantly, subpressor doses of non-selective α1-AR agonist can cause cardiac hypertrophy, indicating a direct and load-independent effect.[28] In this study, we found no effect on BP or HR in mice treated with a range of dabuzalgron doses. We chose to use 10 µg/kg for subsequent experiments because this dose had no effect on BP in either pigs or rabbits[9] when dabuzalgron was under development. These findings mirror the published human experience with dabuzalgron as a potential treatment for urinary incontinence, wherein administration of 1.5 mg by mouth twice daily did not alter BP or HR.[10]

We also found that activation of the α1A did not cause myocardial hypertrophy, consistent with various genetically altered α1A mouse models. We show here that mice lacking the α1A on a congenic C57Bl6 background have normal heart size, consistent with the α1AKO mouse on a mixed background.[29] Heart size also is normal in mice with global and cardiac-specific α1A overexpression.[4-6] Mice lacking both myocardial al subtypes (α1ABKO) have small hearts, as do mice lacking the α1B on a congenic background.[30] Collectively, these findings suggest that cardiomyocyte hypertrophy induced by non-selective α1-AR agonists is mediated by the α1B subtype.

α1-ARs are best known as vascular receptors, where α1-AR activation promotes vasoconstriction. At high doses, non-selective α1-AR agonists such as phenylephrine increase BP experimentally and clinically. In this study, we found no effect on BP or HR in mice treated with a range of dabuzalgron doses. We chose to use 10 µg/kg for subsequent experiments because Roche studied this dose in pigs and rabbits.(10) Our findings mirror the published human experience with dabuzalgron as a treatment for urinary incontinence, wherein administration of 1.5 mg by mouth twice daily did not alter BP or HR. ((11) and roche-trials.com)

Though cardiac α1-ARs are a minor AR subpopulation relative to α1-ARs, they contribute to numerous important processes in the heart.(26) Subpressor doses of non-selective α1-AR agonist also can cause cardiac hypertrophy, indicating a direct and load-independent effect on the heart.(30) We found that activation of the α1A did not cause myocardial hypertrophy, consistent with the fact that heart size is normal in mice with global and cardiac-specific α1A overexpression.(4-6) α1AKO mice on a congenic C57Bl6 background also have normal heart size and blood pressure. Mice lacking both myocardial al subtypes (α1ABKO) have small hearts. (31) Collectively, these findings suggest the α1B subtype mediates cardiomyocyte hypertrophy induced by non-selective α1-AR agonists.

We found that oral administration of a subpressor dose of dabuzalgron protected WT mice against DOX cardiotoxicity. This beneficial effect was absent in AKO mice, indicating that dabuzalgron's adaptive effects result from on-target activation of the α1A. High mortality and very poor contractile function in DOX-treated AKO mice further reinforce the cardioprotective function of the α1A-AR. Though other labs have used transgenic overexpression of the α1A to identify cardioprotective effects, ours is the first study to demonstrate greater susceptibility to cardiac injury in AKO mice. As such, we present evidence supporting adaptive functions for cardiac α1A-ARs using both novel pharmacological gain-of-function and novel genetic loss-of-function approaches.

The function of α1-ARs in cardiomyocyte mitochondria has not been explored to any significant extent previously. In our study, dabuzalgron protected against DOX-induced apoptosis and necrosis in NRVMs and decreased levels of intrinsic apoptotic effectors, suggesting that this benefit may be associated with preservation of mitochondrial integrity and function. Analysis of our RNAseq results showed rescue of pathways associated with mitochondrial function and metabolism after therapeutic α1A activation, a previously unrecognized mechanism for α1A activity. Treatment with DOX diminished transcript abundance within these pathways, whereas co-administration of dabuzalgron restored expression of Complex I, Cytochrome c oxidase, and ATP synthase genes. Treatment with dabuzalgron abrogated the DOX-induced reduction in myocardial ATP levels, indicating functional significance of the transcriptional changes. Though we cannot exclude a contribution from other cell types to these findings, they seem most likely to represent changes in cardiomyocytes as the α1A is not expressed on non-myocytes in the heart.(32)

We show that dabuzalgron activates ERK, a canonical downstream signaling partner of the α1A in NRVMs, and partially restores ERK activation in the hearts of mice treated with DOX. Using the highly selective MEK inhibitor, trametinib, we demonstrate that ERK phosphorylation is important for dabuzalgron's protective effects on inotropy and ATP synthesis. ERK activation was found to be critical to α1A-mediated cytoprotection in previous work using adenoviral constructs in vitro,(13) but our experiments are the first to show ERK activation in vivo by an α1A agonist. Interestingly, dabuzalgron-mediated cardioprotection does not require full restoration of ERK activation to levels seen in uninjured heart. Given the broad cellular effects of DOX, it is possible that DOX impairs ERK activation through multiple pathways, not all of which are modified by α1A activation. α1-ARs can activate ERK through multiple pathways, both PKC-dependent (33) and PKC-independent,(34) suggesting signaling resilience. Furthermore, α1A activation might mitigate the adverse effects of DOX on abundance of activated ERK by targeting activated ERK to caveolae, where its function is enhanced, as shown previously in vitro.(35,36)

We administered 20 mg/kg of DOX intraperitoneally, a dose that allometrically scales to roughly 60 mg/m2 in humans (fda.gov/downloads/Drugs/Guidances/UCM078932.pdf). Though this scaled dose is at the upper limit of the typical range for treatment of breast cancer and lymphoma, the observed mortality in our studies is out of proportion to the insult to cardiac function, suggesting that mice may suffer non-cardiac toxicities at this dose that are not fully representative of the human response. The pathogenesis and signaling associated with acute DOX cardiotoxicity likely are distinct from chronic DOX cardiomyopathy and the contribution of oxidative stress in this model may be disproportionately represented.

Chronic cardiomyopathy is the most significant source of DOX-associated cardiac morbidity, however, numerous studies indicate that acute DOX cardiotoxicity is more common than previously thought (11%(37)-21%(38)) and predicts poor outcomes. In one recent study, 32% of subjects had elevated TnI acutely after DOX. Ejection fraction (EF) dropped measurably in most subjects by 3 months and early +TnI predicted durable reduction in EF.(39) In a follow-up study, the authors found that early institution of evidence-based HF therapy protected against chronic anthracycline cardiomyopathy.(40) Collectively, these findings suggest that acute DOX cardiotoxicity may be a clinically meaningful and actionable entity.

Dabuzalgron protected against DOX-induced apoptosis and necrosis in NRVMs and decreased levels of cytochrome c and intrinsic apoptotic effectors, suggesting that this benefit may be associated with preservation of mitochondrial integrity and function. Interestingly, previous studies have linked non-selective α1-AR activation to generation of reactive oxygen species,[31,32] though α1-ARs clearly are protective against cardiac insults that induce oxidative stress such as ischemia-reperfusion, myocardial infarction, and doxorubicin. [27] As such, it is possible that the effects of myocardial α1s are dependent on subtype, context, and dose.

Mitochondrial dysfunction and impaired cardiomyocyte energetics are central to the pathobiology of HF regardless of etiology. [34] Unlike β-ARs, which are downregulated and dysfunctional, the abundance of α1A is maintained or increased in failing human heart tissue.[36, 37] The prospect of using a non-selective α1-AR agonist to treat HF is intuitively unappealing, given the effects on vascular tone at commonly used doses. Long-term systemic 2-fold overexpression of the α1A is associated with prolonged lifespan, decreased cancer incidence,[40] and improved cognition. [41]

Example 6

Methods and Experimental Setup

Verification of Dabuzalgron Chemical Structure.

Dabuzalgron was synthesized per published chemical structure.1 The purity (>95%) and identity of the compound were confirmed by nuclear magnetic resonance (NMR) spectrum and mass spectrum (MS). 1H NMR spectrum was acquired on a Varian Mercury spectrometer with 400 MHz for proton. MS data was acquired in positive ion mode using an Agilent 6110 single quadrupole mass spectrometer with an electrospray ionization (ESI) source.

Animals.

C57Bl6J mice were from Jackson Laboratory or from our breeding colony. α1A-AR knockout (AKO) mice from Paul C. Simpson were congenic on a C57Bl6J background for at least 10 generations and produced by heterozygous breeding in our animal facility. 8-12 week old males were used in all experiments. Female Sprague-Dawley rats with newborn litters were from Charles River. Animal care and experimental protocols were approved by the UNC IACUC and complied with Guide for the Care and the use of Laboratory Animals (National Research Council Committee for the Update of the Guide for the Care and Use of Laboratory Animals, 2011).

Tail Cuff Blood Pressure Measurement:

Tail cuff blood pressure (BP) and heart rate (HR) were obtained on awake mice by repeated measurements using a CODA Volume Pressure Recording tail cuff system (Kent Scientific).2 Mice were trained to the apparatus for 5 days prior to data collection. Systolic BP and HR measurements represent the average of at least 20 tail cuff inflations per mouse each afternoon.

Doxorubicin injection; dabuzalgron and trametinib gavage: Mice were trained with 3 days handling then on Day 0 mice underwent echocardiography. On Day 1, mice underwent intraperitoneal (i.p.) injection with DOX 20 mg/kg or saline vehicle using a 0.5 cc insulin syringe. On Days 1 through 7, mice received dabuzalgron 10 µg/kg or saline by gavage (Kent #FNC20-1.5) in volume of 1% of weight twice daily. Some mice received trametinib (Selleck) 1 mg/kg by gavage once daily either alone or in combination with doxorubicin or dabuzalgron. On Day 7, mice underwent echocardiography and were sacrificed by cervical dislocation after an overdose of isoflurane.

Quantitative Reverse Transcriptase PCR (qRT-PCR):

Total RNA was isolated from cells and tissue (QiagenRNeasy Plus mini kit #74134) and analyzed using a NanoDrop (ThermoScientific). For qRT-PCR, one µg of RNA was reverse transcribed using High Capacity cDNA Reverse Transcription Kit (Life Technologies #4368814). Two step qRT-PCR reactions contained 2% of the cDNA product. All reactions were performed in triplicate in a Roche 480 Light Cycler. Relative quantitation of PCR products used the ΔΔCt method relative to two validated reference genes (Tbp and Polr2a). Similar efficiencies were confirmed for all primers. All probes and primers were from Roche.

```
qRT-PCR primers:
Reference genes:
Tbp mouse
F: ggcggtttggctaggttt;         (SEQ ID NO: 1)

R: gggttatcttcacacaccatga;     (SEQ ID NO: 2)
UPL Probe # 107;

rat
F: ggggagctgtgatgtgaagt;       (SEQ ID NO: 3)

R: ccaggaaataattctggctcata;    (SEQ ID NO: 4)
UPL Probe # 97;

Polr2a mouse
F: aatccgcatcatgaacagtg;       (SEQ ID NO: 5)

R: tcatcatccattttatccacca;     (SEQ ID NO: 6)
UPL Probe # 69;

rat:
F: ttcggctcagtggagagg;         (SEQ ID NO: 7)

R: gctcccaccatttctccag;        (SEQ ID NO: 8)
UPL Probe # 71.

Target genes:
Alpha 1A-AR mouse
F: attgtggtgggatgcttcgtcct;    (SEQ ID NO: 9)

R: tgtttccggtggcttgaaattcgg;   (SEQ ID NO: 10)
UPL Probe # 105;

rat
F: ggttgcttcgtcctctgct;        (SEQ ID NO: 11)

R: gaaatccgggaagaaagacc;       (SEQ ID NO: 12)
UPL Probe # 105;

ANF mouse
F: cacagatctgatggatttcaaga;    (SEQ ID NO: 13)

R: cctcatcttctaccggcatc;       (SEQ ID NO: 14)
UPL Probe # 25;

rat
F: cacagatctgatggatttcaaga;    (SEQ ID NO: 15)

R: cctcatcttctaccggcatc;       (SEQ ID NO: 16)
UPL Probe # 25;
```

```
skAct mouse
F: cctgccatgtatgtggctatc;        (SEQ ID NO: 17)

R: ccagaatccaacacgatgc;          (SEQ ID NO: 18)
UPL Probe # 56;

rat
F: tgaagcctcacttcctaccc;         (SEQ ID NO: 19)

R: cgtcacacatggtgtctagtttc;      (SEQ ID NO: 20)
UPL Probe # 81;

MHC-beta mouse
F: ctgcaggacctggtggac;           (SEQ ID NO: 21)

R: ggaacttggacaggttggtg;         (SEQ ID NO: 22)
UPL Probe # 64;

rat
F: ctccacgcaccctcactt;           (SEQ ID NO: 23)

R: catgaccaggggttgtc;            (SEQ ID NO: 24)
UPL Probe # 80;

PGC1-alpha mouse
F: agcctgcgaacatatttgaga;        (SEQ ID NO: 25)

R: atgagggcaatccgtcttc;          (SEQ ID NO: 26)
UPL probe # 47;

rat
F: gcagtcgcaacatgctca;           (SEQ ID NO: 27)

R: gggtcatttggtgactctgg;         (SEQ ID NO: 28)
UPL probe # 6.
```

Mouse Echocardiography:

Conscious transthoracic echocardiography was performed on loosely restrained mice in the McAllister Heart Institute Animal Models Core using a VisualSonics Vevo 2100 ultrasound system (VisualSonics, Inc., Toronto, Ontario, Canada). Two-dimensional and M-mode echocardiography were performed in the parasternal long-axis view at the level of the papillary muscle. Left ventricular systolic function was assessed by fractional shortening (% FS= [(LVEDD−LVESD)/LVEDD]×100). Reported values represent the average of at least five cardiac cycles per mouse. Sonographers and investigators were blinded to mouse treatment condition during image acquisition and analysis.

Mouse Heart Histology:

Mice were heparinized and the heart was perfused with 10 mL PBS followed by 20 mL of 4% PFA/PBS through a 23 G butterfly needle, excised and placed in 4% PFA/PBS for 24 hours then transferred to 70% EtOH. Hearts were stained using standard methods in the UNC Histology Research Core. Fibrosis was analyzed in 3 Masson Trichrome (MT)-stained sections of 4 or 5 hearts from each treatment group. Slides were scanned using an Aperio ScanScope (Aperio Technologies, Vista, Calif.) and analyzed in Aperio ImageScope software. The Algorithm Positive Pixel Count v9 was used to measure collagen staining by MT using hue value (0.66) and hue width (0.1) The N positive/N total value was used to determine a weighted average collagen content (%) for each section.

RNAseq:

RNAseq was performed at the Carolina Center for Genome Sciences High Throughput Sequencing Facility. Libraries were prepared using an Illumina RNA TruSeq kit for total RNA. Single read sequencing (1×100) was performed on an Illumina HiSeq 2000 system. QC-passed reads were aligned to the mouse reference genome (mm9) using MapSplice.3 The alignment profile was determined by Picard Tools v1.64 (broadinstitute.github.io/picard/). Aligned reads were sorted and indexed using SAMtools and translated to transcriptome coordinates then filtered for indels, large inserts, and zero mapping quality using UBU v1.0 (github.com/mozack/ubu). Transcript abundance estimates for each sample were performed using RSEM, an expectation-maximization algorithm4 using the UCSC knownGene transcript and gene definitions. Raw RSEM read counts for all RNAseq samples were normalized to the overall upper quartile.5 Gene level differential expression testing was performed using the method of Love et al. (2014) implemented in the R package DESeq2. Gene set level tests were performed using the method of Efron and Tibshirani (2006) and gene sets as defined in the molecular signatures database, mSigdb.6 .GEO accession number is pending.

ATP Activity Assay:

Mouse hearts were removed and immediately processed for luciferin-luciferase ATP assay (ThermoFisher Scientific A22066) according to manufacturer instruction. Tissue was homogenized and heated at 95 C for 7 minutes, centrifuged at 14000 rpm for 5 minutes. Total protein in the supernatant was quantified using the Bradford Assay (Pierce #23200). Luminescence was measured at 560 nm.

NRVM Isolation and Culture:

Female Sprague-Dawley rats were from Charles River. NRVMs were isolated as previously described.7 Briefly, hearts from 1-2 day old rat pups were minced, digested serially in collagenase (Worthington)-containing solution, filtered, then pre-plated to exclude non-myocytes. NRVMs were then plated on laminin-coated dishes in DMEM with 5% fetal bovine serum (Sigma F2442) for 24 hours. Experiments were carried out after 36-96 hours of serum starvation in the presence of insulin, transferrin, and BrdU.

ERK Activation in NRVMs:

Serum-starved NRVMs were treated for 15 minutes with adrenergic agonists and antagonists then lysed rapidly on ice in RIPA buffer containing protease (Sigma P8340) and phosphatase inhibitors (Roche PhosSTOP #04906837001). Lysates were flash frozen and stored at −80 C.

Annexin V-Fluos:

After 36 h serum starvation, NRVMs were treated with DOX 2□M or vehicle in the presence and absence of dabuzalgron 10□M for 4 hrs. Cells were washed with cold PBS two times then incubated with 200 μl binding buffer (10 mM HEPES, 140 mM NaCl, and 2.5 mM CaCl2, pH 7.4) including 10 μL fluorescein isothiocyanate (FITC)-labeled Annexin V, 2 μL propidium iodide (PI) and 1 μg/mL Hoechst 33342 (Molecular Probes, USA) for 15 min at room temperature. They were examined under a epifluorescence microscopy (Olympus IX81 Inverted Light Microscope, UNC Microscopy Core). Images were analyzed using Image J software. The experiment was carried out three independent times with duplicates of each treatment condition. An average of 352 nuclei were counted in an average of 6 microscopic fields per experiment.

Mitochondrial membrane potential: Mitochondrial membrane potential in NRVMs was determined by 5, 5', 6, 6'-tetrachloro-1, 1', 3, 3'-tetraethylbenzimidazolylcarbocyanine iodide (JC-1) reduction. Cells were stained with JC-1 (Mitoprobe, Cayman Chemical Company) according to the manufacturer's protocol. In brief, serum-starved NRVMs were treated with DOX or vehicle in the presence or absence of dabuzalgron. JC-1 2 μM was added to each for 30 min. Cells were washed once with medium then analyzed by plate reader (CLARIOstar, BMG LABTECH, Germany). JC-1 green fluorescence was excited at 488 nm and emission was detected using a 530±40 nm filter. JC-1 red fluorescence was excited at 488 nm and emission was detected using a 613±20 nm filter.

Immunoblotting and Antibodies:

Homogenized tissue or cells were lysed in RIPA buffer with protease and phosphatase inhibitor (as above) and the lysate was passed through a Qiashredder. Equal protein abundance was assured with the Bradford assay (tissue lysates) or equal cell number (NRVMs). Samples were run for 2 hours at 140 v on ice on a Novex NuPAGE 4-12% Bis-Tris gel then transferred to a PVDF membrane at 90V for 1 hour on ice. Membranes were blocked in 5% milk at room temperature for 1 hour. We used Cell Signaling kit #9100 (pERK Thr202/Tyr204 1:250, ERK 1:1000, anti-rabbit HRP 1:1000). BID: (Santa Cruz, SC-11423); Cytochrome C: (Santa Cruz, SC-13560); AIF: (Santa Cruz, SC-13116); Caspase 8: (MBL international corporation, JM-3020-100); PARP: (Cell Signaling, #9532); Caspase 3: (Cell Signaling, #9665); Cleaved caspase 3: (Cell Signaling, #9664)

Drugs:

Dabuzalgron was synthesized. We also used norepinephrine (Sigma #N5785), propranolol (Sigma P-8688), DOX (Tocris #2252), and trametinib (Selleck S2673).

Statistics:

All results are presented as mean±SEM. Comparisons were made using t-test (groups of 2) or one-way ANOVA (groups of 3) with Tukey's post-hoc analysis (GraphPad Prism). EC50 for ERK activation was calculated using sigmoidal dose-response analysis (Prism).

REFERENCES

1. O'Connell T D, Jensen B C, Baker A J, Simpson P C. Cardiac alpha1-adrenergic receptors: Novel aspects of expression, signaling mechanisms, physiologic function, and clinical importance. *Pharmacological reviews*. 2014; 66:308-333. 2. Turnbull L, McCloskey D T, O'Connell T D, Simpson P C, Baker A J. Alpha 1-adrenergic receptor responses in alpha 1ab-ar knockout mouse hearts suggest the presence of alpha 1d-ar. *Am J Physiol Heart Circ Physiol*. 2003; 284:H1104-1109 3. Jensen B, Swigart P, Laden M-E, DeMarco T, Hoopes C, Simpson P. The alpha-1d is the predominant alpha-1-adrenergic receptor in human epicardial coronary arteries. *JACC*. 2009; 54:1137-1145 4. Lin F, Owens W A, Chen S, Stevens M E, Kesteven S, Arthur J F, Woodcock E A, Feneley M P, Graham R M. Targeted alpha(1a)-adrenergic receptor overexpression induces enhanced cardiac contractility but not hypertrophy. *Circ Res*. 2001; 89:343-350. 5. Rorabaugh B R, Ross S A, Gaivin R J, Papay R S, McCune D F, Simpson P C, Perez D M. Alpha1a—but not alpha1b-adrenergic receptors precondition the ischemic heart by a staurosporine-sensitive, chelerythrine-insensitive mechanism. *Cardiovasc Res*. 2005; 65:436-445. 6. Du X J, Gao X M, Kiriazis H, Moore X L, Ming Z, Su Y, Finch A M, Hannan R A, Dart A M, Graham R M. Transgenic alpha1a-adrenergic activation limits post-infarct ventricular remodeling and dysfunction and improves survival. *Cardiovasc Res*. 2006; 71:735-743. 7. Du X J, Fang L, Gao X M, Kiriazis H, Feng X, Hotchkin E, Finch A M, Chaulet H, Graham R M. Genetic enhancement of ventricular contractility protects against pressure-overload-induced cardiac dysfunction. *J Mol Cell Cardiol*. 2004; 37:979-987. 8. ALLHAT CRG. Major cardiovascular events in hypertensive patients randomized to doxazosin vs chlorthalidone: The antihypertensive and lipid-lowering treatment to prevent heart attack trial (allhat). [see comments]. *Jama*. 2000; 283:1967-1975. 9. Blue D R, Daniels D V, Gever J R, Jett M F, O'Yang C, Tang H M, Williams T J, Ford A P. Pharmacological characteristics of ro 115-1240, a selective alpha1a/11-adrenoceptor partial agonist: A potential therapy for stress urinary incontinence. *BJU international*. 2004; 93:162-170. 10. Musselman D M, Ford A P, Gennevois D J, Harbison M L, Laurent A L, Mokatrin A S, Stoltz R R, Blue D R. A randomized crossover study to evaluate ro 115-1240, a selective alpha1a/11-adrenoceptor partial agonist in women with stress urinary incontinence. *BJU international*. 2004; 93:78-83. 11. Chan T, Dash R, Simpson P. An alpha-1a-adrenergic receptor subtype agonist prevents cardiomyopathy without increasing blood pressure (abstract). *Circulation*. 2008; in press. 12. Huang Y, Wright C D, Merkwan C L, Baye N L, Liang Q, Simpson P C, O'Connell T D. An alpha1a-adrenergic-extracellular signal-regulated kinase survival signaling pathway in cardiac myocytes. *Circulation*. 2007; 115:763-772. 13. Dash R, Chung J, Chan T, Yamada M, Banal J, Nishimura D, Yang P C, Simpson P C. A molecular mri probe to detect treatment of cardiac apoptosis in vivo. *Magnetic resonance in medicine*. 2011; 66:1152-1162. 14. van der Pal H J, van Dalen E C, Hauptmann M, Kok W E, Caron H N, van den Bos C, Oldenburger F, Koning C C, van Leeuwen F E, Kremer L C. Cardiac function in 5-year survivors of childhood cancer: A long-term follow-up study. *Archives of internal medicine*. 2010; 170:1247-1255. 15. Bloom M W, Hamo C E, Cardinale D, Ky B, Nohria A, Baer L, Skopicki H, Lenihan D J, Gheorghiade M, Lyon A R, Butler J. Cancer therapy-related cardiac dysfunction and heart failure: Part 1: Definitions, pathophysiology, risk factors, and imaging. *Circ Heart Fail*. 2016; 9:e002661. 16. Tokarska-Schlattner M, Zaugg M, Zuppinger C, Wallimann T, Schlattner U. New insights into doxorubicin-induced cardiotoxicity: The critical role of cellular energetics. *J Mol Cell Cardiol*. 2006; 41:389-405. 17. Bishop M J. Recent advances in the discovery of alpha1-adrenoceptor agonists. *Curr Top Med Chem*. 2007; 7:135-145. 18. Krege J H, Hodgin J B, Hagaman J R, Smithies O. A noninvasive computerized tail-cuff system for measuring blood pressure in mice. *Hypertension*. 1995; 25:1111-1115. 19. Wang K, Singh D, Zeng Z, Coleman S J, Huang Y, Savich G L, He X, Mieczkowski P, Grimm S A, Perou C M, MacLeod J N, Chiang D Y, Prins J F, Liu J. Mapsplice: Accurate mapping of rna-seq reads for splice junction discovery. *Nucleic acids research*. 2010; 38:e178. 20. Li B, Dewey C N. Rsem: Accurate transcript quantification from rna-seq data with or without a reference genome. *BMC bioinformatics*. 2011; 12:323. 21. Bullard J H, Purdom E, Hansen K D, Dudoit S. Evaluation of statistical methods for normalization and differential expression in mrna-seq experiments. *BMC bioinformatics*. 2010; 11:94. 22. Subramanian A, Tamayo P, Mootha V K, Mukherjee S, Ebert B L, Gillette M A, Paulovich A, Pomeroy S L, Golub T R, Lander E S, Mesirov J P. Gene set enrichment analysis: A knowledge-based approach for interpreting genome-wide expression profiles. *Proc Natl Acad Sci USA*. 2005; 102:15545-15550. 23. Simpson P, Savion S. Differentiation of rat myocytes in single cell cultures with and without proliferating nonmyocardial cells. Cross-striations, ultrastructure, and chronotropic response to isoproterenol. *Circ Res*. 1982; 50:101-116. 24. Gottlieb E, Armour S M, Harris M H, Thompson C B. Mitochondrial membrane potential regulates matrix configuration and cytochrome c release during apoptosis. *Cell*

Death Differ. 2003; 10:709-717 25. Varga Z V, Ferdinandy P, Liaudet L, Pacher P. Drug-induced mitochondrial dysfunction and cardiotoxicity. *Am J Physiol Heart Circ Physiol.* 2015; 309:H1453-1467. 26. Suliman H B, Carraway M S, Ali A S, Reynolds C M, Welty-Wolf K E, Piantadosi C A. The co/ho system reverses inhibition of mitochondrial biogenesis and prevents murine doxorubicin cardiomyopathy. *J Clin Invest.* 2007; 117:3730-3741. 27. Jensen B C, O'Connell T D, Simpson P C. Alpha-1-adrenergic receptors in heart failure: The adaptive arm of the cardiac response to chronic catecholamine stimulation. *J Cardiovasc Pharmacol.* 2014; 63:291-301. 28. Patel M B, Stewart J M, Loud A V, Anversa P, Wang J, Fiegel L, Hintze T H. Altered function and structure of the heart in dogs with chronic elevation in plasma norepinephrine. *Circulation.* 1991; 84:2091-2100. 29. Rokosh D G, Simpson P C. Knockout of the a1a/c-adrenergic receptor subtype: The a1a/c is expressed in resistance arteries and is required to maintain arterial blood pressure. *Proc Natl Acad Sci USA.* 2002; 99:9474-9479. 30. Rodrigo M C, Joho S, Swigart P M, Foster E, O'Connell T D, Grossman W, Simpson P. The alpha-1-b adrenergic receptor subtype is required for physiological cardiac hypertrophy in normal development (abstract). *Circulation.* 2005; 112:123. 31. Amin J K, Xiao L, Pimental D R, Pagano P J, Singh K, Sawyer D B, Colucci W S. Reactive oxygen species mediate alpha-adrenergic receptor-stimulated hypertrophy in adult rat ventricular myocytes. *J Mol Cell Cardiol.* 2001; 33:131-139. 32. Guo J, Gertsberg Z, Ozgen N, Steinberg S F. P66shc links alpha1-adrenergic receptors to a reactive oxygen species-dependent akt-foxo3a phosphorylation pathway in cardiomyocytes. *Circ Res.* 2009; 104:660-669 33. Cardinale D, Colombo A, Bacchiani G, Tedeschi I, Meroni C A, Veglia F, Civelli M, Lamantia G, Colombo N, Curigliano G, Fiorentini C, Cipolla C M. Early detection of anthracycline cardiotoxicity and improvement with heart failure therapy. *Circulation.* 2015; 131:1981-1988. 34. Rosca M G, Tandler B, Hoppel C L. Mitochondria in cardiac hypertrophy and heart failure. *J Mol Cell Cardiol.* 2013; 55:31-41. 35. Jensen B C, O'Connell T D, Simpson P C. Alpha-1-adrenergic receptors: Targets for agonist drugs to treat heart failure. *J Mol Cell Cardiol.* 2011; 51:518-528. 36. Jensen B C, Swigart P M, De Marco T, Hoopes C, Simpson P C. {alpha} 1-adrenergic receptor subtypes in nonfailing and failing human myocardium. *Circ Heart Fail.* 2009; 2:654-663. 37. Bristow M R, Minobe W, Rasmussen R, Hershberger R E, Hoffman B B. Alpha-1 adrenergic receptors in the nonfailing and failing human heart. *J Pharmacol Exp Ther.* 1988; 247:1039-1045. 38. Zakir R M, Folefack A, Saric M, Berkowitz R L. The use of midodrine in patients with advanced heart failure. *Congest Heart Fail.* 2009; 15:108-111. 39. Chaulet H, Lin F, Guo J, Owens W A, Michalicek J, Kesteven S H, Guan Z, Prall O W, Mearns B M, Feneley M P, Steinberg S F, Graham R M. Sustained augmentation of cardiac alpha1a-adrenergic drive results in pathological remodeling with contractile dysfunction, progressive fibrosis and reactivation of matricellular protein genes. *J Mol Cell Cardiol.* 2006; 40:540-552. 40. Collette K M, Zhou X D, Amoth H M, Lyons M J, Papay R S, Sens D A, Perez D M, Doze V A. Long-term alpha1b-adrenergic receptor activation shortens lifespan, while alpha1a-adrenergic receptor stimulation prolongs lifespan in association with decreased cancer incidence. *Age.* 2014; 36:9675. 41. Doze V A, Papay R S, Goldenstein B L, Gupta M K, Collette K M, Nelson B W, Lyons M J, Davis B A, Luger E J, Wood S G, Haselton J R, Simpson P C, Perez D M. Long-term alpha1a-adrenergic receptor stimulation improves synaptic plasticity, cognitive function, mood, and longevity. *Mol Pharmacol.* 2011; 80:747-758.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating cardiomyopathy in a patient in need of such treatment, said method comprising administering a therapeutically or prophylactically effective amount of dabuzalgron, a pharmaceutically acceptable salt, or prodrug thereof to said patient.

2. The method of claim 1, wherein said cardiomyopathy is associated with anthracycline administration, hypertension, heart valve disease, myocardial ischemia, or heart failure.

3. The method of claim 1, wherein said cardiomyopathy is associated with anthracycline administration.

4. The method of claim 3, wherein said anthracycline is doxorubicin, daunorubicin, epirubicin, idarubucin, adriamycin, or valrubicin.

5. The method of claim 3, wherein the dabuzalgron is co-administered with the anthracycline.

6. The method of claim 3, wherein the dabuzalgron is administered before administration of the anthracycline.

7. The method of claim 3, wherein the dabuzalgron is administered after administration of the anthracycline.

8. The method of claim 1, wherein said patient's blood pressure does not increase as a result of said administration.

9. The method of claim 1, wherein said patient's blood pressure increases by an amount equal to or less than 50, 40, 30, 20, 10, 9, 8, 7, 6, 5, 4, 3, 2, or 1 mmHg as a result of said administration.

10. The method of claim 9, wherein said blood pressure is a systolic blood pressure.

11. The method of claim 1, wherein said effective amount is between about 0.001 and 1000, 0.1 and 100, 1 and 50, or 5 and 25 micrograms/kilogram patient weight.

12. The method of claim 1, wherein said effective amount is about 20 micrograms/kilogram patient weight.

13. The method of claim 1, wherein said effective amount is 20 micrograms/kilogram patient weight.

14. The method of claim 1, wherein said effective amount is the total amount administered to said patient in a day.

15. The method of claim 1, wherein said administering is parenteral, intravenous, intraarterial, buccal, sublingual, oral, peroral, transdermal, or nasal.

\* \* \* \* \*